United States Patent [19]

Jung

[11] Patent Number: 4,855,420
[45] Date of Patent: Aug. 8, 1989

[54] CEPHALOSPORIN DERIVATIVES

[75] Inventor: Frederic H. Jung, Rilly la Montagne, France

[73] Assignee: Ici Pharma, Enghein-les-Bains, France

[21] Appl. No.: 37,788

[22] Filed: Apr. 13, 1987

Related U.S. Application Data

[62] Division of Ser. No. 616,891, Jun. 4, 1984, Pat. No. 4,678,761.

[30] Foreign Application Priority Data

Jun. 3, 1983 [EP] European Pat. Off. ........ 83401135.5

[51] Int. Cl.$^4$ .................. C07D 501/18; A61K 31/545
[52] U.S. Cl. .................................... 540/222; 540/215; 540/225
[58] Field of Search ............... 540/215, 225, 226, 227, 540/222

[56] References Cited

U.S. PATENT DOCUMENTS

| | | | |
|---|---|---|---|
| 4,386,089 | 5/1983 | Konig | 544/22 |
| 4,463,173 | 7/1984 | Jung | 540/225 |
| 4,492,692 | 1/1985 | Jung et al. | 540/225 |
| 4,560,749 | 12/1985 | Spry | 544/22 |
| 4,678,781 | 7/1987 | Jung | 540/225 |

FOREIGN PATENT DOCUMENTS

| | | |
|---|---|---|
| 0018595 | 11/1980 | European Pat. Off. . |
| 0088853 | 9/1982 | European Pat. Off. . |
| 0099297 | 1/1984 | European Pat. Off. . |
| 2025398 | 1/1980 | United Kingdom . |
| 2036738 | 7/1980 | United Kingdom . |
| 2046261 | 11/1980 | United Kingdom . |
| 1604724 | 12/1981 | United Kingdom . |
| 1155493 | 6/1989 | United Kingdom . |

OTHER PUBLICATIONS

J. Med. Chem., 1974, 17, 1312–1315 (Nomura et al.).

Primary Examiner—Nicholas S. Rizzo
Attorney, Agent, or Firm—Cushman, Darby & Cushman

[57] ABSTRACT

A cephalosporin derivative of the formula I:

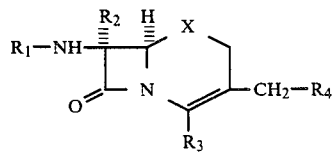

in which X is S, O, $CH_2$ or SO, R1 is (optionally-substituted) imidazol-2-yl or one of the C-7 acyl groups known in the cephalosporin art, R2 is hydrogen or methoxy, R3 is carboxy or a biodegradable ester thereof and -R4 is of the formula XII, XIII or XIV:

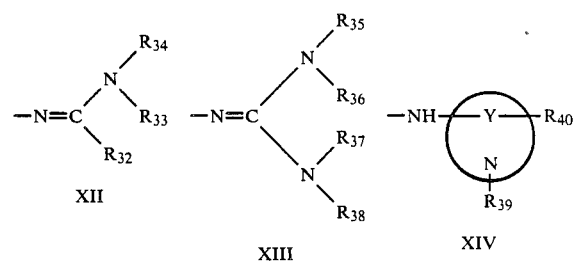

in which R32–R40 inclusive are as defined in the specification; and the salts thereof. Pharmaceutical compositions, methods of manufacture and intermediates are also described.

7 Claims, No Drawings

CEPHALOSPORIN DERIVATIVES

This a division of application Ser. No. 616,891, filed June 4, 1984 now U.S. Pat. No. 4,678,761.

This invention relates to cephalosporin derivatives which have antibacterial activity.

Over the years a large amount of effort has been devoted in cephalosporin chemistry to variations at the 3-position. Among the myriad of chemical types that have been introduced at this position of the nucleus, one which was first reported more than 10 years ago is the pyridiniothiomethyl radical (Nomura et al, *J. Med. Chem.*, 1974, 17, 1312-1315). This group has subsequently been introduced into cephalosporins containing other acylamino groups at the 7-position (UK Pat. No. 1,604,724, UK Patent Applications Nos. 2036738A and 2046261A and European Patent Publication No. 0088853) and the concept has more recently been extended to sulphur-linked compounds in which the quaternary group is located on an open chain structure (European Patent Publication No. 0099297). The pyridiniothiomethyl group may be readily introduced by reaction of a 3-acetoxymethylcephalosporin derivative with a pyridinethione derivative.

The cephalosporin derivatives corresponding to those described above in which the sulphur is replaced by nitrogen are unknown. This may in part be due to the fact that the displacement reaction corresponding to that described above would be much more difficult to achieve because of the poor nucleophilicity of the analogous nitrogen reagent under the usual conditions.

The nitrogen analogues are, however, readily prepared by the alternative reaction of a 3-aminomethylcephalosporin derivative with the appropriate chloropyridine. Indeed an analogous reaction process in cephalosporin chemistry for preparing 7-(pyridinioamino)-cephalosporin derivatives is already known (European Patent Publication No. 0018595). However, despite the fact that the required starting material, the 3-aminomethylcephalosporin derivative, has been known since 1967 (UK Pat. No. 1,155,493), the nitrogen analogues of the compounds described above have not heretofore been prepared. We have now discovered, and herein lies our invention, that cephalosporin derivatives carrying a standard 7-substituent and having at the 3-position a group $CH_2$—NH—R in which R can be, for example, a quaternised pyridine radical, are wide-spectrum antibacterial agents.

According to the invention there is provided a cephalosporin derivative of the formula I:

[Formula I]

in which X is sulphur, oxygen, methylene or sulphinyl (R or S configuration);

—R1 is of the formula II, III, IV, V, or VI:

[Formula II]

[Formula III]

[Formula IV]

[Formula V]

[Formula VI]

in which R5 and R6, same or different, are hydrogen, halogen, cyano, hydroxy, carboxy, pyridyl, (1-6C)alkyl, (1-6C)aminoalkyl, (1-6C)hydroxyalkyl, (2-6C)alkoxycarbonyl, (2-10C)alkylaminoalkyl, (3-15C)dialkylaminoalkyl, or phenyl optionally substituted by 1 or 2 radicals selected from halogen nitro, amino, hydroxy, carboxy, cyano, (1-6C)alkyl and (2-6C)alkoxycarbonyl;

R7 is carboxy, (2-6C)alkoxycarbonyl, benzyloxycarbonyl, carbamoyl, (2-6C)alkylcarbamoyl, (3-8C)dialkylcarbamoyl, carbazoyl, cyano or (2-6C)alkoxycarbonylamino;

R8 is hydrogen, (1-4C)alkyl, (1-4C)alkoxy, (2-5C)alkanoyl, (1-4C)alkylthio, (1-4C)alkanesulphinyl, (1-4C)alkanesulphonyl, phenyl, benzoyl, carboxy, (2-6C)alkoxycarbonyl, benzyloxycarbonyl, carbamoyl, carbazoyl, cyano, (2-5C)alkenyl, sulphamoyl, (1-4C)hydroxyalkyl, (2-4C)carboxyalkyl, benzyl, hydroxyphenyl, [(1-4C)alkoxy]phenyl, pyridyl or (methylthio)-thiadiazolyl;

R9 is hydrogen, (1-6C)alkyl or phenyl;

R10 is of the formula VII, VIII or IX:

[Formula VII]

[Formula VIII]

[Formula IX]

R11 is 2-aminothiazol-4-yl or 2-aminooxazol-4-yl each optionally substituted in the 5-position by fluorine, chlorine or bromine, or R11 is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R12 is hydrogen, (1-6C)alkyl, (3-8C)cycloalkyl, (1-3C)alkyl(3-6C)cycloalkyl, (3-6C)cycloalkyl, (1-3C)alkyl, (3-6C)alkenyl, (5-8C)cycloalkenyl, (3-6C)alkynyl, (2-5C)alkylcarbamoyl, phenylcarbamoyl, benzylcarbamoyl, triphenylmethyl, (1-3C)haloalkyl, (2-6C)hydroxyalkyl, (1-4C)alkoxy(2-4C)alkyl, (1-4C)alkylthio(2-4C)alkyl, (1-4C)alkanesulphinyl(1-4C)alkyl, (1-4C)alkanesulphonyl(1-4C)alkyl, (2-6C)aminoalkyl, (1-4C)alkylamino(2-6C)alkyl, (2-8C)dialkylamino(2-6C)alkyl, (1-5C)cyanoalkyl, (1-4C)azidoalkyl, (2-5C)ureidoalkyl, 3-amino-3-carboxypropyl, 2-(amidinothio)ethyl, 2-(N-aminoamidinothio)ethyl, tetrahydropyran-2-yl, thietan-3-yl or 2-oxotetrahydrofuran-3-yl, or —R12 is of the formula —$(CH_2)_n$—R13 in which n is 1 to 4 and R13 is piperidino, pyrrolidino, morpholino, piperazino or N-methylpiperazino, each value of R13 being optionally substituted by (1-4C)alkyl, phenyl or benzyl, or —R12 is of the formula —$(CH_2)_m$—W—R14 in which m is 0 to 3, W is sulphur or a direct bond, and R14 is phenyl or pyridinio(1-4C)alkylene or R14 is pyridyl, imidazolyl, 1,3,4-thiadiazolyl, tetrazolyl, 1-(1-4C)alkyltetrazolyl, thiazolyl, isothiazolyl or isoxazolyl in which the link with W is via a carbon or uncharged nitrogen, each value of R14 being optionally substituted, where possible, by one or two groups selected from (1-4C)alkyl, amino, hydroxy, carboxy, carbamoyl, nitro, (2-5C)alkoxycarbonyl, cyano and sulpho, or —R12 is of the formula —$(CH_2)_n$—CO—R15 in which n is 1 to 4 and R15 is (1-4C)alkyl, phenyl or benzyl, or —R12 is of the formula —COR16 or —(CH$_2$)$_n$—OCO—R16 in which n is 1–4 and R16 is hydrogen, (1–4C)alkyl, (1–4C)haloalkyl, phenyl or benzyl, or —R12 is of the formula —G—CH$_2$—R17 in which G is carbonyl or a direct bond and R17 is phthalimido, or —R12 is of the formula —N$^\oplus$R18R19R20 in which R18, R19 and R20 are (1–4C)alkyl, or R18 is (1–4C)alkyl and R19 and R20 are joined to form a (3–6C)carbocyclic ring, or R18, R19 and R20 are joined to form a 1-azonia-4-azabicyclo[2,2,2]octane or 1-azonia-3,5,7-triazatricyclo[3,3,1,1$^{3,7}$]decane, or —R12 is of the formula X:

[Formula X]

in which p is 1 or 2 and R21 and R22 are hydrogen or (1–4C)alkyl, or —R12 is of the formula —P(O)R23R24 in which R23 is hydroxy, (1–4C)alkoxy, (2–8C)dialkylamino, phenoxy, phenylamino or one of the values given above for R13, and R24 is (1–4C)alkyl, (1–4C)alkoxy, (2–8C)dialkylamino, phenoxy, phenylamino, piperidino, pyrrolidino, morpholino, piperazino or N-methylpiperazino, or —R12 is of the formula —CH$_2$P(O)R25R26 in which R25 and R26 are hydroxy or (1–4C)alkoxy, or —R12 is of the formula —CH(SR27)COOR28 in which R27 is (1–4C)alkyl and R28 is hydrogen or (1–6C)alkyl, or —R12 is of the formula XI:

[Formula XI]

in which m is 0–3, R29 is hydrogen, (1–3C)alkyl or methylthio, R30 is hydrogen, (1–3C)alkyl, (3–7C)cycloalkyl, cyano, carboxy, (2–5C)carboxyalkyl or methanesulphonylamino, or phenyl optionally substituted by amino or hydroxy, or R29 and R30 are joined to form, together with the carbon to which they are attached, a (3–7C)carbocyclic ring and R31 is hydroxy, amino, (1–4C)alkoxy, (1–4C)alkylamino, phenylamino or of the formula R13 given above or of the formula NHOR32 in which R32 is hydrogen, (1–4C)alkyl, phenyl or benzyl, provided that when R12 contains phenyl, and unless otherwise stated, the phenyl is optionally substituted by 1 or 2 groups selected from halogen, hydroxy, amino, carboxy, nitro, carbamoyl, cyano, and aminomethyl;

R2 is hydrogen or methoxy;

R3 is carboxy or a biodegradable ester thereof;

—R4 is of the formula XII, XIII or XIV:

[Formula XII]

[Formula XIII]

[Formula XIV]

or a tautomeric form thereof, in which the radical of the formula XII, XIII or XIV may carry a positive charge, or any possible deprotonated form of such a charged species, and in which R32 is hydrogen, (1–6C)alkyl, phenyl, naphthyl or —(CH$_2$)$_q$—COOR41 in which q is 1 to 6 and R41 is hydrogen or (1–6C)alkyl;

R33 and R34 are selected from hydrogen, (1–6C)alkyl, hydroxy, cyano, phenyl, naphthyl, phenyl(1–6C)alkyl, heteroaryl and —(CH$_2$)$_q$—COOR41 in which q and R41 have the meanings given above, or R33 and R34 are joined to form, together with the nitrogen to which they are attached, a pyrrolidine, piperidine, morpholine or hexahydroazepine ring, said ring being optionally fused to a benzene ring;

or R32 and R33 are joined to form, together with the carbon and nitrogen to which they are attached, a 5- or 6-membered saturated ring to which may optionally be fused a benzene ring;

R35 and R37 are selected from hydrogen, (1–6C)alkyl, phenyl(1–6C)alkyl and —(CH$_2$)$_q$COOR41 in which q is 1 to 6 and R41 is hydrogen or (1–6C) alkyl;

R36 and R38 are selected from hydrogen, (1–6C)alkyl, phenyl, naphthyl and phenyl(1–6C)alkyl;

or R36 and R37 are joined as a carbon chain to form, together with the nitrogen-carbon-nitrogen chain to which they are attached, a saturated or partially unsaturated 5- or 6-membered ring to which may optionally be fused a benzene ring;

ring Y is pyridine, pyrimidine, oxazole, thiazole, isoxazole, isothiazole, or imidazole to each of which is optionally fused, when possible, a benzene, cyclopentane or cyclohexane ring;

R39 is hydrogen, amino, (1–6C)alkyl, (3–6C)cycloalkyl, (3–6C)alkenyl, (2–8C)alkoxyalkyl, —(CH$_2$)$_q$—COOR41, —(CH$_2$)$_q$—CONH$_2$, —(CH$_2$)$_q$—S(O)$_s$—R42 or —(CH$_2$)$_q$—NHCO—R42 in which q is 1 to 6, R41 is hydrogen or (1–6C)alkyl, s is 0, 1 or 2 and R42 is (1–6C)alkyl or (1–6C) alkoxy, or R39 is (3–8C)alkanoylmethyl, benzoylmethyl, (1–6C)primaryhydroxyalkyl, (1–6C)primaryaminoalkyl, (1–4C)alkylamino(1–6C)alkyl, di(1–4C)alkylamino(1–6C)alkyl, (1–6C)alkoxy, (1–6C)alkylamino, phenyl(1–6C)alkyl, phenyl(1–6C)alkoxy, (1–4C)alkoxy(1–4C)alkyl, (1–4C)alkoxy(2–4C)alkoxy(1–4C)alkyl, or of the formula (CH$_2$)$_n$—N=CR43NR44R45 or (CH$_2$)$_n$C(NR43)NR44R45 (or a tautomer thereof) in which n is 1 to 4 and R43, R44 and R45, same or different, are hydrogen or (1–4C)alkyl;

R40 is hydrogen or one or two substituents selected from halogen, amino, nitro, (1–6C)alkyl, carboxy, (2–6C)alkoxycarbonyl, (1–6C)alkoxy, cyano, carbamoyl, (1–6C)haloalkyl, (1–6C)azidoalkyl, (1–6C)aminoalkyl, (2–4C)aminoalkylthio(1–4C)alkyl, (2–6C)alkanoylamino, (2–6C)alkanoylamino(1–4C)alkyl, (2–6C)alkanoyloxy(1–4C)alkyl, benzyl, benzyloxy and heteroarylthio;

wherein when R33, R34, R35, R36, R37, R38, R39 or R40 individually is or contains phenyl or naphthyl, the phenyl or naphthyl is optionally substituted by one or two radicals selected from halogen, nitro, cyano, carboxy, hydroxy, carbamoyl, (1–6C)alkyl, (1–6C)alkoxy and (2–6C)alkoxycarbonyl, and wherein when R33 or R34 is heteroaryl, or R40 is heteroarylthio, the heteroaryl ring is a 5- or 6-membered ring containing 1, 2 or 3 hetero atoms selected from oxygen, nitrogen and sulphur;

and, when the compound of the formula I does not carry a positive charge, the pharmaceutically-acceptable acid addition salts thereof, and where the compound of the formula I carries a carboxy, the pharmaceutically-acceptable base-addition salts thereof.

It is to be understood that in the above formula I and throughout this specification, the illustrated stereochemistry of the ceph-3-em nucleus is the absolute configuration. It is also to be understood that although the double bonds in formulae II, VIII, IX, XII and XIII have been inserted in particular positions, other tautomeric forms are, in certain instances, possible and these other forms are included within the scope of this invention.

Particular values for R5 and R6, same or different, are hydrogen, chlorine, bromine, cyano, hydroxy, carboxy, pyridyl, methyl, aminomethyl, hydroxymethyl, methoxycarbonyl, methylaminomethyl, or dimethylaminomethyl, or phenyl optionally substituted by 1 or 2 radicals selected from halogen, nitro, amino, hydroxy, carboxy, cyano, methyl and methoxycarbonyl.

A particular value for R27 is carboxy, methoxycarbonyl, benzyloxycarbonyl, carbamoyl, methylcarbamoyl, dimethylcarbamoyl, carbazoyl, cyano or methoxycarbonylamino.

A particular value for R8 is hydrogen, methyl, methoxy, acetyl, methylthio, methanesulphinyl, methanesulphonyl, phenyl, benzoyl, carboxy, methoxycarbonyl, benzyloxycarbonyl, carbamoyl, carbazolyl, cyano, allyl, sulphamoyl, methoxymethyl, carboxymethyl, benzyl, 4-hydroxyphenyl, 4-methoxyphenyl, pyridyl or 2-methylthio-1,3,4-thiadiazol-5-yl;

A particular value for R9 is hydrogen, methyl or phenyl.

A particular value for R12 is hydrogen, methyl, ethyl, isopropyl, t-butyl, cyclopropyl, cyclobutyl, cyclopentyl, cyclohexyl, methylcyclopropyl, methylcyclobutyl, methylcyclpentyl, methylcyclohexyl, cyclpropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, triphenylmethyl, 2-chloroethyl, 2-bromoethyl, 2-hydroxyethyl, 3-hydroxypropyl, 2-methoxyethyl, 2-ethoxyethyl, 2-methylthioethyl, 2-methanesulphinylethyl, 2-methanesulphonylethyl, 2-aminoethyl, 3-aminopropyl, 2-methylaminoethyl, 2-dimethylaminoethyl, cyanomethyl, 2-cyanoethyl, azidomethyl, 2-azidoethyl, 3-amino-3-carboxypropyl, 2-(amidino)ethyl, 2-(N-aminoamidino)ethyl, tetrahydropyran-2-yl, thietan-3-yl or 2-oxotetrahydrofuran-3-yl, or of the formula —$(CH_2)_n$—R13 in which n is 1 to 4 and R13 is piperidino, pyrrolidino, morpholino, piperazino or N-methylpiperazino, each value of R13 being optionally substituted by methyl, phenyl or benzyl, or of the formula —$(CH_2)_n$—W—R14 in which m is 0 to 3, W is sulphur or direct bond and R14 is phenyl, pyridiniomethylene, or 2-pyridinioethylene, or R14 is imidazolyl, 1,3,4-thiadiazolyl, tetrazolyl, 1-methyltetrazolyl, thiazolyl or isoxazolyl in which the link with W is via a carbon or uncharged nitrogen, each value of R14 being optionally substituted, where possible, by one or two groups selected from methyl amino, hydroxy, carboxy, carbamoyl, nitro, methoxycarbonyl, ethoxycarbonyl, cyano and sulpho, or of the formula —$(CH_2)_n$—CO—R15 in which n is 1 to 4 and R15 is methyl, ethyl, phenyl or benzyl, or of the formula —COR16 or —$(CH_2)_n$—OCO—R16 in which n is 1-4 and R16 is hydrogen, methyl, chloromethyl, bromomethyl, 2-chloroethyl, 2-bromoethyl, phenyl or benzyl, or of the formula —G—$CH_2$—R17 in which G is carbonyl or a direct bond and R17 is phthalimido, or of the formula —$N^{61}$ R18R19R20 in which R18, R19 and R20 are methyl or ethyl, or R18 is methyl or ethyl and R19 and R20 are joined to form a cyclopropyl, cyclobutyl, cyclopentyl or cyclohexyl ring, or R18, R19 and R20 are joined to form a 1-azonia-4-azabicyclo[2,2,2]octane or 1-azonia-3,5,7-triazatricyclo[3,3,1$^3$,$^7$]decane, or of the formula X:

[Formula X]

in which p is 1 or 2 and R21 and R22 are hydrogen or methyl, or of the formula —P(O)R23R24 in which R23 is hydroxy, (1–4C)alkoxy, (2–8C)dialkylamino, phenoxy, phenylamino or one of the values given above for R13 and R24 is (1–4C)alkyl, (1–4C)alkoxy, (2–8C)dialkylamino, phenoxy, phenylamino, piperidino, pyrrolidino, morpholino, piperazino or N-methylpiperazino, or of formula —$CH_2$P(O)R25R26 in which R25 and R26 are hydroxy, methoxy or ethoxy, or of the formula —CH(SR27)COOR28 in which R27 is methyl or ethyl and R28 is hydrogen, methyl, ethyl or isopropyl, or of the formula XI:

[Formula XI]

in which m is 0–3, R29 is hydrogen, methyl or methylthio, R30 is hydrogen, methyl, cyclopropyl, cyclobutyl, cyclopentyl, cyclohexyl, cyano, carboxy, carboxymethyl, 2-carboxyethyl or methanesulphonylamino, or phenyl optionally substituted by amino or hydroxy, or R29 and R30 are joined to form, together with the carbon to which they are attached, a cyclopropane, cycobutane, cyclopentane, cyclohexane or cycloheptane ring and R31 is hydroxy, amino, methoxy, ethoxy, methylamino, ethylamino, phenylamino or one of the particular values for R13 given above or of the formula NHOR32 in which R32 is hydrogen methyl, ethyl, phenyl or benzyl, provided that when R12 contains phenyl, and unless otherwise stated above, the phenyl is optionally sustituted by 1 or 2 groups selected from fluorine, chlorine, bromime, hydroxy, amino, carboxy, nitro, carbamoyl, cyano and aminomethyl.

A particular value for R3 is carboxy, COOCHR46OCOR47, COOCHR46SCOR47, COOCHR46COR47, COOCHR46OR47, COOCOOR46, COOCHR46OCOOR47, COOCH2CH2NR47R47, COOCHR46OCH2CH2OCH3, COOCH2OCO(CH2)$_r$-CHR48-NH2 or of the formula XV, XVI or XVII:

[Formula XV]

[Formula XVI]

[Formula XVII]

in which t is 0 or 1, R46 is hydrogen or methyl, R47 is hydrogen, methyl, ethyl or i-butyl, R48 is hydrogen, methyl, ethyl, n-propyl, i-propyl or t-butyl, R49 is methyl, ethyl, phenyl or benzyl, R50 is hydrogen or one, two or three radicals selected from chlorine, bromine, nitro, methyl, methoxy, methylthio, methanesulphinyl, methanesulphonyl, methoxycarbonyl, methoxythiocarbonyl, acetylamino, phenyl, phenoxy, phenylthio, benzenesulphinyl, benzenesulphonyl, phenoxycarbonyl, phenylthiocarbonyl or phenoxythiocarbonyl, R51 is hydrogen or one of the values given for R50 and R52 is hydrogen or one, two or three radicals selected from chlorine, bromine, methyl and methoxy.

Particular values for R32, R33 and R34 are as follows.

R32 is hydrogen, methyl, phenyl, naphthyl or —$(CH_2)_q$—COOR41 in which q is 1 to 6 and R41 is hydrogen or methyl, R33 and R34 are selected from hydrogen, methyl, hydroxy, cyano, phenyl, naphthyl, benzyl, furyl, pyrrolyl, thienyl, thiazolyl, isothiazolyl, oxazolyl, isoxazolyl, imidazolyl, pyrazolyl, 1,2,3-thiadiazolyl, 1,2,4-thiadiazolyl, 1,2,3,-oxadiazolyl, 1,2,4-oxadiazolyl, 1,2,3-triazolyl, 1,2,4-triazolyl, tetrazolyl, pyrimidinyl, pyridyl, pyrazinyl or —$(CH_2)_q$—COOR41 in which q and R41 have the meanings given above, or R33 and R34 are joined to form, together with the nitrogen to which they are attached, a pyrrolidine, piperidine, morpholine or hexahydroazepine ring, said ring being optionally fused to a benzene ring, or R32 and R33 are joined to form, together with the carbon and nitrogen to which they are attached, a 5- or 6-membered saturated ring to which may be optionally fused a benzene ring.

Particular values for R35, R36, R37 and R38 are as follows.

R35 and R37 are selected from hydrogen, methyl, benzyl and —$(CH_2)_q$COOR41 in which q is 1–6 and R41 is hydrogen or methyl, R36 and R38 are selected from hydrogen, methyl, phenyl, naphthyl and benzyl, or R36 and R37 are joined as a carbon chain to form, together with the nitrogen-carbon-nitrogen chain to which they are attached, a saturated or partially unsaturated 5- or 6-membered ring to which may optionally be fused a benzene ring.

A particular value for ring Y is a 2-, 3- or 4-linked pyridine, to each of which is fused a benzene or cyclopentane ring, a 2-, 4- or 5-linked pyrimidine, to each of which is fused a benzene or cyclopentane ring, a 2- or 4-linked imidazole, a 2- or 4-linked thiazole, a 2- or 4-linked oxazole, a 3- or 4-linked isothiazole or a 3- or 4-linked isoxazole ring. Included in the above is the quinolizinium ring system.

A particular value for R39 is hydrogen, amino, methyl, ethyl, n-propyl, i-propyl, t-butyl, cyclopropyl, cyclobutyl, cyclopentyl, cyclohexyl, allyl, but-3-enyl, but-4-enyl, methoxymethyl, 2-methoxyethyl, ethoxymethyl, —$(CH_2)_q$—COOR41, —$(CH_2)_q$—CONH$_2$, —$(CH_2)_q$—S(O)$_s$—R42 or —$(CH_2)_q$—NHCO—R42 in which q is 1 to 6, R41 is hydrogen or methyl, s is 0, 1 or 2 and R42 is methyl, ethyl, methoxy, ethoxy or t-butoxy, or R39 is acetylmethyl, benzoylmethyl, 2-hydroxyethyl, 2-aminoethyl, 2-methylaminoethyl, 2-dimethylaminoethyl, methoxy, ethoxy, n-propoxy, i-propoxy, methylamino, ethylamino, benzyl, 2-phenethyl, benzyloxy, 2-phenoxyethyl, (2-methoxyethoxy)methyl, or of the formula $(CH_2)_n$N=CR43NR44R45 or $(CH_2)_n$C(NR43)NR44R45 (or a tautomer thereof) in which n is 1 to 4 and R43, R44 and R45, same or different are hydrogen or methyl.

A particular value for R40 is hydrogen or one or two substituents selected from fluorine, chlorine, bromine, amino, nitro, methyl, ethyl, n-propyl, i-propyl, t-butyl, carboxy, methoxycarbonyl, ethoxycarbonyl, methoxy, ethoxy, cyano, carbamoyl, chloromethyl, bromomethyl, trifluoromethyl, 2-chloroethyl, azidomethyl, aminomethyl, 2-aminoethyl, (2-aminoethylthio)methyl, acetylamino acetylaminomethyl, 2-acetylaminoethyl, acetoxymethyl, 2-acetoxyethyl, benzyl, benzyloxy, furylthio, pyrrolylthio, thienylthio, thiazolylthio, isothiazolylthio, oxazolylthio, isoxazolylthio, imidazolythio, pyrazolylthio, 1,2,3-thiadiazolylthio, 1,2,4-thiadiazolylthio, 1,2,3-oxadiazolylthio, 1,2,4-oxadiazolylthio, 1,2,3-triazolylthio, 1,2,4-triazolylthio, tetrazolylthio, pyrimidinylthio, pyridylthio and pyrazinylthio.

In the above particular definitions when R33, R34, R35, R36, R37, R38, R39 or R40 individually is or contains phenyl or naphthyl, the phenyl or naphthyl is optionally substituted by one or two radicals selected from fluorine, chlorine, bromine, nitro, cyano, carboxy, hydroxy, carbamoyl, methyl, methoxy and ethoxycarbonyl.

The following are 22 preferred features of the cephalosporin derivative of the invention. When any one of these features is taken, either singly or in combination, with the other general or particular features of the cephalosporin derivative of the invention listed above, there are obtained preferred sub-groups of compounds.
  1. X is sulphur.
  2. R1 is of the formula II in which R5 and R6 are hydrogen.
  3. R1 is of the formula III in which R7 is carboxy and R8 is carbamoyl.
  4. R1 is formula VI.
  5. R2 is hydrogen.
  6. R3 is carboxy.
  7. R4 is of the formula XIV.
  8. R11 is 2-aminothiazol-4-yl.
  9. R12 is (1–6C)alkyl, (3–6C)alkenyl, (3–6C)alkynyl, (3—8C)cycloalkyl, (3–6C)cycloalkyl(1–3C)alkyl, (1–3C)haloalkyl, (1–5C)cyanoalkyl, (2–6C)hydroxyalkyl, (1–4C)alkoxy(2–4C)alkyl, (2–6C)aminoalkyl or benzyl.
  10. R12 is methyl, ethyl, i-propyl, allyl, propargyl, cyclopentyl, cyclopropylmethyl, 2-chloroethyl, 2-bromoethyl, cyanomethyl, 2-cyanoethyl, 2-hydroxyethyl, 2-ethoxyethyl or benzyl.
  11. R12 is of the formula XI.
  12. In formula XI m is 0.
  13. In formula XI R31 is hydroxy or (1–4C)alkoxy.
  14. In formula XI R29 and R30 are both hydrogen or (1–3C)alkyl or R29 and R30 are joined to form, together with the carbon to which they are attached, a 3–7C carbocyclic ring.
  15. In formula XI R29 and R30 are both hydrogen or methyl or R29 and R30 are joined to form, together with the carbon to which they are attached, a cyclobutyl or cyclopentyl ring.
  16. —R4 is of the formula XIV.
  17. Ring Y is pyridine to which is optionally fused a benzene or cyclopentane ring, pyrimidine to which is optionally fused a benzene ring, thiazole or isoxazole.
  18. Ring Y is a 4-linked pyridine to which is optionally fused a benzene or cyclopentane ring in the 2,3-position, or a 2- or 4-linked pyrimidine, to which is optionally fused a benzene ring in the 5,6-position.
  19. R39 is (1–6C)alkyl, (3–6C)alkenyl, $(CH_2)_q$—CONH$_2$, $(CH_2)_q$—S(O)$_s$—R42 or $(CH_2)_q$—NHCO—R42 [in which R42 is (1–6C)alkyl], (1–6C)primaryhydroxyalkyl, (1–6C)-primaryaminoalkyl, (3–8C)alkaneoylmethyl, phenyl(1–6C)alkyl [in which the phenyl is optionally substituted], $(CH_2)_n$N=CR43NR44R45 or $(CH_2)_n$C(NR43)NR44R45.
  20. R39 is methyl, ethyl, n-propyl, i-propyl, allyl, carbamoylmethyl, (2-acetylamino)ethyl, methylthiomethyl, 2-hydroxyethyl, 2-aminoethyl, 4-nitrobenzyl, $CH_2CH_2N$=C(CH$_3$)NH$_2$ or $CH_2C(NH)NH_2$.

21. R40 is hydrogen, halogen, amino, (1-6C)alkyl, (1-6C)alkoxy or carbamoyl.
22. R40 is hydrogen, fluorine, amino, methyl, methoxy or carbamoyl.

Particular compounds of the invention are described in the Examples. The following Table contains a group of preferred compounds. Of these the group consisting of the compounds of Examples 23, 25, 32, 36, 42, 59, 62, 63, 73 and 122 is particularly preferred.

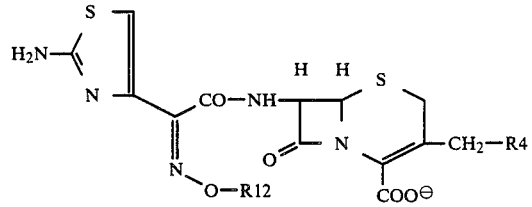

| Example | —R12 | —R4 |
|---|---|---|
| 23 | —C(CH3)2COOH | —NH—(pyridinium)—N⊕—CH3 |
| 25 | —C(CH3)2COOH | —NH—(3-methylpyridinium)—N⊕—CH3, CH3 |
| 32 | —C(CH3)2COOH | —NH—(cyclopentapyridinium)—N⊕—CH3 |
| 36 | —C(CH3)2COOH | —NH—(pyridinium)—N⊕—CH2CH2NH2 |
| 59 | —C(CH3)2COOH | —NH—(pyridinium)—N—CH(CH3)2 |
| 42 | —C(CH3)2COOH | —NH—(3-fluoropyridinium)—N⊕—CH3, F |
| 63 | —C(CH3)2COOH | —NH—(quinolinium)—N⊕ |
| 62 | —C(CH3)2COOH | —NH—(pyridinium)—N⊕—CH2CH=CH2 |
| 122 | —C(CH3)2COOH | —NH—(quinolinium)—N⊕—CH3 |
| 73 | —CH2COOH | —NH—(pyridinium)—N⊕—CH3 |
| 41 | —C(CH3)2COOH | —NH—(pyridinium)—N⊕—CH2CONH2 |
| 110 | —C(CH3)2COOH | —NH—(pyridinium)—N⊕—CH2—C6H4—NO2 |
| 84 | —C(CH3)2COOH | —NH—(methylpyrimidinium)—N⊕—CH3, CH3 |
| 85 | —C(CH3)2COOH | —NH—(thiazolium)—⊕N—CH3 |
| 86 | —C(CH3)2COOH | —NH—(dimethylisoxazolium) CH3, CH3 |
| 131 | ⌗—COOH | —NH—(pyridinium)—N⊕—CH2CH2NH2 |
| 103 | —O—CH2CH2Cl | —NH—(pyridinium)—N⊕—CH2CH2NH2 |
| 67a | ⌗—COOH | —NH—(pyridinium)—N⊕—CH2CH=CH2 |

-continued

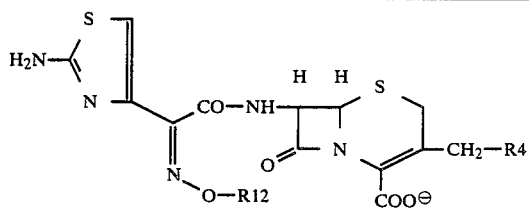

| Example | —R12 | —R4 |
|---|---|---|
| 16 | —CH₃ | —NH—[indane-fused pyridinium]—N⊕—CH₃ |
| 67 | —CH₂CH₃ | —NH—[pyridinium]—N⊕—CH₃ |
| 39 | —C(CH₃)₂COOH | —NH—[pyridinium with ⊕N—CH₃] |
| 72 | —CH(CH₃)₂ | —NH—[pyridinium]—N⊕—CH₃ |
| 96 | —CH₂CN | —NH—[pyridinium]—N⊕—CH₃ |
| 117 | —CH₃ | —NH—[quinolinium with ⊕N—CH₃] |

A suitable acid-addition salt of the cephalosporin derivative of the invention is for example, a salt formed with hydrochloric, hydrobromic, phosphoric, sulphuric, citric or maleic acid. A suitable base-addition salt of the cephalosporin derivative of the invention is, for example, an alkali metal salt (e.g. a sodium or potassium salt), an alkaline earth metal salt (e.g. a calcium or magnesium salt), or a salt with a primary, secondary or tertiary organic amine (e.g. triethylamine, procaine, dibenzylamine and N,N₁-dibenzyl ethylenediamine, and other amines which have been used to form salts with cephalosporins).

The cephalosporin derivative of the invention may be manufactured by methods known in themselves for the manufacture of chemically analogous compounds. The following processes, X,R1, R2, R3 and R4 having the meanings stated above, unless indicated otherwise, are therefore provided as further features of the invention.

The process of the invention is characterised by:
(a) reaction of a compound of the formula XVIII:

[Formula XVIII]

by addition of the amino group to an activated C=C or C=N bond carrying on carbon the radical R50, followed by elimination of HR50 from the product, where R50 is a displaceable radical. A particular value for R50 is, for example, halogen (e.g. fluorine, chlorine or bromine), (1-6C)alkoxy (e.g. methoxy, ethoxy), phenoxy, (1-6C)alkylthio (e.g. methylthio), tri(1-4C)alkylammonium (e.g. trimethylammonium), di(1-4C)alkylsulphonium (e.g. dimethylsulphonium), (1-6C)alkanesulphinyl (e.g. methanesulphinyl), (1-6C) alkanesulphonyl (e.g. methanesulphonyl), (1-6C)alkanesulphonyloxy (e.g. methanesulphonyloxy), benzenesulphonyl, benzenesulphonyloxy, toluene-p-sulphonyl or toluene-p-sulphonyloxy. The reaction may be carried out in a diluent or solvent such as water or a water-miscible fluid such as dimethylformamide, acetonitrile, dimethyl sulphoxide, nitromethane, 1,3-dimethyl-2-oxotetrahydropyrimidine or 1,3-dimethyl-2-oxodihydroimidazole, or a mixture of any two or three of these. It is generally preferable to conduct the reaction in the presence of a base such as triethylamine or sodium bicarbonate. The base may be present in excess, for example up to 20 molar excess. The reaction may be conducted in the temperature range 0° to 90° C., and preferably in the range ambient temperature to 40° C.

(b) for those compounds which carry a hydroxy and/or amino radical, deprotection of the corresponding compound which carries a protecting group in place of the relevant hydrogen atom.

For those compounds in which the hydroxy is part of a carboxy group a particularly useful protecting group is diphenylmethyl, 4-methoxybenzyl or 2,4-dimethoxybenzyl (removable by treatment with a strong organic acid, for example trifluoroacetic acid), t-butyl (removable with a strong organic acid, for example trifluoroacetic or formic acid), trisubstituted silyl (for example trialkylsilyl such as trimethylsilyl or t-butyldimethylsilyl, or diphenylmethylsilyl or diphenyl-t-butylsilyl) (removable by treatment with water), benzyl, for example 2- or 4-nitrobenzyl or 4-methoxybenzyl (removable by hydrogenolysis or with a Lewis acid catalyst [for example AlCl₃]), 2,2,2-trichloroethyl (removable with zinc/acetic acid), allyl (removable with a palladium(O) catalyst), 2-trialkylsilylethyl, for example 2-trimethylsilylethyl (removable with fluoride) or 4-nitrobenzyl (removable with dithionite) or acetonyl (removable with one equivalent of base).

For those compounds in which the hydroxy is contained in an oxime group, a particularly suitable protecting group is triphyenylmethyl, tetrahydropyran-2-yl or 2-methoxyprop-2-yl (all removable with acid).

For those compounds in which the hydroxy is contained in an aliphatic alcohol, a particularly suitable protecting group is one of those described above for an oxime hydroxy or, trisubstitutedsilyloxycarbonyl (for example trialkylsilyoxycarbonyl such as trimethylsilyloxycarbonyl or t-butyldimethylsilyloxycarbonyl,) (removable by treatment with water), optionally substituted benzyloxycarbonyl, for example 2- or 4-nitrobenzyloxycarbonyl or 4-methoxybenzyloxycarbonyl (removable by hydrogenolysis or with a Lewis and catalyst [for example AlCl$_3$]), 2,2,2-trichloroethoxycarbonyl (removable with zinc/acetic acid), allyloxycarbonyl (removable with a palladium(O) catalyst), 2-methoxyethoxymethyl (removable with a Lewis acid catalyst, for example AlCl$_3$), chloroacetyl (removable with thiourea) or formyl (removable with acid or mild base).

For those compounds which carry an alphatic amino group, any of the amino protecting groups known in peptide chemistry may be used. Examples of such groups are benzyloxycarbonyl (removable by hydrogenolysis or by treatment with acid), t-butoxycarbonyl or allyloxycarbonyl (removable with acid) and 2-trimethylsilylethoxycarbonyl (removable with fluoride).

For those compounds which carry an aromatic amino group, and in particular for those compounds in which R1 is of the formula VI, any of the above protecting groups for aliphatic amino may be used. Additional useful protecting groups are formyl and triphenylmethyl (removable with acid) and chloroacetyl (removable with thiourea).

(c) for those compounds in which R1 is of the formula II, reaction of a compound of the formula XIX:

[Formula XIX]

with a compound of the formula XX:

[Formula XX]

in which R50 is a displaceable radical. R50 is, for example a halogen atom, preferably a fluorine or chlorine atom. The reaction may be conducted in the presence of a diluent or solvent, for example acetonitrile, dimethylformamide or tetrahydrofuran, or a mixture of any two of these, and it may be accelerated or completed by the application of heat, for example by heating to the boiling point of the diluent or solvent.

(d) for those compounds in which X is sulphinyl, oxidation of the corresponding compound in which X is sulphur. For the manufacture of those compounds in which the resulting sulphoxide has the S absolute configuration the oxidising agent may be, for example, a peroxide such as hydrogen peroxide (optionally used in the presence of metal ions), a peracid such as performic, peracetic trifluoroperacetic, perbenzoic or metachlorperbenoic acid or a periodate such as sodium metaperiodate. For the manufacture of those compounds in which the resulting sulphoxide has the R absolute configuration, the oxidising agent may be, for example, ozone, iodosobenzene or phenyliodonium dichloride. The reaction may be carried out in water or an organic solvent such as methylene chloride or dioxane, at a temperature of $-70°$ C. to ambient.

(e) for those compounds in which R4 is of the formula XIV in which R39 is of the formula $(CH_2)_nN=CR43NR44R45$, reaction of a compound of the formula I in which R4 is of the formula XIV in which R39 is of the formula $(CH_2)_n$—NH$_2$ with a compound of the formula R34R50C=NR44R45 followed by elimination of HR50 from the product, where R50 is a displaceable radical. A particular value for R50 and particular reaction conditions are, for example, the same as those described for process (a).

(f) for those compounds in which R1 is of the formula III, IV, V, or VI, acylation of a compound of the formula XIX:

[Formula XIX]

with an acid of the formula R51—OH in which R51— is of the formula III, IV, V or VI, or an activated derivative thereof. A particular activated derivative is, for example, an acid chloride, acid bromide, anyhydride, or an ester formed with 1-hydroxybenztriazole, 4-hydroxybenz-1,2,3-triazine or 2-mercaptobenzthiazole. Alternatively the acylation may be carried out using free acid in the presence of a carbodiimide such as dicyclohexylcarbodiimide.

(g) for those compounds in which R1 is of the formula VI in which R12 is other than hydrogen, reaction of a compound of the formula I in which R1 is of the formula VI in which R12 is hydrogen with a compound of the formula R50—R52 in which R50 is a displaceable radical and 52 has one of the values for R12 apart from hydrogen.

(h) for those compounds in which R1 is of the formula VI, reaction of a compound of the formula XXI:

[Formula XXI]

with a compound of the formula H$_2$N—O—R12.

(i) for those compounds in which R1 is of the formula VI in which R11 is 2-aminothiazol-4-yl, reaction of a compound of the formula XXII:

[Formula XXII]

in which R53 is chlorine or bromine, with thiourea.

When the compound of the formula I is obtained in the form of the free base or the zwitterion, and a salt is required, the compound of the formula I in the free base or zwitterionic form is reacted with an acid which affords a pharmaceutically-acceptable anion, or when a compound of the formula I carries carboxy, with a base which affords a pharmaceutically-acceptable cation.

The compound of the formula XIX, and the acid-addition salts thereof, is a valuable intermediate for preparing many of the compounds of the invention. This compound is therefore provided as a further feature of the invention. It may be prepared by reaction of a 3-aminomethyl-7-aminocephalosporin derivative (in which the 7-amino group may optionally be protected) in a process similar to that described in (a) above (followed if necessary by removal of the protecting group). This process is illustrated in Examples 12, 13, 56 and the last two parts of Examples 68–80.

The starting material of the formula XVIII for use in process (a) may be prepared by reaction of a 7-amino-3-azidomethylcephalosporin derivative (in which when R3 is carboxy it is optionally protected) with an acid (or a protected or activated derivative thereof) or with 2-fluoroimidazole, according to process (f) or (c) respectively. The 3-azidomethyl group is then reduced to the 3-aminomethyl group, the optional protecting group or groups being removed either before or after this reduction step. This process is illustrated in Examples 1, 23–52, 66–67a, 81–82, 100–103 and 136.

The starting material for use in process (b) may be prepared by carrying out process (a) or (f) using a suitably protected intermediate, to prepare the corresponding starting material. The use of process (a) is illustrated in Examples 17, 19, 22, 36, 45 and 131. The use of process (f) is illustrated in Examples 12, 13, 56, 68–80 and 91–99.

As noted above the cephalosporin derivatives of the invention have antibacterial properties. Thus they are useful antibacterial agents, many of them having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system.

The antibacterial properties of the compounds of the invention may also be demonstrated in conventional mouse protection tests.

Cephalosporin derivatives have generally been found to be relatively non-toxic to warm-blooded animals, and this generalisation holds true for the compounds of the present invention. A number of compounds were administered to mice at doses in excess of those required to afford protection against bacterial infections. Thus for example the compounds of Examples 23, 70 and 74 were administered subcutaneously to mice in two single doses over one day, each dose being at least five times the minimum effective dose which protected 50% of the mice against infection with Salmonella dublin ($PD_{50}$). No overt toxic symptoms or side effects attributable to the administered compounds were noted.

The results set out in the following Table are illustrative of the biological activity of the compounds of the present invention. The listed compounds all carry a 1-methyl-4-pyridinioaminomethyl radical at the 3-position of the cephalosporin nucleus and a variety of known substituents at the 7-position. The following results are those obtained on a standard in vitro test system using Isosensitest agar medium. The antibacterial activity is described in terms of the minimum inhibitory concentration (MIC) determined by agar-dilution technique with an inoculum size of $10^4$ CFU./spot.

tion may also contain, or be co-administered with, one or more known drugs selected from other clinically useful antibacterial agents (for example other β-lactams or aminoglycoside ), inhibitors of β-lactamase (for example clavulanic acid), renal tubular blocking agents (e.g. proenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 10% w/w of the cephalosporin derivative, or one suitable for oral administration in unit dosage form, for example a tablet or capsule which contains between 100 mg. and 1 g. of the cephalosporin derivative.

The pharmaceutical composition of the invention will normally be administered to man in order to combat infections caused by bacteria, in the same general manner as that employed for cephalothin, cefoxitin, cephradine and other known clinically used cephalosporin derivatives, due allowance being made in in terms of dose levels for the potency of the cephalosporin derivative of the present invention relative to the known clinically used cephalosporins. Thus each patient will receive a daily intravenous, subcutaneous or intramuscular dose of 0.5 to 50 g., and preferably 0.5 to 10 g., of the cephalosporin derivative, the composition being administered 1 to 4 times per day. The intravenous, subcutaneous and intramuscular dose will be given by means of a bolus injection. Alternatively the intravenous dose may be given by continuous infusion over a period of time. Alternatively each patient will receive a daily oral dose which is approximately equiva-

| Organism | Code | MIC ug/ml Example | | | | | | |
|---|---|---|---|---|---|---|---|---|
| | | 9 | 70 | 96 | 23 | 74 | 81 | 82 |
| Strep. pyogenes | A8681018 | 0.016 | <0.016 | — | 0.13 | 0.25 | 0.13 | 0.5 |
| Staph. aureus | A8601052 | 1 | 1 | 0.5 | 8 | 8 | 1 | 2 |
| E. coli | A8341098 | 0.032 | 0.25 | 0.032 | 0.13 | 0.25 | 2 | 128 |
| Sal. dublin | A8369001 | 0.25 | 0.5 | 0.064 | 0.25 | 0.13 | 8 | 64 |
| Kleb. aerogenes | A8391027 | 0.032 | 0.13 | <0.016 | 0.13 | 0.5 | 2 | 64 |
| Ent. cloacae | A8401054 | 0.064 | 1 | 0.25 | 0.5 | 1 | 4 | >128 |
| Serr. marcescens | A8421020 | 0.13 | 0.5 | 0.032 | 0.25 | 1 | 8 | >128 |
| Prot. mirabilis | A8432057 | 0.064 | 0.5 | 0.064 | 0.064 | 0.13 | 32 | 32 |
| P. aeruginosa | A8101028 | 16 | 32 | 32 | 2 | 4 | >128 | >12 |

According to a further feature of the invention there is provided a pharmaceutical composition which comprises a cephalosporin derivative of the invention in association with a non-toxic pharmaceutically-acceptable diluent or carrier.

The pharmaceutical composition of the invention may, for example be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the cephalosporin derivative of the formula I the pharmaceutical composition of the invenlent to the daily parenteral dose. Thus a preferred daily oral dose is 0.5 to 10 g. of the cephalosporin derivative, the composition being administered 1 to 4 times per day.

The invention is illustrated, but not limited, by the following Examples. The n.m.r. spectra are quoted in δ relative to tetramethylsilane (δ=0) as internal standard, (s=singlet, d=doublet, t=triplet, m=multiplet, br=broad). The n.m.r.s are measured at a field strength of 90 or 400 MHz. The n.m.r. solvents are as follows:
Solvent A: $d_6DMSO+CD_3COOD$
Solvent B: $d_6DMSO+CD_3COOD+CF_3COOD$
Solvent C: $CDCl_3+CD_3COOD$
Solvent D: $d_6DMSO+D_2O$ Solvent E: d$_6$DMSO+TFA
Solvent F: d$_6$DMSO+CF$_3$COOD
The temperatures are in degrees Centigrade. The following contractions are used:
TFA=trifluoroacetic acid
THF=tetrahydrofuran
HOAc=acetic acid
EtOAc=ethyl acetate
MeOH=methanol
DMF=dimethylformamide
DMSO=dimethylsulphoxide
ether=diethyl ether
HPLC=high pressure liquid chromatography In the examples the cephalosporin derivative of the invention is isolated in the form of a salt, either an internal salt (a zwitterion) or a salt with an acid such as HBr or CF$_3$COOH. The actual salt which is isolated is dependent on a number of factors including the basicity of the product, the reaction work-up and purification conditions used and the nature of the starting material (salt or free base).

EXAMPLE 1

To a solution of 3-aminomethyl-7-(imidazol-2-yl)aminoceph-3-em-4-carboxylic acid as its TFA/toluene-p-sulphonate salt (1.046 g.) in DMF (15 ml.) was added with stirring at 0° triethylamine (560 ml.) then (ethoxymethylene)ammonium chloride (330 mg.). After 1 hour at 0° a few drops of TFA were added and the mixture evaporated to dryness. MeOH was added to the residue and the resulting precipitate was washed with MeOH then ether and dried under nitrogen. The solid was purified by HPLC using MeOH/aqueous ammonium carbonate 20:80 v/v as eluant (rate 2.5 ml./minute). The relevant fractions were combined and evaporated, and the residue washed with MeOH and ether under nitrogen. There was thus obtained 3-amidinomethyl-7-(imidazol-2-yl)aminoceph-3-em-4-carboxylic acid trifluoroacetate/toluene-p-sulphonate (6%) having the following n.m.r. in solvent A: 3.45 (m, 2H); 4.5 (m, 2H); 5.05 (br s, 1H); 5.55 (br s, 1H); 6.9 (s, 2H); 8.0 (m, 1H).

The starting material may be obtained as follows:
To a stirred suspension of 3-acetoxymethyl-7-aminoceph-3-em-4-carboxylic acid (45.3 g.) in a phosphate buffer (pH 6.4; 700 ml.) was added sodium azide (10.8 g.), then in small portions sodium bicarbonate (14 g.). The stirred mixture was then immersed in a 60° bath for 6 hours, the pH being maintained at 6.4 by addition of 2N aqueous HCl or 5% w/v aqueous sodium bicarbonate solutions. After cooling the pH of the mixture was adjusted to 3–3.5 with 2N aqueous HCl. The resulting precipitate was separated, washed with water and acetone then dried over P$_2$O$_5$ to give 7-amino-3-azidomethylceph-3-em-4-carboxylic acid (40%).

To a suspension of 7-amino-3-azidomethylceph-3-em-4-carboxylic acid (17 g.) in acetonitrile/MeOH (150 ml, 150 ml.) was added diphenyldiazomethane (15.5 g.) in acetonitrile (50 ml.). The mixture was stirred for 2 hours at 40°, then for 18 hours at ambient temperature. The mixture was filtered, the filtrate evaporated to dryness and the residue purified by chromatography on fine mesh silica using methylene chloride/ether 90:10 v/v as eluant. There was thus obtained diphenylmethyl 7-amino-3-azidomethylceph-3-em-4-carboxylate (78%) having the following n.m.r. in CDCl$_3$: 1.75 (s, 2H); 3.5 (s, 2H); 3.95 (d, 1H); 4.3 (d, 1H); 4.8 (d, 1H); 5.0 (d, 1H); 7.0 (s, 1H); 7.4 (s, 10H).

A mixture of diphenylmethyl 7-amino-3-azidomethylceph-3-em-4-carboxylate (1.2 g.), 2-fluoroimidazole hydrochloride (367 mg.) and acetonitrile (4 ml.) was stirred at 85°. When a complete solution was achieved DMF (1 ml.) was added. After 2 hours the solvent waas evaporated and the residue, after drying overnight, was purified by chromatography on fine mesh silica (ratio 40:1 w/w) at 0° using methylene chloride/MeOH/HOAc 100:0:0 to 92:4:4 v/v/v as eluant. The oil obtained was dissolved in the minimum of methylene chloride and precipitated with ether. After drying there was obtained diphenylmethyl 3-azidomethyl-7-(imidazol-2-yl)aminoceph-3-em-4-carboxylate hydrochloride (38%) as a white powder having the following n.m.r. in solent A: 3.65 (d, 1H); 3.8 (d, 1H); 3.95 (d, 1H); 4.3 (d, 1H); 5.3 (d, 1H); 5.85 (d, 1H); 6.9 (s, 2H); 7.0 (s, 1H); 7.5–7.7 (m, 10H).

A mixture of diphenylmethyl 3-azidomethyl-7-(imidazol-2-yl)aminoceph-3-em-4-carboxylate (260 mg.), anisole (1 ml.) and TFA (1 ml.) was stirred at ambient temperature for 30 minutes, and then evaporated to dryness. The residue was dissolved in the minimum methylene chloride/MeOH and precipitated with ether to give, after drying, 3-azidomethyl-7-(imidazol-2-yl)aminoceph-3-em-4-carboxylic acid trifluoroacetate (76%) having the following n.m.r. in solvent A: 3.55 (d, 1H); 3.75 (d, 1H); 4.0 (d, 1H); 4.5 (d, 1H); 5.25 (d, 1H); 5.75 (d, 1H); 7.0 (s, 2H). The n.m.r. indicated that 20% of the delta-2 isomer was present.

A stirred solution of 3-azidomethyl-7-(imidazol-2-yl)aminoceph-3-em-4-carboxylic acid trifluoroacetate (160 mg.) in EtOH/TFA (10 ml, 1 ml.) was hydrogenated over 10% w/w palladium-on-carbon at ambient temperature and pressure. After two hours the mixture was filtered through a pad of diatomaceous earth and the pad washed with methylene chloride/MeOH/HOAc 90:5:5 v/v/v (250 ml.). The combined filtrates were evaporated to dryness and the residue dissolved in the minimum methylene chloride/MeOH and re-precipitated with ether. The precipitate was filtered and dried under nitrogen to give 3-aminomethyl-7-(imidazol-2-yl)aminoceph-3-em-4-carboxylic acid ditrifluoroacetate as a hygroscopic solid (45%) having the following n.m.r. in solvent A: 3.2–3.8 (m, 4H); 5.05 (d, 1H); 5.55 (d, 1H); 6.9 (s, 2H). The n.m.r. indicated that 30% of the delta-2 isomer was present.

EXAMPLES 2–4

The general process described in Example 1 was repeated using the appropriate starting materials in place of (ethoxymethylene)ammonium chloride, and the following compounds were thus obtained:

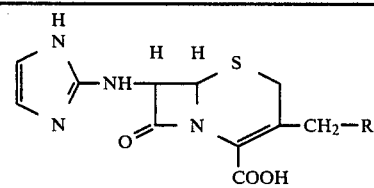

| Example | —R |
|---|---|
| 2 | —NH—\<N / NH — N — \> |

-continued

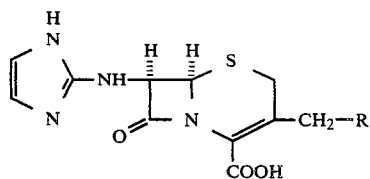

| Example | —R |
|---------|-----|
| 3 | 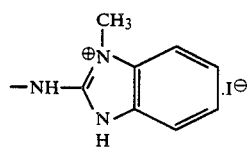 |
| 4 | 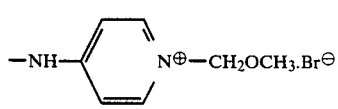 |

Example 2: Process carried out in DMF, first at 0°, then at ambient temperature for 3 hours, using 2-chloroimidazoline as starting material. Product purified by HPLC using MeOH/aqueous ammonium carbonate 15:85 to 25:75 v/v as eluant. Yield of product as TFA/-toluene-p-sulphonate salt 7%. n.m.r. in solvent A: 3.5 (m, 2H); 3.7 (m 4H); 3.95 (s, 2H); 5.1 (d, 1H); 5.6 (d, 1H); 6.9 (s, 2H).

Example 3: Process carried out in MeOH containing one equivalent of triethylamine at 0° for 1 hour using 1-methoxy-3-methylbenzimidazolium iodide as starting material. Reaction mixture worked up by adding TFA, evaporating and purifying residue by HPLC using MeOH/aqueous ammonium carbonate 30:70 v/v as eluant. Yield of product after precipitation from methylene chloride/MeOH with ether 8%. n.m.r. in solvent A: 3.53 (s, 2H); 3.6 (s, 3H); 3.81 (d, 1H); 4.5 (d, 1H); 5.06 (d, 1H); 5.5 (d, 1H); 6.7 (s, 2H); 7.1–7.6 (m, 4H).

Example 4: Process carried out in DMF at ambient temperature for 4 hours using 4-chloro-1-methoxymethylpyrimidinium bromide as starting material. Product twice purified by HPLC using MeOH/HOAc 10:90 to 20:80 v/v as eluant. Yield of product after precipitation from methylene chloride/MeOH with ether 4%. n.m.r. in solvent A: 3.25 (s, 3H); 3.7 (m, 2H); 4.0 (s, 2H); 5.15 (s, 2H); 5.15 (d, 1H); 5.65 (d, 1H); 6.3 (d, 2H); 7.85 (d, 2H); 7.1 (s, 2H).

EXAMPLES 5–11

The general process described in Example 1 was repeated using 3-aminomethyl-7-[2-(2-aminothiazol-4-yl)-2-((Z)-methoxyimino)acetamido]ceph-3-em-4-carboxylic acid trifluoroacetate in place of 3-aminomethyl-7-(imidazol-2-yl)aminoceph-3-em-4-carboxylic acid and the appropriate starting materials in place of (ethoxymethylene)ammonium chloride, and the following compounds were thus obtained:

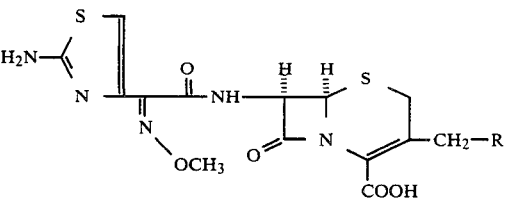

| Example | —R |
|---------|-----|
| 5 | 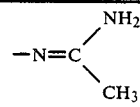 |
| 6 | 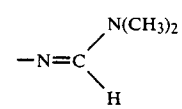 |
| 7 | 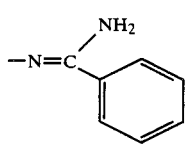 |
| 8 | 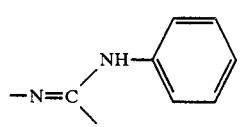 |
| 9 | 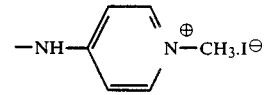 |
| 10 | 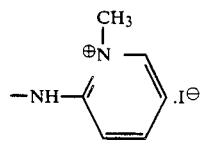 |
| 11 | 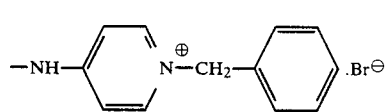 |

Example 5: Process carried out in water at pH 7 for 1 hour at ambient temperature using (1-ethoxyethylidene)ammonium chloride as starting material. Product purified by HPLC using MeOH/water/HOAc 10:90:1 v/v/v as eluant. Yield of product as TFA salt 5%. n.m.r. in solvent E: 2.2 (s, 3H); 3.5 (d, 1H); 3.7 (d, 1H); 4.0 (s, 3H); 4.0–4.4 (m, 2H); 5.2 (d, 1H); 5.9 (d, 1H); 7.1 (s, 1H).

Example 6: Process carried out in DMF at ambient temperature for 1.5 hours using N,N-dimethyl-N-(dimethoxymethyl)amine as starting material. Product purified by HPLC using MeOH/water/HOAc 10:90:1 v/v/v as eluant. Yield of product as TFA salt 6%. n.m.r. in solvent A: 2.95 (s, 3H); 3.15 (s, 3H); 3.2–3.6 (m, 2H); 3.8 (s, 3H); 4.0 (d, 1H); 4.3 (d, 1H); 5.0 (d, 1H); 5.6 (d, 1H); 6.7 (s, 1H); 8.3 (s, 1H).

Example 7: Process carried out in DMF in presence of one equivalent of triethylmine at ambient temperature for 2.5 hours using ethyl benzimidate as starting material. Reaction mixture worked up by addition of TFA, evaporation and purification of residue by HPLC using MeOH/water/HOAc 25:75:1 v/v/v as eluant. Yield of product as TFA salt 17%. n.m.r. in solvent A: 3.2 (d, 1H) 3.6 (d, 1H); 3.8 (d, 1H); 3.8 (s, 3H); 3.9 (d, 1H); 4.8 (d, 1H); 5.1 (d, 1H); 5.7 (d, 1H); 6.8 (s, 1H); 7.4–7.9 (m, 5H).

Example 8: Process carried out in DMF in presence of one equivalent of triethylamine at ambient temperature for 1.5 hours using ethyl N-phenylformimidate as starting material. Product purified by HPLC using MeOH/water/HOAc 20:80:1 v/v/v as eluant. Yield of product as TFA salt 13%. n.m.r. in solvent A: 3.2 (d, 1H); 3.6 (d, 1H); 3.8 (s, 3H); 3.8 (d, 1H); 4.7 (d, 1H); 5.1 (d, 1H); 5.7 (d, 1H); 6.7 (s, 1H); 7.2–7.5 (m, 5H); 8.6 (s, 1H).

Example 9: Process carried out in aqueous DMF at ambient temperature in presence of 3 equivalents of sodium bicarbonate for 3 hours using 4-chloro-1-methylpyridinium iodide as starting material. Product purified by HPLC using water/HOAc/MeOH 84:1:15 to 79:1:20 v/v/v as eluant. Yield of product after precipitation from minimum methylene chloride/MeOH solution with ether 20%. n.m. r. in solvent A: 3.4 (d, 1H); 3.7 (d, 1H); 3.9 (s, 3H); 4.0 (s, 3H); 4.4 (br s, 2H); 5.2 (d, 1H); 5.85 (d, 1H); 7.05 (s, 1H); 6.9–7.2 (br, 2H); 8.0–8.5 (br, 2H).

Example 10: Process carried out as in Example 9, but using 2-chloro-1-methylpyridinium iodide as starting material. HPLC eluant water/HOAc/MeOH 89:1:10 v/v/v. Yield 10%. n.m.r. in solvent F: 3.6 (s, 2H); 3.9 (s, 3H); 4.0 (s, 3H); 4.4 (d, 1H); 4.7 (d, 1H); 5.2 (d, 1H); 5.8 (d, 1H); 7.0 (s, 1H); 7.05 (t, 1H); 7.3 (d, 1H); 8.1 (t, 1H); 8.3 (d, 1H).

Example 11: Process carried out as in Example 9, but using 1-benzyl-4-chloropyridinium chloride as starting material. In addition the reaction residue treated with MeOH/TFA, followed by evaporation, before HPLC. HPLC eluant water/HOAc/MeOH 69:1:30 to 64:1:35 v/v/v. Yield 20%. n.m.r. in solvent F: 3.4 (d, 1H); 3.7 (d, 1H); 4.0 (s, 3H); 4.4 (br s, 2H); 5.2 (d, 1H); 5.85 (d, 1H); 5.4 (s, 2H); 7.0 (s, 1H); 7.5 (s, 5H); 7.1, 8.3, 8.5 (d,d,d 4H).

The 3-aminomethyl-7-[2-(2-aminothiazol-4-yl)-2-((Z)-methoxyimino)acetamido]ceph-3-em-4-carboxylic acid trifluoroacetate used as starting material may be prepared as follows:

To a solution of cefotaxime (5.24 g.) in phosphate buffer (pH 6.4, 440 ml.) was added sodium azide (2.86 g.) and sodium iodide (1.65 g.) and the mixture was immersed in a 70° bath with stirring for 4.5 hours. The solvent was evaporated to the point of precipitation and then the pH adjusted to 2.5 with 2N aqueous HCl. The resulting precipitate was collected, washed with water, acetone and. ether and dried over $P_2O_5$ to give 3-azidomethyl-7-[2-(2-aminothiazol-4-yl)-2-((Z)-methoxyimino)acetamido]ceph-3-em-4-carboxylic acid in quantative yield, having the following n.m.r. in solvent A: 3.4 (d, 1H); 3.7 (d, 1H); 3.86 (s, 3H); 3.95 (d, 1H); 4.4 (d, 1H); 5.15 (d, 1H); 5.78 (d, 1H); 6.75 (s, 1H).

To a stirred suspension of Raney nickel (16 g.) in MeOH (13 ml.) at 0° was added a solution of 3-azidomethyl-7-[2-(2-aminothiazol-4-yl)-2-((Z)-methoxyimino)acetamido]ceph-3-em-4-carboxylic acid (2.96 g.) in MeOH/TFA (14 ml., 1.13 ml.). After effervescence ceased the mixture was diluted with MeOH and filtered through paper. The filtrate was evaporated, the residue purified by HPLC using water/HOAc/MeOH 79:1:20 v/v/v as eluant and the product dried over $P_2O_5$ to give 3-aminomethyl-7-[2-(2-aminothiazol-4-yl)-2-((Z)-methoxyimino)acetamido]ceph-3-em-4-carboxylic acid trifluoroacetate (yield 45%) having the following n.m.r. in solvent A: 3.5–4.2 (m, 4H); 3.9 (s, 3H); 5.15 (d, 1H); 5.85 (d, 1H); 6.75 (s, 1H).

EXAMPLE 12

To a stirred suspension of 7-[2-(2-tritylaminothiazol-4-yl)-2-((Z)-1-t-butoxycarbonyl-1-methylethoxyimino)acetamido]-3-(1-benzyl-4-pyridinio)aminomethylceph-3-em-4-carboxylic acid bromide (3.09 g.) in anisole (25 ml.) immersed in an ice bath was added TFA (30 ml.). Stirring was continued at ambient temperature for 1.5 hours and the solvent was evaporated. The residue was precipitated from the minimum methylene chloride/MeOH solution with ether and the precipitate collected under nitrogen and dried. It was then subjected to purification by HPLC on an octadecylsilane column as follows.

1. Eluant MeOH/aqueous ammonium carbonate buffer at pH 6 70:30 v/v.
2. Eluant as in 1 above. Rate 4.5 ml./minute.
3. Eluant MeOH/aqueous ammonium carbonate buffer at pH 7.2 65:35 v/v. Rate 4.5 ml./minute.

There was thus obtained 7-[2-(2-aminothiazol-4-yl)-2-((Z)-1-carboxy-1-methylethoxyimino)acetamido]-3-(1-benzyl-4-pyridinio)aminomethylceph-3-em-4-carboxylic acid bromide (yield 1%) having the following n.m.r. in solvent A: 1.4 (s, 6H); 3.45 (d, 2H); 4.3 (d, 2H); 5.05 (d, 1H); 5.7 (d, 1H); 5.4 (s, 2H); 6.75 (s, 1H); 7.4 (s, 5H); 6.8–7.0 (m, 2H); 8.2–8.4 (m, 2H).

The starting material may be obtained as follows:

To a stirred solution of 7-amino-3-azidomethylceph-3-em-4-carboxylic and (48 g.) and $NaHCO_3$ (15.8 g.) in dioxan (180 ml.) and water (180 ml.) was added bid(O-t-butylcarbonic)anhydride (31 ml.) in dioxan (90 ml.) and stirring was continued for 90 hours. The solvent was evaporated, water and EtOAc was added and the ph adjusted to 2. The mixture was filtered and the filtrate was evaporated to give 3-azidomethyl-7-t-butoxycarbonylamino-ceph-3-em-4-carboxylic acid. n.m.r. in solvent A: 1.4(s, 9H); 3.55(d, 2H); 3.9(d, 1H); 4.45(d, 1H); 5.0 (d, 1H); 5.45(d, 1H)

A solution of this 3-azidomethyl derivative (12 g.) in EtOAc (400 ml.) and TFA (5.2 ml.) was hydrogenated over palladium on carbon 10% w/w (9 g.) for 30 hours at ambient temperature and pressure. The suspension was filtered through diatomaceous earth and the filtrate evaporated. The product was precipitated from a solution of $CH_2Cl_2$/MeOH with ether to give 3-aminomethyl-7-t-butoxycarbonylaminoceph-3-em-4-carboxylic acid; n.m.r. in $d_6DMSO$ 1.4(s, 9H); 3.4–3.8(m, 4H); 4.95(d, 1H); 5.45 (d, 1H):

To a stirred solution of 3-aminomethyl-7-t-butoxycarbonylaminoceph-3-em-4-carboxylic acid (2.785 g.) in water/DMF (40 ml., 140 ml.) at 0° was added sodium bicarbonate (1.26 g.), and then a solution of 1-benzyl-4-chloropyridinium bromide (1.423 g.) in the minimum amount of DMF. Stirring was continued for 18 hours at ambient temperature and then the solvent was evaporated. The residue was purified by chromatography at 0° on silica using methylene chloride/MeOH/HCOOH 100:0:0 to 88:6:6 v/v/v as eluant to give 7-t-butoxycarbonylamino-3-(1-benzyl-4-pyridinio)aminomethylceph-3-em-4-carboxylic acid bromide (yield 70%) having the following n.m.r. in $d_6DMSO+CD_3COOD$: 1.4 (s, 9H);

3.5 (s, 2H); 4.2–4.4 (m, 2H); 4.95 (d, 1H); 5.4 (d, 1H); 5.4 (s, 2H); 7.45 (s, 5H); 7.0–7.3 (m, 2H); 8.2–8.5 (m, 2H).

To a stirred solution of 7-amino-3-(1-benzylpyridinio)aminomethylceph-3-em-4-carboxylic acid bromide (1.84 g.) in methylene chloride (2.5 ml.) was added TFA (2.5 ml.) and the solution stirred at ambient temperature for 1 hour. The solvent was evaporated and the residue precipitated from methylene chloride/MeOH solution with ether to give, after collecting under nitrogen and drying, a quantitative yield of 7-amino-3-(1-benzyl-4-pyridino)aminomethylceph-3-em-4-carboxylic acid bromide having the following n.m.r. in solvent A: 3.6 (s, 2H); 4.4 (brs, 2H); 5.1 (s, 2H); 5.4 (s, 2H); 7.1 (d, 2H); 7.45 (s, 5H); 8.2–8.6 (m, 2H).

To a stirred solution of 7-amino-3-(1-benzyl-4-pyridinio)aminomethylceph-3-em-4-carboxylic acid bromide (296 mg.) in methylene chloride (1.5 ml.) was added N,O-bis(trimethylsilyl)acetamide (310 l.). Stirring was continued for 1 hour at ambient temperature to give a solution of trimethylsilyl 7-trimethylsilylamino-3-(1-benzyl-4-pyridinio)aminomethylceph-3-em-4-carboxylate bromide which was used as such.

To a stirred solution of 2-((Z)-1-t-butoxycarbonyl-1-methylethoxyimino)-2-(2-tritylaminothiazol-4-yl)acetic acid (UK Pat. No. 1,603,989, 285 mg.) in methylene chloride (1.5 ml.) was added N-methylmorpholine (55 l.). To the stirred reaction mixture, cooled to −45°, was added (chloromethylene)dimethylammonium chloride (71 mg.). There was then added, still at −45° and by means of a syringe, the methylene chloride solution of trimethylsilyl 7-trimethylsilylamino-3-(1-benzyl-4-pyridinio)aminomethylceph-3-em-4-carboxylate bromide (403 mg.). The stirred reaction mixture was then allowed to warm to ambient temperature, and the solvent was evaporated to give 7-[2-(2-tritylaminothiazol-4-yl)-2-((Z)-1-t-butoxycarbonyl-1-methylethoxyimino)acetamido]-3-(1-benzyl-4-pyridinio)aminomethylceph-3-em-4-carboxylic acid bromide which was used without further purification.

EXAMPLE 13

The process described in Example 12 was repeated, using 7-[2-(2-tritylaminothiazol-4-yl)-2-((Z)-1-t-butoxycarbonyl-1-methylethoxyimino)acetamido]-3-(3-dimethylamidino)methylceph-3-em-4-carboxylic acid as starting material. The product was purified by HPLC on an octadecylsilane column using MeOH/water/HOAc 20:79:1 v/v/v, rate 4.5 ml./minute, and there was thus obtained 7-[2-(2-aminothiazol-4-yl)-2-((Z)-1-carboxy-1-methylethoxyimino)acetamido]-3-(3-dimethylamidino)methylceph-3-em-4-carboxylic acid trifluoroacetate (yield 10%) having the following n.m.r. in solvent A: 1.4 (s, 6H); 3.05 (d, 6H); 3.4 (s, 2H); 4.0 (d, 1H); 4.3 (d, 1H); 5.0 (d, 1H); 5.7 (d, 1H); 6.7 (s, 1H); 8.3 (s, 1H).

The starting material may be obtained by repeating the fourth, fifth, sixth and seventh parts of Example 12, using N,N-dimethyl-N-(dimethoxymethyl)amine as starting material in place of 1-benzyl-4-chloropyridinium bromide. There was thus obtained a series of intermediates corresponding to those obtained in the second, third, fourth and fifth parts of Example 12, the (3-dimethylamidino)methyl radical replacing the 3-(1-benzyl-4-pyridinio)aminomethyl radical. All these intermediates were characterised by n.m.r.

EXAMPLE 14–15

The general process described in Example 1 was repeated using the appropriate starting materials in place of (ethoxymethylene)ammonium chloride, and the following compounds were thus obtained:

| Example | −R | Yield % |
|---|---|---|
| 14 | −N=C(H)(N-azepanyl) | 32 |
| 15 | −N=C(H)N(CH$_3$)$_2$ | 10 |

Example 14: Process carried out in DMF at 0° using 2,3,4,5,6,7-tetrahydro-1-(methoxymethylene)-1H-azepinium methanesulphonate as starting material. Product purified by HPLC using MeOH/aqueous ammonium carbonate 20:80 v/v as eluant. n.m.r. in solvent A: 1.4–1.8(m, 8H); 3.3–3.7 (m, 4H); 3.55(s, 2H); 4.1(d, 1H); 4.3(d, 1H); 5.0(d, 1H): 5.5(d, 1H); 6.75(s, 2H); 8.3(s, 1H).

Example 15: Process carried out in DMF at 0° using N,N-dimethyl-N-(dimethoxymethyl)amine as starting material. Product purified by HPLC using MeOH/aqueous ammonium carbonate 10:90 v/v as eluant. n.m.r. in solvent A: 3.1(d, 6H); 3.5(s, 2H); 4.35(d, 1H); 4.1 (d, 1H); 5.05(d, 1H); 5.5(d, 1H); 6.8(s, 2H); 8.1(s, 1H).

EXAMPLES 16–22

The general process described in Examples 5–11 was repeated using the same 3-aminomethylcephalosporin derivative and, unless otherwise stated, the appropriate chloroheterocycle as starting materials, the reactions being carried out in DMF/water 2:1 v/v in the presence of 3 equivalents of NaHCO$_3$ at a temperature in the range ambient to 40° and over a period of 1–4 hours. The products were purified by HPLC on an octadecylsilane column, and the following compounds were thus prepared.

[Structure: H₂N-thiazole-C(=NOCH₃)-CONH-β-lactam-CH₂NH-R with COOH]

| Example | —R | Yield % | Footnotes |
|---------|-----|---------|-----------|
| 16 | [bicyclic N⊕—CH₃ cyclopenta-fused pyridinium] | 31 | 1,2,3 |
| 17 | —CH=NH⊕—CH₂COOH | 10 | 4 |
| 18 | [pyridinium N⊕—CH₂COOC₂H₅] | 30 | 1,5,6 |
| 19 | [imidazolium with CH₃ on one N and CH₂COOH on other N⊕] | 20 | 1,7,8,9 |
| 20 | [pyridinium N—CH₂COOH] | 18 | 1,10,11 |
| 21 | —CH=NH⊕—CN | 17 | 12,5,13 |
| 22 | —C(=NH₂⊕)—CH₂COOH | 1 | 14,5,15 |

Footnotes
1. Starting material was the corresponding chloroheterocycle.
2. HPLC eluant MeOH/water/HOAc 25:74:1 v/v/v.
3. n.m.r. in solvent A:-2-3 (m, 6H); 3.5(m, 2H); 3.8(s, 3H); 3.9(s, 3H); 4.4(m, 2H); 5.15(d, 1H); 5.8(d, 1H); 6.9(s, 1H); 6.9(d, 1H); 8.1(d, 1H).
4. Starting material was t-butyl 2-(ethoxymethyleneamino)-acetate. Reaction carried out in DMF with 20% molar triethylamine. The product was purified as in Footnote 2 and treated with TFA for 30 minutes to cleave the t-butyl ester. n.m.r. in solvent A:-3.6(m, 2H); 3.85(s, 3H); 4.05-4.45(m, 4H); 5.15(d, 1H); 5.8(d, 1H); 6.8(s, 1H); 8.1(s, 1H).
5. HPLC eluant MeOH/water/HOAc 20:79:1 v/v/v.
6. n.m.r. in solvent F:-1.24(t, 3H; 3.4(d, 1H); 3.7(d, 1H); 4.0(s, 3H); 4.22(q, 4H); 4.4(s, 2H); 5.2(s, 2H); 5.25(d, 1H); 5.85(d, 1H); 7.0(s, 1H); 7.1-8.3(m, 4H);
7. The starting material was prepared by reaction of 2-chloroimidazole with t-butyl bromoacetate in CH₂Cl₂/aqueous sodium hydroxide in presence of tetra-n-butyl ammonium hydrogen sulphate to give 1-t-butoxycarbonylmethyl-2-chloroimidazole. Reaction of this compound with trimlethyloxonium tetrafluoroborate in CH₂Cl₂ gave 1-t-butoxycarbonylmethyl-2-chloro-3-methylimidazolium tetrafluoroborate; n.m.r. in d₆DMSO:-1.5(s, 9H); 3.9(s, 3H); 5.17(s, 2H); 7.81(d, 1H): 7.85(d, 1H).
8. HPLC eluant MeOH/water/HoAc 13:86:1 v/v/v.
9. n.m.r. in solvent B:-3.68(s, 3H); 3.96(s, 3H); 4.24(m, 2H); 4.86(s, 2H); 5.2(d, 1H); 5.8(d, 1H); 6.94(s, 1H); 7.3(s, 2H)
10. HPLC eluant MeOH/water/HOAc 10:89:1 v/v/v.
11. n.m.r. in solvent F:-3.4(d, 1H); 3.7(d, 1H); 4.0(s, 3H); 4.4(s, 2H); 5.1(s, 2H); 5.22(d, 1H); 5.81(d, 1H); 7.0(s, 1H); 7.1-8.3(m, 4H).
12. Reaction carried out with N-ethoxymethylenecyanamide 2 equivalents, 3-aminomethylcephalosphorin 1 equivalent and triethylamine 1 equivalent in DMF.
13. n.m.r. in solvent A:-3.5(d, 1H); 3.6(d, 1H); 3.92(s, 3H); 4.0(d, 1H); 4.4(d, 1H); 5.05(d, 1H); 5.8(d, 1H); 6.8(s, 1H); 8.3(s, 1H).
14. Reaction carried out with t-butyl cyanoacetate 3 equivalents and 3-aminomethylcephalosporin 1 equivalent and a catalytic amount of TFA in DMF for 7 hours at 60°.
15. m.m.r. in solvent A:-3.6(d, 1H); 3.8(d, 1H); 3.9(s, 3H); 4.0(m, 2H); 5.1(d, 1H); 5.9(d, 1H); 6.8(s, 1H).

EXAMPLES 23–52

The general process described in Examples 5–11 was repeated using 3-aminomethyl-7-[2-(2-aminothiazol-4-yl)-2-((Z)-1-carboxy-1-methylethoxyimino)-acetamino]ceph-3-em-4-carboxylic acid as the 3-aminomethylcephalosporin derivative and the appropriate quaternised heterocyclic starting materials, the reactions being carried out in DMF/water 5:2 v/v in the presence of 2–4 equivalents of NaHCO₃ at a temperature in the range ambient to 45° for 1–4 hours. The product was purified on an octadecylsilane HPLC column, and the following compounds were thus prepared.

[Structure: H₂N-thiazole-C(=N-O-C(CH₃)₂-COOH)-CO-NH-β-lactam-CH₂NH-R with COO⁻]

| Example | —R | Yield % | Footnotes |
|---------|-----|---------|-----------|
| 23 | [pyridinium N⊕=CH₃] | 8 | 1,2,3 |
| 24 | [pyridinium N⊕=CH₂SCH₃] | 30 | 1,4,5,6 |

-continued
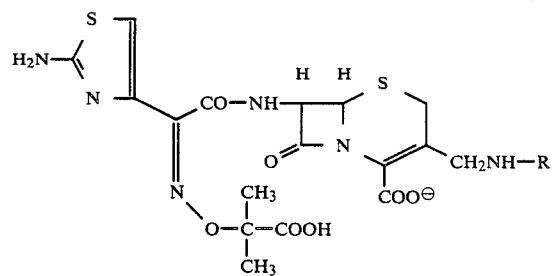
| Example | —R | Yield % | Footnotes |
|---|---|---|---|
| 25 | 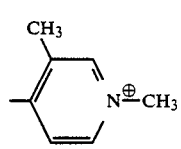 | 50 | 1,7,8 |
| 26 | 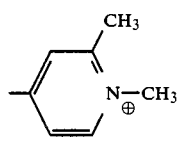 | 58 | 1,7,9 |
| 27 | 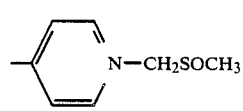 | 22 | 10 |
| 28 | 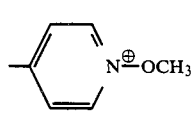 | 20 | 1,2,11 |
| 29 | 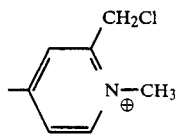 | 8 | 12,13,14 |
| 30 | 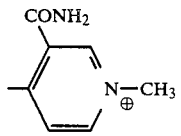 | 26 | 15,13,16 |
| 31 | 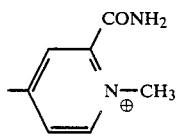 | 15 | 17,13,18 |
| 32 | 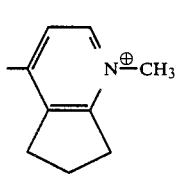 | 24 | 19,20,21 |
| 33 | 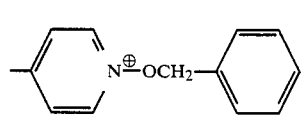 | 20 | 22,23 |
-continued
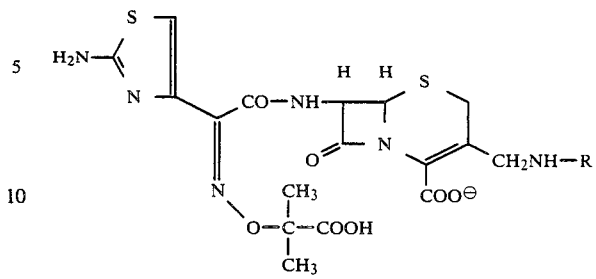
| Example | —R | Yield % | Footnotes |
|---|---|---|---|
| 34 | 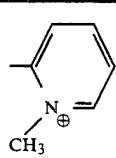 | 28 | 7,24 |
| 35 | 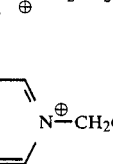 | 33 | 25,26,27 |
| 36 | 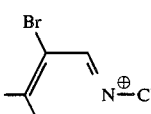 | 100 | 28,29 |
| 37 | 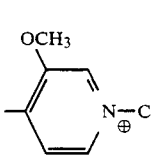 | 30 | 30,31,32 |
| 38 | 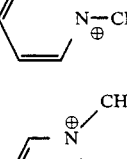 | 17 | 33,31,34 |
| 39 | 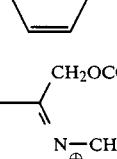 | 15 | 35,7,36 |
| 40 | 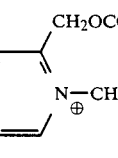 | 37 | 37,7,38 |
| 41 | 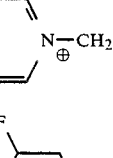 | 30 | 39,40,41 |
| 42 | 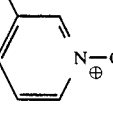 | 38 | 42,7,43 |

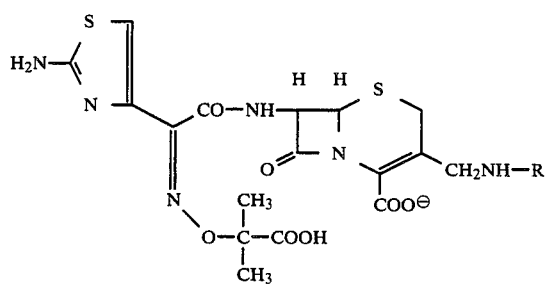

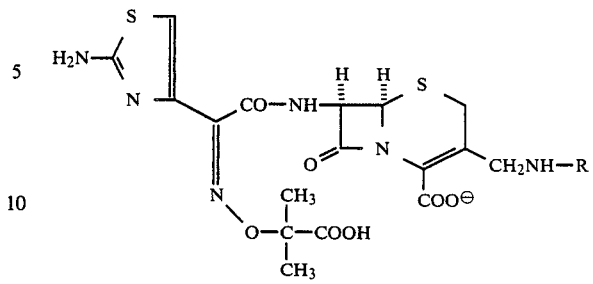

| Example | —R | Yield % | Footnotes |
|---|---|---|---|
| 43 | [4-amino-1-methylpyridinium, NH2 at 2-position] | 11 | 44,31,45,46 |
| 44 | [3-amino-1-methylpyridinium] | 11 | 47,45,7,48 |
| 45 | [2-(CH2SCH2CH2NH2)-1-methylpyridinium] | 15 | 49,50,22,51 |
| 46 | [2-(CH2NHCOCH3)-1-methylpyridinium] | 30 | 52,13,53 |
| 47 | [2-(CH2NH2)-1-methylpyridinium] | 22 | 54,55,56,57 |
| 48 | [1-(CH2CH2OH)pyridinium] | 50 | 58,59,60 |
| 49 | [1-(CH2COCH3)pyridinium] | 16 | 61,59,62 |
| 50 | [1-(CH2COCH3)pyridinium] | 100 | 63 |
| 51 | [1-(CH2CH2N(CH3)2)pyridinium] | 33 | 64,56,65 |
| 52 | [1-(CH2CH2NHCOCH3)pyridinium] | 53 | 66,59,67 |

Footnotes

1. Starting material was the corresponding chloroheterocycle.

2. HPLC eluant MeOH/water/HOAc 20-25:79-74:1 v/v/v.

3. n.m.r. in solvent F:-1.5(s, 6H); 3.4(d, 1H); 3.2(d, 1H); 3.9(s, 3H); 4.4(s, 2H); 5.2(d, 1H); 5.85(d, 1H) 7.1(s, 1H); 6.9-8.3(m, 4H).

4. The chloropyridium salt was obtained by reaction of 4-trimethylsilyloxypyridine with chloromethyl methyl sulphide (no solvent). After extraction and washing with ether the product was treated in chloroform with oxalyl chloride at 60° for 8 hours. The resulting 4-chloro-1-methylthiomethylpyridinium chloride had the following n.m.r. in solvent A:-2.2(s, 3H); 5.85(s, 2H); 8.4(d, 2H); 9.26(d, 2H).

5. HPLC eluant MeOH/water/HOAc 28:71:1 v/v/v.

6. n.m.r. in solvent A:-1.56(s, 6H); 2.12(s, 3H); 3.42(d, 1H); 3.7(d, 1H); 4.4(s, 2H); 5.22(d, 1H); 5.9(d, 1H); 5.34(s, 2H); 7.04(s, 1H); 6.9-7.2(m, 2H); 8.2-8.6(m, 2H).

7. HPLC eluant MeOH/water/HOAc 25:74:1 v/v/v.

8. n.m.r. in solvent A:-1.5(s, 6H); 2.2(s, 3H); 3.3(d, 1H); 3.5(d, 1H); 3.9(s, 3H); 4.3(d, 1H); 4.5(d, 1H); 5.1(d, 1H) 5.7(d, 1H); 6.8(s, 1H); 7.4(d, 1H); 8.1-8.3(m, 2H).

9. n.m.r. in solvent B:-1.6(s, 6H); 2.5(s, 3H); 3.4(d, 1H); 3.7(d, 1H); 3.8(s, 3H); 4.35(m, 2H); 5.2(d, 1H); 5.9(d, 1H); 7.1(s, 1H); 6.8-7.1(m, 2H); 8.1-8.3(m, 1H).

10. The product of Example 24 was oxidised with metachloroperbenaoic acid in $CH_2Cl_2$ at 0° for 3 hours. The product was isolated by precipitation with ether. n.m.r. in solvent A:-1.48(s, 6H); 2.56(s, 3H); 3.32(d, 1H); 3.62(d, 1H); 4.24(d, 1H); 4.52(d, 1H); 5.08(d, 1H); 5.76(d, 1H); 5.24(d, 1H); 5.56(d, 1H); 6.78(s, 1H); 6.9-8.3 (m, 4H).

11. n.m.r. in solvent A:-1.52(s, 6H); 3.2-3.8(m, 2H); 4.2(s, 3H); 4.24(d, 1H); 4.52(d, 1H); 5.1(d, 1H); 5.78(d, 1H); 6.8(s, 1H).

12. The 4-chloropyridinium salt was obtained by reaction of 4-chloro-2-chloromethylpyridine with 2 equivalents of dimethyl sulphate for 6 hours. The crude reaction mixture was washed with ether and dried. n.m.r. in solvent B:-3.5(s, 3H); 4.44(s, 3H); 5.28(s, 2H); 8.32(dd, 1H); 8.54(d, 1H); 9.16(d, 1H).

13. HPLC eluant MeOH/water/HOAc 20:79:1 v/v.v.

14. n.m.r. in solvent B:-1.54(s, 6H); 3.4–3.7(m, 2H); 3.95(s, 3H); 4.38(s, 2H); 5.0(s, 2H); 5.27(d, 1H); 5.9(d, 1H); 7.0(s, 1H); 6.8–7.4(m, 2H); 8.0–8.6(m, 2H).

15. The starting material, 3-carbamoyl-1-methyl-4-methoxypyridinium sulphate, was obtained by reaction of 3-carbamoyl-4-methoxypyridine with a 50% excess of dimethylsulphate in MeOH at ambient temperature for 18 hours. The solvent was evaporated and the residue triturated with ether. m.m.r. in $D_2O$:-3.8(s, 3H); 4.1(s, 3H); 7.7(d, 1H); 8.8(d, 1H); 9.1(s, 1H).

16. n.m.r. in solvent A:-1.45(s, 6H); 3.3(d, 1H); 3.5(d, 1H); 3.9(s, 3H); 4.3(d, 1H); 4.5(d, 1H); 5.1(d, 1H); 5.7(d, 1H); 6.8(s, 1H); 7.6(d, 1H); 8.2(d, 1H); 8.75(s, 1H).

17. The starting material, 2-carbamoyl-1-methyl-4-methoxypyridinium sulphate, was obtained as follows. 2-carbamoyl-4-methoxypyridine-N-oxide was reduced with Raney nickel in MeOH at ambient temperature in the presence od hydrogen, and the product, 2-carbamoyl-4-methoxypyridine, recrystallised from acetone. This product was reacted with dimethylsulphate (no solvent) at 60° for one hour. The crystalline salt was separated from the cooled reation mixture and washed with ether. n.m.r. in $D_2O$:-3.8(s, 3H); 4.16(s, 3H); 4.2(s, 3H); 7.4–7.6(m, 1H); 7.7(d, 1H); 8.7(d, 1H);

18. n.m.r. in solvent B:-1.55(s, 6H); 3.4(d, 1H); 3.6(d, 1H); 3.9(s, 3H); 4.3(d, 1H); 4.5(d, 1H); 5.2(d, 1H); 5.9(d, 1H); 7.1(s, 1H); 6.9–7.3(m, 2H); 8.1–8.4(m, 2H).

19. The starting material, 2,3-cyclopentano-4-chloro-1-methylpyridinium iodide were prepared as follows. Streams of chlorine and and $SO_2$ were bubbled through a solution of 2,3-cyclopentanopyridine-N-oxide in chloroform for 4 hours. The solvent was evaporated, water added and the pH adjusted to 8. The mixture was steam distilled aand the organic product distilled to give 2,3-cyclopentano-4-chloropyridine. This compound was treated with excess methyliodide (no solvent) at 0°. The crystalline product was washed with ether. n.m.r. in $D_2O$:-2.2–2.6(m, 2H); 3.2–3.5(m, 4H); 4.2(s, 3H); 7.85(d, 1H); 8.46(d, 1H).

20. HPLC eluant MeOH/water/HOAc 30:69:1 v/v/v.

21. n.m.r. in solvent B:-1.5(s, 6H); 2.0;14 3.2(m, 6H); 3.5(m, 2H); 4.5(m, 2H); 5.2(d, 1H); 5.9(d, 1H); 7.0(s, 1H) 7.0(d, 1H); 8.1(d, 1H).

22. HPLC eluant MeOH/aqueous ammonium carbonate (2 g./l) 35:65 v/v.

23. n.m.r. in solvent B:-1.51(s, 6H); 3.2–3.8(m, 2H); 4.36(s, 2H); 5.22(d, 1H); 5.9(d, 1H); 5.42(s, 2H); 6.93(s, 1H) 7.47(s, 5H); 7.0–7.1, 7.3–7.5, 8.3–8.8 (m, m, m, 4H).

24. n.m.r. in solvent B:-1.6(s, 6H); 3.5(n, 2H); 3.9(s, 3H); 4.5(d, 1H); 4.7(d, 1H); 5.2(d, 1H); 5.9(d, 1H); 7.05(s, 1H); 6.9–7.5(m, 2H); 8.0–8.4(m, 2H).

25. The starting material, 4-chloro-1-[2-(t-butoxycarbonyl-amino)ethyl]pyridinium toluene-p-sulphonate, was obtained as follows: 4-Pyridone, N-t-butoxycarbonyl-2-methanesulphonyoxylethylamine and potassium carbonate in acetone were heated at reflux for 15 hours. The filtered mixture was purified by silica gel chromatography to give 1-[2-(t-butoxycarbonylamino)ethyl]-4-pyridone as a crystalline solid. This was reacted with toluene-p-sulphonyl chloride in toluene at reflux. The oil which separated was washed with ether and dried. n.m.r. in solvent B:-1.27(s, 9H); 2.3(s, 3H); 3.3–3.7(m, 2H); 4.6(t, 2H); 7.12(d, 2H); 7.51(d, 2H) 8.4(d, 2H); 9.05(d, 2H).

26. HPLC eluant MeOH/water/HOAc 35–40; 64–59:1 v/v/v.

27. n.m.r. in solvent A:-1.3(s, 9H); 1.52(s, 6H); 3.2–3.6 (m, 4H); 4.0–4.4(m, 4H); 5.2(d, 1H); 5.88(d, 1H); 6.95(s, 1H); 6.8–7.2(m, 2H); 8.0–8.4(m, 2H).

28. Product obtained by reactions of product of Example 35 with methylene chloride/TFA 50:50 v/v for 30 minutes. The solvent was evaporated, the residue dissolved in MeOH and the product precipitated with ether.

29. n.m.r. in solvent B:-1.54(s, 6H); 3.2–3.7(m, 4H); 4.1–4.6 (m, 4H); 5.2(d, 1H); 5.88(d, 1H) 7.0(s, 1H); 6.8–7.3(m, 2H); 8.0–8.4(m, 2H).

30. The starting material 3-bromo-4-chloro-1-methyl-pyridinium iodide was obtained by reaction of 3-bromo-4-chloropyridine in a minimum MeOH with a large excess of methyl iodide at ambient temperature for 18 hours. The resulting oil was triturated with ether to give a solid. n.m.r. in $d_6$LDMSO:-4.35(s, 3H); 8.55(d, 1H); 9.1(d, 1H); 9.6(s, 1H).

31. HPLC eluant MeOH/water/HOAc 30:69:1 v/v.v.

32. n.m.r. in solvent B:-1.6(s, 6H); 3.5(m, 2H); 4.6(m, 2H); 4.2(d, 1H); 4.9(d, 1H); 7.1(s, 1H); 7.3(d, 1H); 8.4(d, 1H); 8.8(d, 1H).

33. The starting material was obtained as follows: Hydrogen was bubbled through a mixture of 4-chloro-3-methoxypyridine-N-oxide and Raney nickel in MeOH for 3 hours. The solvent was evaporated to give 4-chloro-3-methoxypyridine. A mixture of this product, MeOH and a large excess of methyl iodide was allowed to stand at ambient temperature for 18 hours. The solvent was evaporated and the residue triturated with ether to give 4-chloro-3-methoxy-1-methylpyridinium iodide. n.m.r. in solvent F:-4.05(s, 3H); 4.3(s, 3H); 8.3(d, 1H); 8.6(d, 1H); 9.0(s, 1H).

34. n.m.r. in solvent B:-1.6(s, 6H); 3.5(m, 2H); 4.0(s, 3H); 4.5(m, 2H); 5.2(d, 1H); 5.9(d, 1H); 7.1(s, 1H); 7.1(m, 1H); 8.1(m, 2H).

35. Starting material was 3-fluoro-1-methyl-pyridinium iodide and the reaction mixture was heated for 7 hours at 40°.

36. n.m.r. in solvent B:-1.6(s, 6H); 3.5–3.7(m, 2H); 4.25(s, 3H); 4.2(m, 2H); 5.2(d, 1H); 5.9(d, 1H); 7.1(s, 1H); 7.6–7.8(m, 2H); 8.1–8.3(m, 2H).

37. The starting material was obtained as follows: A mixture of 4-chloro-2-chloromethylpyridine and sodium acetate in DMF/water was heated at 50° for 18 hours. The solvent was evaporated and the residue extracted from water with EtOAc. The extracted material was purified by silica gel chromatography. This product was treated with 10% excess dimethyl sulphate in methylene chloride. The amide product was washed with water to give 2-actoxymethyl-4-chloro-1-methylpyridinium methyl sulphate. n.m.r. in solvent A:-2.13(s, 3H); 3.4(s, 3H); 4.28(s, 3H); 5.5(s, 2H); 8.3(dd, 1H); 9.1(d, 1H).

38. n.m.r. in solvent A:-1.47(s, 6H); 2.17(s, 3H); 3.2–3.6(m, 2H); 3.88(s, 3H); 4.2–4.7(m, 2H); 5.1(d, 1H); 5.78(d, 1H); 6.76(s, 1H); 6.9–7.1, 7.2–7.5, 8.0–8.4(m, m, m, 4H).

39. The starting material was obtained as follows:-A mixture of 4-methylthiopyridine and bromoacetamide in $CH_2Cl_2$ was allowed to stand at ambient temperature for 18 hours. The resulting precipitate was washed with ether, dried and oxidised with metachloroperbenzoic acid in methylene chloride/TFA at ambient temperature. The solvent was evaporated and the residue was washed with ether to give a mixture of 1-carbamoylmethyl-4-methanesulphinylpyridinium bromide and 1-carbamoylmethyl-4-methanesulphonylpyridinium bromide. n.m.r. in solvent B:-3.56(s, 3H); 5.58(s, 2H); 8.74(d, 2H); 9.38(d, 2H).

40. HPLC eluant MeOH/water/HOAc 15:84:1 v/v/v.

41. n.m.r. in solvent A:-1.47(s, 6H); 3.32(d, 1H); 3.6(d, 1H); 4.2(d, 1H); 4.52(d, 1H); 4.86(s, 2H); 5.06(d, 1H); 5.76(d, 1H); 6.75(s, 1H); 6.8–7.1, 7.2–7.5, 7.9–8.3 (m, m, m, 4H).

42. The starting material was obtained by reaction of 4-chloro-3-fluoropyridine with an excess of methyl iodide (no solvent) at 0° for 5 days. The crystalline product was washed with ether and dried to give 4-chloro-3-fluoro-1-methylpyridinium iodide, n.m.r. in solvent A:-4.4(s, 3H); 8.6(d, 1H); 9.0(d, 1H); 9.6(d, 1H).

43. n.m.r. in solvent B:-1.6(s, 6H); 3.6(m, 2H); 4.0(s, 3H); 4.5(m, 2H); 5.2(d, 1H); 5.9(d, 1H); 7.05(s, 1H); 7.2–7.4 (m, 1H); 8.2–8.4(m, 1H); 8.6–8.8(m, 1H).

44. The starting material was obtained by allowing a mixture of 2-amino-4-chloropyridine and excess methyl iodide (no solvent) to stand at ambient temperature for 2 days to give 2-amino-4-chloro-1-methylpyridinium iodide as a solid, n.m.r. in $d_6$DMSO:-3.6(s, 3H); 6.6–6.7(m, 1H); 7.0(d, 1H); 7.9(d, 1H).

45. The reaction mixture was heated at 40° for 20 hours.

46. n.m.r. in solvent B:-1.6(s, 6H); 3.6(m, 2H); 4.2–4.3(m, 2H); 5.2(d, 1H); 5.9(d, 1H); 5.9–6.0(m, 1H); 6.3–7.5(m, 1H); 7.6–7.8(m, 1H).

47. The starting material was prepared by allowing a mixture of 3-amino-4-chloropyridine and excess methyl iodide (no solvent) to stand at ambient temperature for 1 hour to give 3-amino-4-chloro-1-methylpyridinium iodide as a solid, n.m.r. in solvent F:-4.2(s, 3H); 7.9–8.3(m, 3H).

48. n.m.r. in solventB:-1.6(s, 6H); 3.6(m, 2H); 4.4(m, 2H); 3.9(s, 3H); 5.2(d, 1H); 5.9(d, 1H); 6.8–7.0(d, 1H); 7.6(s, 1H); 7.8–8.0(d, 1H).

49. The starting material was prepared as follows:-A mixture of 4-chloro-2-chloromethylpyridine, 2-butoxycarbonylamino)ethanethiol and sodium bicarbonate in DMF/dioxan/water 1:1:1 v/v/v was allowed to stand at ambient temperature for 24 hours. The product was purified by silica gel chromatography and treated with one equivalent of dimethyl sulphate at ambient temperature for 2 hours. There was thus obtained 4-chloro-1-methyl-2-[2-(t-butoxycarbonylamino)ethylthiomethyl]-pyridinium methyl sulphate. n.m.r. in CDCL$_3$:-1.48(s, 9H); 2.72(t, 2H); 3.3(m, 2H); 3.68(s, 3H); 4.28(s, 2H); 4.5(s, 3H); 7.9(dd, 1H); 8.26(d, 1H); 9.14(d, 1H).

50. At the end of the reaction the solvent was evaporated and the residue trested with TFA for 30 minutes.

51. n.m.r. in solvent B:-1.48(s, 6H); 2.72(m, 2H); 3.04(m, 2H); 3.52(m, 2H); 3.88(s, 3H); 4.0(m, 2H); 4.3(m, 2H); 5.14(d, 1H); 5.84(d, 1H); 6.94(s, 1H); 7.0(m, 2H); 8.0(m, 1H).

52. The starting material may be obtained as follows. Reaction of 2-chloromethyl-4-chloropyridine with excess tetramethylquinoline azide in CH$_2$Cl$_2$ at ambient temperature for 24 hours gave 2-azidomethyl-4-chlorpyridine. n.m.r. in CDCl$_3$:-4.5(s, 2H); 7.3(m, 2H); 8.5(d, 1H). Reduction of this compound in MeOH in the presence of 2 equivalents of acetic anhydride with Raneyl nickel at ambient temperature for 30 minutes gave, after purification by silica gel chromatography, 2-acetylaminomethyl-4-chloropyridine, n.m.r. in CDCl$_3$:-2.1(s, 3H); 4.56(d, 2H); 7.3(m, 2H); 8.48(d, 2H). Reaction of the compound with excess dimethyl sulphate for 30 minutes at 40° gave 2-acetylaminomethyl-4-chloro-1-methylpyridinium methyl sulphate, n.m.r. in solvent F:-2.0(s, 3H); 3.44(s, 3H9; 4.3(s, 3H); 4.7(s, 2H); 8.2(m, 2H); 9.04(d, 1H).

53. n.m.r in solvent B:-1.56(s, 6H); 1.98(s, 3H); 3.5(m, 2H); 3.9(s, 3H); 4.4(m, 4H); 5.22(d, 1H); 5.9(d, 2H); 6.9(m, 2H); 7.08(s, 1H); 8.2(m, 1H).

54. The starting material may be obtained as follows: 2-azidomethyl-4-chloropyridine was reduced with Raney nickel in MeOH in the presence of 2 equivalents of bis(O-t-butylcarbonic)anhydride at ambient temperature for one hour. The product was purified by chromatography on silica gel to give 2-t-butoxycarbonylaminomethyl-4-chloropyridine. n.m.r. in CDCl$_3$:-1.46(s, 9H); 4.44(d, 2H); 5.4(m, 1H); 7.3(m, 2H); 8.46(d, 2H). Reaction of this compound with excess dimethyl sulphate at 40° for 1.5 hours gave 2-t-butoxycarbonylaminomethyl-4-chloro-1-methylpyridinium methyl sulphate. n.m.r. in CDCl$_3$:-1.46(s, 9H); 3.6(s, 3H9; 4.36(s, 3H); 4.72(d, 2H); 6.6(m, 1H); 7.9(m, 2H); 9.02(d, 1H).

55. At the end of the reaction the crude product was treated with TFA at ambient temperature for 30 minutes.

56. HPLC eluant MeOH/water/HOAc 5–10:94–89:1 v/v/v.

57. n.m.r. in solvent B:-1.52(s, 6H); 3.5(m, 2H); 3.92(s, 3H); 4.36(s, 4H); 5.2(d, 1H); 5.9(d, 1H); 7.04(m, 2H); 7.06(s, 1H); 8.3(m, 1H).

58. The starting material may be obtained as follows: Reaction of 4-methylthipyridine with 5 equivalents of 2-bromoethanol for 18 hours at 40° gave, after precipitation from ether, 1-(2-hydroxyethyl)-4-methylthiopyridinium bromide. n.m.r. in solvent B:-2.68(s, 3H); 3.8(t, 2H); 4.5(t, 2H); 7.9(d, 2H); 8.68(d, 2H); Oxidation of this compound with metachlorperbenzoic acid in CH$_2$Cl$_2$/TFA at ambient temperature for 3 hours gave a 1:1 mixture of 1-(2-hydroxethyl()-4-methansulphinyl-pyridinium bromide and the corresponding sulphone. n.m.r. in solvent F:-3.0(s, 3H); 3.56(s, 3H); 3.8–4.1(m, 2H); 4.7–5.0(m, 2H); 8.5(d, 2H); 8.72(d, 2H); 9.24(d, 2H); 9.44(d, 2H).

59. HPLC eluant MeOH/water/HOAc 15–20; 84–79:1 v/v/v.

60. n.m.r. in solvent B:1.54(s, 6H); 3.42(d, 1H); 3.68(d, 1H); 3.72(t, 2H); 4.2(t, 2H); 4.2(d, 1H); 4.48(d, 1H); 5.2(d, 1H); 5.76(d, 1H); 7.04(s, 1H); 6.9–7.2(m, 2H); 8.0–8.4(m, 2H).

61. The starting material may be prepared as follows: Reaction of 4-methylthipyridine with 5-equivalents of chloroacetone at 40°–50° for 18 hours gave 1-acetylmethyl-4-methylthipyridinium chloride. n.m.r. in solvent B:-2.27(s, 3H); 2.71(s, 3H); 6.0(s, 2H); 7.93(d, 2H); 8.5(d, 2H). Oxidation of this compound with a slight excess of metachlropenbenzoic acid in CH$_2$Cl$_2$TFA at 0° to ambient temperature gave 1-acetylmethyl-4-methanesulphinyl pyridinium chloride. n.m.r. in solvent B:-2.32(s, 3H); 3.01(s, 3H); 5.84(s, 8.5(d, 2H); 9.0(d, 2H).

62. n.m.r. in solvent B:-1.52(s, 6H); 2.22(s, 3H); 3.46(d, 1H); 3.74(d, 1H); 4.4(s, 2H); 5.25(d, 1H); 5.9(d, 1H); 5.23(s, 2H); 6.97(s, 1H); 6.9–7.2(m, 2H); 7.9–8.3(m, 2H).

63. The product is the 1-beta-oxide corresponding to the product of Example 49. It was obtained from this precursor by reaction with metachlorperbenzoic acid in CH$_2$Cl$_2$/TFA at 0° to ambient temperature for 30 minutes. n.m.r. in solvent B:-1.6(s, 6H); 2.22(s, 3H); 3.64(d, 1H); 3.88(d, 1H); 4.44(s, 2H); 5.06(d, 1H); 6.1(d, 1H); 5.23(s, 2H); 7.16(s, 1H); 6.9–7.2(m, 1H); 7.9–8.3(m, 1H).

64. The starting material may be obtained as follows: Reaction of 4-methylthipyridine with one equivalent of 2-dimethylaminoethyl chloride hydrochloride in EtOH at reflux for 18 hours gave 1-(2-dimethylaminoethyl)-4-methylthipyridinium chloride. n.m.r. in solvent B:-2.7(s, 3H); 2.87(s, 6H); 3.75(t, 2H); 4.92(t, 2H); 7.98(d, 2H); 8.84(d, 2H). Oxidation of this compound with metachlorperbenzoic acid in CH2Cl2/TFA at 0° to ambient temperature for 40 minutes gave 1-(2-dimethylaminoethyl)-4-methansulphinylpyridinium chloride. n.m.r. in solvent B:-3.0(s, 6H); 3.34(s, 3H); 3.87(t, 2H); 5.16(t, 2H); 8.52(d, 2H); 9.36(d, 2H);

65. n.m.r. in solvent B:-1.54(s, 6H); 2.86(s, 6H); 3.4–3.8(m, 4H); 4.3–4.7(m, 4H); 5.22(d, 1H); 5.9(d, 1H); 7.02(s, 1H); 6.9–7.2(m, 2H); 8.1–8.5(m, 2H).

66. The starting material may be obtained as follows: Reaction of 4-methylthiopyridine with 4 equivalents of N-acetyl-2-chloroethylamine at 80° for 4 hours gave, after precipitation from CH2Cl2 solution with EtOAc, 1-(2-acetylaminoethyl)-4-methylthipyridinium chloride in solvent B:-1.76(s, 3H); 2.69(s, 3H); 3.6(t, 2H); 4.5(t, 2H); 7.87(d, 2H); 8.64(d, 2H). This compound was reacted with one equivalent of metachlorperbenzoic acid in CH2Cl2/TFA at 0° to ambient temperature for 30 minutes. The product was precipitated from CH2Cl2/MeOH solution with ether to give 1-(2-acetylaminoethyl)-4-methanesulphinylpyridinium chloride. n.m.r. in solvent B:-1.76(s, 3H); 3.0(s, 3H); 3.66(t, 2H); 4.74(t, 2H); 8.47(d, 2H); 9.22(d, 2H).

The cephalosporin starting material may be obtained as follows:

To a stirred mixture of DMF (5.8 ml.) in anhydrous methylene chloride (415 ml.) at −10° was added dropwise oxalyl chloride (6.15 ml.). Stirring was continued at −10° for 30 minutes to give a gelatinous white precipitate of (chloromethylene) dimethylammonium chloride. To this stirred suspension was added powdered 2-((Z)-1-t-butoxycarbonyl-1-methylethoxyimino)-2-(2-tritylaminothiazol-4-yl)acetic acid (40.0 g.) followed by N-methylmorpholine (8.80 ml.). Stirring was continued for 30 minutes between −5° and −15°.

In another flask a suspension of 7-amino-3-azidomethylceph-3-em-4-carboxylic acid (17.85 g.) in anhydrous methylene chloride (150 ml.) was stirred for 1 hour with N,O-bis(trimethylsilyl)acetamide (34.5 ml.) to give a clear orange solution. This was transferred by syringe to the above acid chloride solution which was stirred at −10° during the addition. The reaction mixture was then allowed to warm to room temperature and stirred for a further 90 minutes. The mixture was then poured into water (500 ml.) and extracted with EtOAc (3×500 ml). The combined EtOAc etracts were washed with water, dried (Na2SO4) and the solvent was evaporated under reduced pressure to yield a buff foam. The crude product was dissolved in methylene chloride and applied to a column of Kieselgel 60 (125 g.). Elution with methylene chloride/MeOH/HOAc 96:2:2 v/v/v gave 3-azidomethyl-7-[2-(2-tritylaminothiazol-4-yl)-2-((Z-1-t-butoxycarbonyl-1-methylethoxyimino)acetamido]-ceph-3-em-4-carboxylic acid (46.4 g.) as a white foam. n.m.r. in solvent A: 1.30(s, 9H); 1.35(s, 6H); 3.37(d, 1H); 3.65(d, 1H); 3.9(d, 1H); 4.35(d, 1H); 5.10(d, 1H); 5.7(d, 1H); 6.66(s, 1H); 7.25(s, 15H).

An aqueous slurry of Raney nickel (10.2 g.) was added in one portion to a stirred solution of the azide (20.0 g.) in a mixture of MeOH (60 ml.) and TFA (60 ml.) at room temperature. A vigorous effervescence was observed. Stirring was continued for 1 hour and the Raney nickel was removed by filtration through diatomaceous earth. The filter pad was washed well with MeOH and the washings were combined with the filtrate. The solvents were evaporated under reduced pressure to give a pale green solid residue which was then stirred for 2 hours with a mixture of TFA (60 ml.) and water (1.5 ml.). This mixture was evaporated to dryness and the residue was stirred vigorously with water (400 ml.) for 30 minutes. The resulting solution was filtered through diatomaceous earth to remove the undissolved triphenylmethanol and the filtrate was applied to a column of Diaion HP20 resin (1 l.). The column was eluted with water (500 ml.) to remove inorganic material and then with aqueous MeOH 1:1 v/v. The fractions which were shown by HPLC to contain the product were evaporated under reduced pressure to yield 3-aminomethyl-7-[2-(2-(2-aminothiazol-4-yl)-2-((Z)-1-carboxy-1-methylethoxyimino)acetamido]ceph-3-em-4-carboxylic acid (4.20 g.) as a pale yellow foam having the following n.m.r. in solvent A: 1.4(s, 6H); 3.1–3.8(complex 4H,); 4.95(d, 1H); 5.7(d, 1H); 6.72(s, 1H).

EXAMPLES 53–55

The processes described in Examples 1, 5 and 6 respectively were repeated, but using the product of Example 36 as starting material, to give the following compounds.

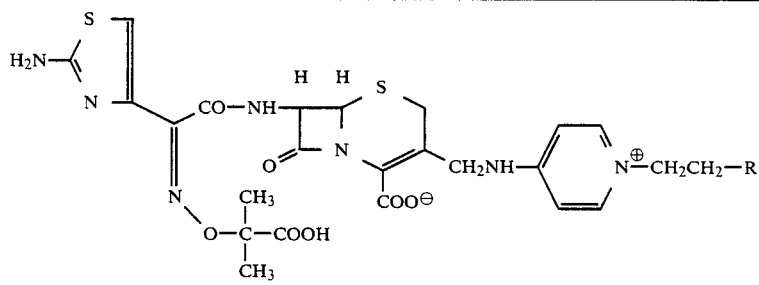

| Example | −R | Yield % | Footnotes |
|---------|----|---------|-----------|
| 53 | −NH−C(=NH)(H) | 37 | 1,2 |

-continued

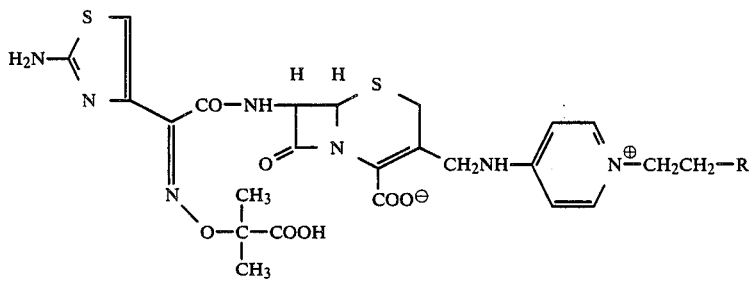

| Example | —R | Yield % | Footnotes |
|---|---|---|---|
| 54 | —NH—C(=NH)CH₃ | 50 | 3,4 |
| 55 | —NH=C(N(CH₃)₂)H | 42 | 5,6 |

Footnotes
1. Reaction carried out in DMF at ambient temperature for 6 hours using 4 equivalents of (ethoxymethylene)ammonium chloride and 8 equivalents of triethylamine. The solvent was evaporated and the residue was purified by chromatography on HP20 resin using water then acetonitrile/water 5–15:95–85 v/v as eluant.
2. n.m.r. in solvent B:-1.55(s, 6H); 2.29(s, 3H); 3.2–4.0(m, 4H); 4.1–4.5(m, 4H); 5.2(d, 1H); 5.84(d, 1H); 7.02(s, 1H); 7.16(m, 2H); 7.54 (m, 2H); 6.9–7.2(m, 2H); 7.8–8.4(m, 2H).
3. Reaction carried out in DMF/water 1:1 v/v with 15 equivalents of 1-ethoxyethylidene ammonium chloride and 15 equivalents of sodium bicarbonate at 0° to ambient temperature for 1 hour. The solvent was evaporated and the residue purified by HPLC on an octadecylsilane column using MeOH/water HOAc 15–20: 84–79:1 v/v/v.
4. n.m.r. in solvent B:-1.54(s, 6H); 2.13(s, 3H); 2.29(s, 3H); 3.4–3.8(m, 4H); 4.1–4.5(m, 4H); 5.18(d, 1H); 5.86(d, 1H); 7.02(s, 1H); 7.14(m, 2H); 7.54(m, 2H); 6.9–7.2(m, 2H); 8.0–8.4(m, 2H).
5. Reaction carried out in DMF atambient temperature for 2 hours using 2 equivalents of N,N-dimethyl-N-(dimethoxymethyl)amine. The solvent was evaporated and the residue purified by chromatography on HP20 resin using water then MeOH/water 20:80 v/v as eluant.
6. n.m.r. in solvent B:-1.52(s, 6H); 2.3(s, 3H); 2.99(s, 3H); 3.16(s, 3H); 3.4–4.0(m, 4H); 4.2–4.4(m, 4H); 5.14(d, 1H); 5.82(d, 1H); 6.96(s, 1H); 7.14, 7.53(d, d, 4H); 6.8–7.2(m, 2H); 8.0–8.4(m, 2H).

EXAMPLE 56

A solution of 7-[2-(2-tritylaminothiazol-4-yl)-2-((Z)-1-t-butoxycarbonyl-1-methylethoxyimino)acetamido]-3-(1-ethyl-4-pyridinio)aminomethylceph-3-em-4-carboxylate (410 mg.) in TFA (5 ml.) was set aside for 30 minutes. Water (0.5 ml.) was then added and after a further 30 minutes the solvent was evaporated under reduced pressure. The residue was triturated with water (25 ml.) and the resulting solution was filtered through diatomaceous earth to remove the insoluble triphenylmethanol. The filtrate was evaporated to dryness under reduced pressure to give an orange glass (310 mg.) which was purified by HPLC on an octadecylsilane column eluting with MeOH/water/HOAc 30:70:1 v/v/v. There was thus obtained 7-[2-(2-aminothiazol-4-yl)-2-((Z)-1-carboxy-1-methylethoxyimno)acetamido]-3-(1-ethyl-4-pyridinio)aminomethylceph-3-em-4-carboxylate (28 mg.) as a white solid having the following n.m.r. in solvent A: 1.43(t, 3H); 1.5(s, 6H); 3.43(d, 1H); 3.7(d, 1H); 4.22(q, 2H); 4.35(br, 2H); 5.2(d, 1H); 5.85(d, 1H); 6.77(d, 1H); 7.0(d, 2H); 8.25(br, 2H).

The starting material may be obtained as follows: To a stirred solution of 1-ethyl-4-pyridone (3.98 g.) in refluxing anhydrous toluene (60 ml.) was added recrystallised toluene-p-sulphonyl chloride (6.18 g.). After 5 minutes the reaction mixture was cooled to room temperature and the toluene was decanted from the gummy precipitate. Trituration of the precipitate with ether gave 4-chloro-1-ethylpyridinium toluene-p-sulphonate (9.98 g.) as an off-white solid having the following n.m.r. in $D_2O$: 1.6(t, 3H); 2.36(s, 3H); 4.58(q, 2H); 7.32(d, 2H); 7.66(d, 2H); 8.06(d, 2H); 8.74(d, 2H).

To a stirred suspension of 3-aminomethyl-7-t-butoxycarbonylaminoceph-3-em-4-carboxylic acid (3.28 g.) in MeOH (170 ml.) and triethylamine (4.17 ml.) was added 4-chloro-1-ethylpyridinium toluene-p-sulphonate. The solids rapidly dissolved to give an orange solution. After 2.5 hours the solvent was removed by evaporation under reduced pressure. The residue was dissolved in water (400 ml.) and the pH of the solution was adjusted to 6.0 by the addition of sodium bicarbonate. The solution was then applied to a column of Diaion HP20 resin (200 ml.) which was eluted initially with water to remove the remaining 3-aminomethyl starting material then with aqueous acetone 4:1 v/v. The fractions containing 7-t-butyoxycarbonylamino-3-(1-ethyl-4-pyridinio)aminomethylceph-3-em-4-carboxylate were combined, the acetone was evaporated and the residue freeze-dried to give 2.0 g. of a fluffy off-white solid.

The above aminopyridinium compound (250 mg.) was dissolved in TFA (0.66 ml.). After 30 minutes the solvent was evaporated under reduced pressure. The residue was dissolved in water (10 ml.) and to the stirred solution was added powdered sodium bicarbonate (718 mg.) followed by a solution of 2-((Z)-1-t-butoxycarbonyl-1-methylethoxyimino)-2-(2-tritylaminothiazol-4-yl)acetyl chloride (280 mg.) in acetone (5 ml.). The reaction mixture was stirred at room temperature overnight and then partitioned between EtOAc and water. The aqueous phase was acidified with N aqueous HCl to pH 3.0 and reextracted with EtOAc. The combined EtOAc extracts were washed with brine, dried and the solvent was evaporated under reduced pressure to give the crude starting material, 7-[2-(2-tritylaminothiazol-4-yl)-2-((Z)-1-t-butoxycarbonyl-1-methylethoxyimino)-acetamido]-3-(1-ethyl-4-pyridinio)aminomethylceph-3-em-4-carboxylate (410 mg.), as a yellow foam.

EXAMPLES 57–65

To a solution of 3-aminomethyl-7-[2-(2-aminothiazol-4-yl)-2-((Z)-1-carboxy-1-methylethoxyimino)acetamido]ceph-3-em-4-carboxylic acid (194 mg. 0.4 mmole) in DMF (11 ml.) and water (3 ml.) at 0° was added sodium bicarbonate (403 mg., 4.8 mmole) dissolved in the minimum volume of water, followed by 1-methyl-4-chloroquinolinium iodide (122 mg. 0.4 mmole). After 1 hour the mixture was treated with HOAc (288 μl., 4.8 mmole) and was evaporated to dryness under reduced pressure. The residue was dissolved in water (6 ml.) and purified by HPLC on an octadecylsilane column, using MeOH/water/HOAc 40:60:1 v/v/v as eluant. The fractions containing the product were combined, MeOH was removed by evaporation and the aqueous residue freeze-dired to give the product (50%). Using this general process, starting with the appropriate quaternary heterocycle, the following compounds were obtained.

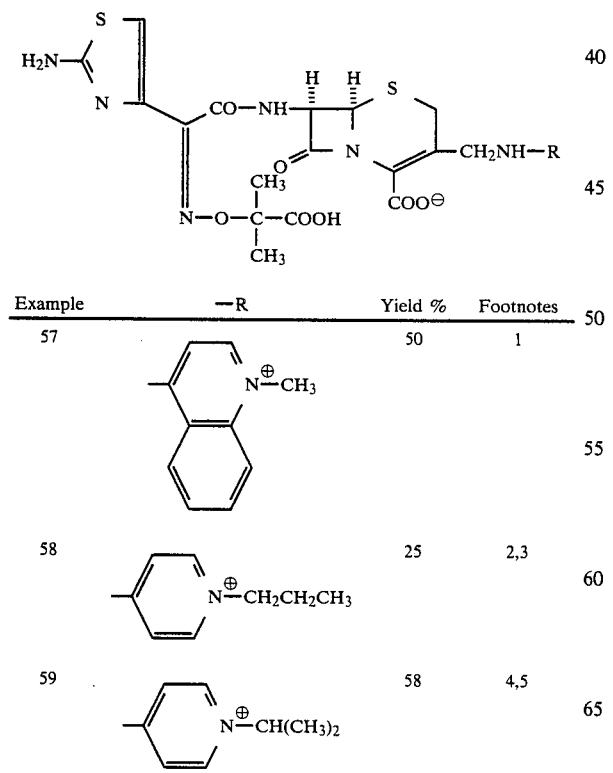

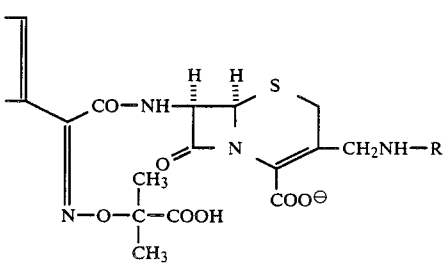

Footnotes
1. N.m.r. in solvent A:-1.4(s, 6H); 3.52(br, 2H); 4.6(br, 2H); 4.07(s, 3H); 5.1(d, 1H); 5.8(d, 1H); 6.7(s, 1H); 7.2–8.7 (complex, 6H).
2. N.m.r. in solvent A:-0.72(t, 3H); 1.35(s, 6H); 1.65(m, 2H); 3.4(br, 2H); 3.96(t, 2H); 4.2(br, 2H); 5.03(d, 1H); 5.71(d, 1H); 6.65(s, 1H); 6.92(q, 2H); 8.08(q, 2H).
3. The starting material may be prepared as follows: A solution of 4-hydroxypyridine (950 mg.) and 1-iodopropane (2.34 ml.) in acetone (30 ml.) was stirred under reflux for 2 hours with powdered potassium carbonate (2.76 g.). The reaction mixture was cooled to room temperature and filtered. The solvent was evaporated from the filtrate and the residue was purified by chromoatograph on Kieselgel 60 (100 g.) eluting with methylene chloride/MeOH 100:0 to 80:20 v/v to give 1-n-propyl-4-pyridone (1.05 g.), an oil having n.m.r. in CDCl₃:-0.9(t, 3H); 1.75(m, 2H9; 3.7(t, 2H); 6.23(d, 2H); 7.28(d, 2H). This material was chlorinated as described in the second part of Example 56 to give 4-chloro-1-n-propylpyridinium toluene-p-sulphonate.

4. N.m.r. in solvent A:-1.4(br, 12H); 3.32(d, 1H); 3.56(d, 1H); 4.15(d, 1H); 4.36(d, 1H); 4.4(m, 1H); 5.05(d, 1H); 5.75(d, 1H); 6.68(s, 1H); 6.95(m, 2H); 8.1(d, 1H); 8.27(d, 1H).

5. The starting material may be prepared in the same way as described in Footnote 3, using isopropyl bromide.

6. N.m.r. in solvent A:-1.4(s, 6H); 1.5(s, 9H); 3.3(d, 1H); 3.55(d, 1H); 4.15(d, 1H); 4.36(d, 1H); 5.05(d, 1H); 5.75(d, 1H); 6.67(s, 1H); 6.9(m, 2H); 8.3(m, 2H).

7. The starting material may be prepared as follows: A solution of 4-pyrone (730 mg.) in t-butylamine (3.0 ml.) was set aside for 3 days. The excess t-butylamine was evaporated under reduced pressure and the residue was purified by chromatography on Kieselgel 60 (20 g.) eluting with methylene chloride/MeOH 100:0 to 90:10 v/v to give 1-t-butyl-4-pyridone (530 mg.) N.m.r. in solvent A:-1.55(s, 9H); 6.4(d, 2H); 7.6(d, 2H). This material was chlorinated as described in the second part of Example 56 to give 4-chloro-1-t-butylpyridiniumtoluene-p-sulphonate.

8. N.m.r. in solvent A:-1.05(br, 4H); 1.4(s, 6H); 3.3(d, 1H); 3.6(d, 1H); 3.75(m, 1H); 4.18(d, 1H); 4.4(d, 1H); 5.1(d, 1H); 5.77(d, 1H); 6.69(s, 1H); 6.9(m, 2H9; 8.06(d, 1H); 8.24(d, 1H).

9. The starting material may be obtained as follows. A solution of 2,6-dicarboxy-4-pyrone (10.0 g.) and cyclopropylamine (3.8 ml.) in MeOH (300 ml.) was stirred at room temperature overnight. The precipitated salt was filtered off, dried under vacuum and heated to 200° for 30 minutes. The resulting black gum was extracted with methylene chloride (3×150 ml.). The extracts were concentrated and purified by chromatography on Kieselgel 60 (100 g.) using methylene chloride/MeOH 100:0 to 80:20 v/v to give 1-cyclopropyl-4-pyridone (1.26 g.) as an oil having n.m.r. in CDCl₃:-1.03(m, 4H); 3.38(m, 1H); 6.3(d, 2H); 7.4(d, 2H). This material was chlorinated as described in the second part of Example 56 to give 4-chloro-1-cyclopropylpyridinium toluene-p-sulphonate.

10. n.m.r. solvent A:-1.4(s, 6H9; 3.32(d, 1H); 3.57(d, 1H); 4.15(d, 1H); 4.36(d, 1H); 4.7(d, 2H); 5.05(d, 1H) 5.25(m, 2H); 5.75(d, 1H); 5.95(m, 1H); 6.68(s, 1H); 6.95(m, 2H); 7.95(d, 1H); 8.13(d, 1H).

11. The starting material may be prepared in the same way as described in Footnote 3, using allyl bromide.

12. N.m.r. in solvent A:-1.4(s, 6H); 3.28(d, 1H); 3.55(d, 1H); 4.3(br, 2H); 5.05(d, 1H); 5.69(d, 1H); 6.7(s, 1H); 7.1–7.9(m, 5H); 8.4–8.8(m, 2H).

13. The reaction was carried out at 70° with 2-bromoquinolizinium bromide.

14. N.m.r. in solvent A:-1.4(s, 6H); 2.7(s, 3H); 3.53(br, 2H); 3.95(s, 3H); 4.55(br, 2H); 5.1(d, 1H); 5.8(d, 1H); 6.7(s, 1H) 7.4–8.6 (complex, 5H).

15. The starting material may be prepared as follows. A solution of 4-chloroquinaldine (1.0 g.) and methyl iodide (1.12 ml.) in acetonitrile (3 ml.) was set aside overnight in the dark. The reaction mixture was diluted with ether and the resulting violet crystals of 1,2-dimethyl-4-chloroquinolinium iodide were filtered of and dried in vacuo to give a yield of 181 mg. N.m.r. in D₂O:-3.0(s, 3H); 4.38(s, 3H); 7.7–8.75 (complex, 5H).

16. N.m.r. in solvent A:-1.4(s, 6H); 2.7(s, 3H); 3.27(d, 1H); 3.53(d, 1H); 3.9(s, 3H); 4.4(d, 1H); 4.6(d, 1H); 5.0(d, 1H9; 5.65(d, 1H); 6.7(s, 1H9; 7.4–8.6 (complex, 4H).

17. The starting material may be prepared as follows. Powered 4,6-dichloro-2-methylquinoline (254 mg.) was added to a stirred solution of trimethyloxonium tetrafluoroborate (177 mg.) in acetontrile (1 ml.), and stirring was continued overnight. The solvent was evaporated and the residue was triturated with ether to give 4,6-dichloro-1,2-dimethylquinolinium tetrafluoroborate (296 mg.). N.m.r. in solvent A:-3.07(s, 3H); 4.44(s, 3H9; 7.9–8.8(complex, 4H).

EXAMPLES 66–67a

The general process described in Examples 57–65 was repeated and the following compounds were obtained.

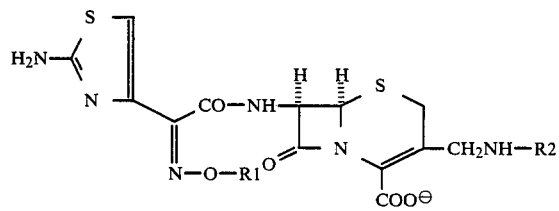

| Example | —R1 | —R2 | Yield % | Footnotes |
| --- | --- | --- | --- | --- |
| 66 | —CH₂CO₂H | (quinolinium-N-CH₃ with CH₃) | 25 | 1,2,3 |

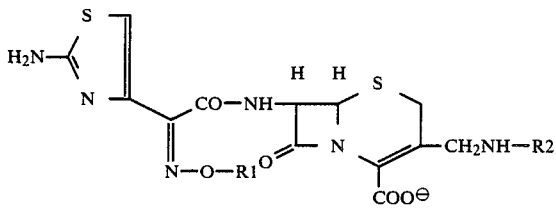

| Example | —R1 | —R2 | Yield % | Footnotes |
|---|---|---|---|---|
| 67 | —C$_2$H$_5$ | —⟨pyridinium⟩N$^{\oplus}$—CH$_3$ | 60 | 4,5,6 |
| 67a | ⟨cyclobutyl⟩—COOH | —⟨pyridinium⟩N$^{\oplus}$CH$_2$CH=CH$_2$ | 43 | 7,8,9 |

Footnotes

1. Prepared by the standard procedure of Examples 57–65 (except that DMF was replaced by acetonitrile), starting from the appropriate 3-aminomethylcephalosporin derivative and 4-chloro-1,2-dimethylquinolinium tetrafluoroborate, and working up the product by chromatography on Diaion HP20 SS resin.

2. N.m.r. in solvent A:-2.73(s, 3H); 3.44(q, 2H); 3.98(s, 3H); 4.53(m, 4H); 5.02(d, 1H); 5.68(d, 1H); 6.8(s, 1H); 7.3(s, 1H); 7.6–8.2(m, 3H); 8.48(d, 1H).

3. The 3-aminomethylcephalosporin may be prepared as follows:-Oxalyl chloride (337 μl.) and DMF (330 μl.) were added to CH$_2$Cl$_2$ (20 ml.) at −10°, and stirred for 30 minutes. 2((Z)-t-Butoxycarbonylmethoxyimino)-2-(2 tritylaminothiazol-4-yl)acetic acid and N-methylmorpholine (510 μl.) were added and stirring continued for 30 minutes. Meanwhile in a separate flask, a suspension of 7-amino-3-azidomethylceph-3-em-4-carboxylic acid (987 mg.) in dichloromethane (8 ml.) was treated with N,O-bis(trimethylsilyl)acetamide (1.91 ml.), and stirred for 1 hour to give a clear solution, which was transferred by syringe to the acid chloride solution. After stirring the mixture for 1 hour at −10°, the temperature was allowed to rise to ambient. The mixture was poured into water (25 ml.) and organics extracted with EtOAc (3×25 ml.). The crude product was filtered through a short SiO$_2$ column in EtOAc/HOAc 99:1 v/v, and evaporated to give 3-azidomethyl-7-[2-((Z)-t-butoxycarbonylmethoxyimino)-2-(2-tritylaminothiazol-4-yl)acetamido]ceph-3-em-4-carboxylic acid, having the following n.m.r. in solvent A:-1.4(s, 9H); 3.35(d, 1H); 3.63(d, 1H); 3.86(d, 1H); 4.38(d, 1H); 4.49(s, 2H); 5.09(d, 1H); 5.7(d, 1H); 6.73(s, 1H); 7.29(m, 15H).

The above 3-azidomethyl ompound (0.5 g.) was added to 90% v/v aqueous TFA (10 ml.), pre-cooled to 0°, and stirred for 30 minutes. Raney nickel (wet, 0.3 g.) was added, and the mixture stirred for 20 minutes, allowing temperature to rise to ambient. The mixture was filtered, the filtrate evaporated, the residue dissolved in a little water, and the pH raised to 2.5 with NaHCO$_3$. The product was purified by chromatography on a Diaion CHP20P column, eluting with 95:5 v/v water/CH$_3$CN, to give 3-aminomethyl-7-[2-(2-aminothiazol-4-yl)-2-((Z)-carboxymethoximino)acetamido]-ceph-3-em-4-carboxylic acid as its zwitterion, having the following n.m.r. in solvent A:-3.3(d, 1H); 3.44(d, 1H); 3.56(d, 1H); 3.69(d, 1H); 4.55(s, 2H); 5.01(d, 1H); 5.72(d, 1H); 6.82(s, 1H).

4. Prepared by the standard procedure of Examples 57–65 from the appropriate 3-aminomethylcephalosoporin derivative and 4-chloro-1-methylpyridinium iodide.

5. N.m.r. in solvent A:-1.16(t, 3H); 3.18(d, 1H); 3.47(d, 1H); 3.8(s, 3H); 4.04(q, 2H); 4.12(d, 1H); 4.4(d, 1H); 4.95(d, 1H); 5.58(d, 1H); 6.66(s, 1H); 6.9(m, 1H); 7.2(m, 1H); (8.0(m, 2H).

6. The starting material was prepared from 2-(Z)-ethoxyimino-2-(2-tritylaminothiazol-4-yl) acetic acid by the process described in the second part of Examples 23–52 to give 3-azidomethyl-7-[(Z)-2-ethoxyimino-2-(2-tritylaminothiazol-4-yl)acetamido]ceph-3-em-4-carboxylic acid, having the following n.m.r. in CDCl$_3$:- 1.29(t, 3H); 3.3(d, 1H); 3.54(d, 1H); 3.87(d, 1H); 4.3(q, 2H); 4.38(d, 1H); 4.97(d, 1H); 5.73(q, 1H); 6.72(s, 1H); 7.26m, 15H).

The 3-azidomethyl compound was reduced by the technique of Footnote 3 above except that formic acid was used as solvent in place of TFA, to give 3-aminomethyl-7-[2-(2-aminothiazol-4-yl)-2-((Z)-(ethoxyimino)acetamido]ceph-3-em-4-carboxylic acid as its zwitterion, having the following n.m.r. in solvent A:- 1.2(t, 3H); 3.26(d, 1H); 3.48(br s, 2H); 3.68(d, 1H); 4.08q, 2H); 4.97(d, 1H); 5.66(d, 1H); 6.69(s, 1H).

7. The starting material was prepared from 2-[(Z)-1-(t-butoxycarbonyl)cyclobut-1-yloxyimino]-2-(2-tritylaminothiazol-4-yl)acetic acid by the general process described in the second part of Examples 23 to 52 to give 3-azidomethyl-7-(2-[(Z)-1-(t-butoxycarbonyl)-cyclobut-1-yloxyimino -2-[2-tritylaminothiazol-4-yl]acetamido)ceph-3-em-4-carboxylic acid, having the following n.m.r. in solvent A:-1.38(s, 9H); 1.78(m, 1H); 1.89(m, 1H); 2.35(m, 4H); 3.45(d, 1H); 3.63(d, 1H); 3.9(d, 1H); 4.38(d, 1H); 5.13(d, 1H); 5.76(d, 1H); 6.68(s, 1H); 7.18–7.37(m, 15H).

The above 3-azidomethylcephalosporin derivative was reduced by the general method described in the second part of Examples 23 to 52 to give 3-aminomethyl-7-[2-(2-aminothiazol-4-yl)-2-[2-((Z)-(1-carboxy)cyclobut-1-yloxyimino)acetamido]ceph-3-em-4-carboxylic acid, which was partially purified by chromatography on Diaion CHP20 resin before use without further characterisation.

8. N.m.r. in solvent A:-1.8(m, 2H); 2.39(m, 4H); 3.29(d, 1H); 3.51(d, 1H); 4.22(d, 1H); 4.4(d, 1H); 4.74(d, 2H); 5.06(d, 1H); 5.21(d, 1H); 5.31(d, 1H); 5.71(d, 1H); 6:03(m, 1H); 6.75(s, 1H); 6.93(d, 1H); 7.32(d, 1H); 8.03(d, 1H); 8.21(d, 1H).

9. Prepared by the standard procedure of Examples 57-14 65, except that DMF was replaced by acetonitrile, from the appropriate 3-aminomethylcephalosporin derivative and 1-allyl-4-chloropyridinium toluene-p-sulphonate, and purifying the product by chromatography on Diaion HP20SS resin.

EXAMPLES 68-80

The solution was evaporated to dryness, triturated with EtOAc (50 ml.) and filtered. The solid product was added to TFA (15 ml.) pre-cooled to 0°, and stirred at this temperature for 30 minutes, before drowning into water (150 ml.) and filtering. The filtrate was evaporated to a small volume, and the pH adjusted to 3-4 with sodium bicarbonate. The product was isolated by chromatography on Diaion CHP20P resin (particle size 75–150μ), eluting with increasing proportions of acetonitrile in water. Appropriate fractions were combined, evaporated to a small volume and freeze-dried to give the product as its zwitterion.

Using this general procedure, starting with the appropriate protected thiazole acid, the following compounds were obtained.

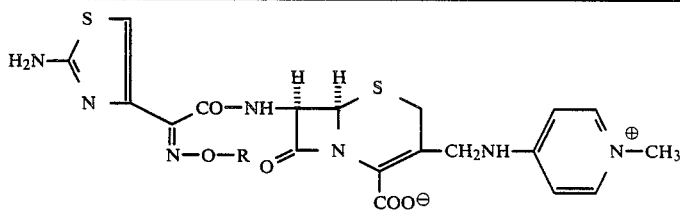

| Example | —R | Yield % | Footnotes |
|---|---|---|---|
| 68 | —CH$_2$CH$_2$N$_3$ | 49 | 1 |
| 69 | —H | 20 | 2 |
| 70 | —CH$_2$CH=CH$_2$ | 20 | 3,4 |
| 71 | cyclopentyl | 22 | 5,6 |
| 72 | —CH(CH$_3$)$_2$ | 34 | 3,7 |
| 73 | —CH$_2$COOH | 6 | 8,9 |
| 74 | cyclobutyl-COOH | 42 | 10,11 |
| 75 | —CH$_2$CO$_2$CH$_3$ | 16 | 12,13 |
| 76 | —CH$_2$CH$_2$OC$_2$H$_5$ | 7 | 12,14,15 |
| 77 | —CH$_2$C≡CH | 40 | 16 |
| 78 | —CH$_2$CH$_2$NH$_2$ | 29 | 17,18,19 |
| 79 | —CH$_2$—CH(CH$_2$)(CH$_2$) cyclopropyl | 40 | 20 |
| 80 | —CH$_2$CONH$_2$ | 8 | 21,22 |

Dry dichloromethane (5 ml.) was cooled to −10° and oxalylchloride (1.15 mM) followed by DMF (1.15 mM) was added, and the mixture stirred at −15° to −10° for 1 hour. To this was then added 2-((Z)-2-azidoethoxyimino)-2-(t-tritylaminothiazol-4-yl)acetic acid (1 mM) followed by triethylamine (1.15 mM), and the mixture stirred 1 hour at −15° to −10°.

In another flask a solution of 7-amino-3-(1-methyl-4-pyridinio)aminomethylceph-3-em-4-carboxylic acid (1.15 mM) as its partial salt with 1.76 moles TFA in dimethylacetamide (6 ml.) was treated with triethylamine (2.08 mM) and the pink suspension syringed into the flask containing the activated acid, followed by triethylamine (1.15 mM). After stirring for 1 hour at −10° and 1 hour at ambient temperature, the mixture was filtered.

Footnotes

1. N.m.r. in solvent A:-3.24(d, 1H); 3.48(d, 1H); 3.56(t, 2H 3.86(s, 3H); 4.18(m, 3H); 4.43(d, 1H); 5.0(d, 1H); 5.61(d, 1H); 6.79(s, 1H); 6.89(d, 1H); 7.41(d, 1H); 8.03(d, 1H); 8.2(d, 1H).

2. Starting from 2-(2-tritylaminothiazol-4-yl)-2-(Z)-trityloxyiminoacetic acid; n.m.r. in solvent A:-3.34(d, 1H); 3.61(d, 1H); 3.87(s, 3H); 4.31(s, 2H); 5.12(d, 1H); 5.77(d, 1H); 6.85(s, 1H); 6.97(d, 2H); 8.11(m, 2H).

3. The standard process was used except that the thiazole acid was activated using phosphorus pentachloride, deprotection was carried out by stirring with formic acid for 2.5 hours, and the final product was isolated by chromatography on Diaion HP20 resin, followed by HPLC using 80:20 v/v water-acetonitrile as eluant.

4. N.m.r. in solvent A:-3.88(q, 2H); 3.84(s, 3H); 4.31(q, 2H); 4.56(d, 2H); 5.01(d, 1H); 5.2(m, 2H); 5.62(d, 1H); 5.9(m, 1H); 6.72(s, 1H); 6.9(d, 1H); 7.31(d, 1H); 8.05(m, 2H).

5. The modified process of Footnote 3 was used, but omitting the final HPLC purification.

6. N.m.r. in solvent A:-1.72(m, 8H); 3.38(q, 2H); 3.84(s, 3H); 4.23(d, 2H); 4.64(m, 1H); 5.02(d, 1H); 5.63(d, 1H); 6.69(s, 1H); 6.9(d, 1H); 7.35(d, 1H); 8.1(m, 2H).

7. N.m.r. in solvent A:-1.2(d, 6H); 3.4(q, 2H); 3.8(s, 3H); 4.2(m, 3H); 5.0(d, 1H); 5.7(d, 1H); 6.7(s, 1H); 7.0(m, 2H); 8.1(m, 2H).

8. The standard process was used starting from 2-((Z)-t-butoxycarbonylmethoxyimino)-2-(2-tritylaminothiazo-4-yl)acetic acid, which was activated using phosphorus pentachloride.

9. N.m.r. in solvent A:-3.38(q, 2H); 3.85(s, 3H); 4.3(m, 2H); 4.48(s, 2H); 5.0(d, 1H); 5.65(d, 1H); 6.81(s, 1H); 6.9–7.3(m, 2H); 8.05(m, 2H).

10. The standard process was used starting from 2-[(Z)1-(t-butoxycarbonyl)cyclobut-1-yloxyimino]-2-(2-tritylaminothiazol-4-yl) acetic acid which was activated using phosphorus pentachloride.

11. N.m.r. in solvent A:-2.35(m, 4H); 3.35(q, 2H); 3.8(s, 3H); 4.2(m, 2H); 4.98(d, 1H); 5.66(d, 1H); 6.72(s, 1H); 6.83(m, 1H; 7.2(m, 1H); 8.0(m, 2H).

12. The standard process was used except that N-methylmorpholine was substituted for triethylamine as base.

13. N.m.r. in solvent A:-3.38(q, 2H9; 3.67(s, 3H); 3.85(s, 3H); 4.32(q, 2H); 4.67(s, 2H); 5.02(d, 1H); 5.64(d, 1H); 6.79(s, 1H); 6.9(m, 1H); 7.3(m, 1H); 8.1(m, 2H).

14. N.m.r. in solvent A:-1.06(t, 3H); 3.1–3.9(m, 6H); 3.85(s, 3H); 4.16(t, 2H); 4.34(q, 2H); 5.02(d, 1H); 5.64(d, 1H); 6.73(s, 1H); 6.9(m, 1H); 7.3(m, 1H); 8.1(m, 2H).

15. The thiazole acid starting material was prepared as follows. Ethyl (Z)-2-hydroxyimino-2-(2-tritylaminothiazol-4-yl)acetate hydrochloride (9.87 g.) was suspended in DMF (50 ml.) and treated with potassium carbonate (5.52 g.) and 2-bromoethyl ethyl ether (2.25 ml.). After stirring for 10 days at ambient temperature the mixture was diluted with water and worked up conventionally by extraction into EtOAc followed by chromatography on silica, eluting with 98:2 (v/v) $CH_2Cl_2$: EtOAc. The ethyl ester was dissolved in 1,2-dimethoxyethane (12 ml.), 2N aqueous NaOH solution (8.9 ml.) added, and the mixture heated under reflux for 2 hours. The mixture was cooled to 0°, the precipitate filtered, washed with a mixture of dimethoxyethane/water (1:1, v/v, 2×10 ml.) then dimethoxyethane/ether (1:1, v/v, 10 ml.). The precipitate was suspended in DMSO (50 ml.), acidified with 2NHCl (10 ml.), and diluted with water (500 ml.). The precipitate was filtered, washed well with water, and dried to give 2-((Z)-2-ethoxyethoxyimino)-2-(2-tritylaminothiazol-4-yl)acetic acid, having the following n.m.r. in $CDCl_3$:-1.07(t, 3H); 3.43(q, 2H); 3.62(t, 2H); 4.23(t, 2H); 6.5(s, 1H); 7.27(s, 15H).

16. N.m.r. in solvent A:-3.29(d, 1H); 3.32(t, 1H); 3.58(d, 1H); 3.9(s, 3H); 4.23(d, 1H); 4.5(d, 1H); 4.72(d, 2H); 5.07(d, 1H); 5.68(d, 1H); 6.82(s, 1H); 7.0(m, 1H); 7.3(m, 1H); 8.1(m, 2H).

17. The standard procedure was used, starting from 2-((Z)-2-t-butoxycarbonylaminoethoxyimino)-2-(2-tritylaminothiazol-4-yl)acetic acid; product isolated as mono TFA salt.

18. N.m.r. in solvent A:-3.12(t, 2H); 3.22(d, 1H); 3.52(d, 1H); 3.83(s, 3H); 4.3(m, 4H); 5.0(d, 1H); 5.63(d, 1H); 6.79(s, 1H); 6.9(m, 1H); 7.1(m, 1H); 8.05(m, 2H).

19. The starting material was prepared as follows. Using the procedure of Footnote 15, ethyl 2-((Z)-2-bromoethoxyimino)-2-(2-tritylaminothiazol-4-yl)acetate was prepared from 1,2-dibromoethane, and reacted with sodium azide in DMF solution. Purification by chromatography gave ethyl 2-((Z)-2-azidoethoxyimino)-2-(2-tritylaminothiazol-4-yl)acetate, which was dissolved in 1,2-dimethoxyethane and hydrogenated using 5% w/w palladium on charcoal as catalyst at ambient temperature and pressure for 16 hours. Catalyst was filtered off, and the solution was treated with bis(O-t-butyl)carbonic anhydride at ambient temperature. After 48 hours, the reaction was worked up conventionally, and the product isolated by chromatography on silica, eluting with 60:40 -1 v/v hexane: EtOAc. The ethyl ester was saponified (see Footnote 15) to give 2-((Z)-2-t-butoxycarbonylaminoethoxyimino)-2-(2-tritylaminothiazol-4-yl)acetic acid, having the following n.m.r. in $CDCl_3$:-1.33(s, 9H; 3.37(m, 2H); 4.27(t, 2H); 5.38(br s, 1H); 6.59(s, 1H); s, 1H); 7.29(m, 16H).

20. N.m.r. in solvent A:-0.2–0.6(m, 4H); 1.15(m, 1H); 3.18(d, 1H); 3.49(d, 1H); 3.85(s+d, 5H); 4.15(d, 1H); 4.45(d, 1H); 4.99(d, 1H); 5.6(d, 1H9; 6.69(s, 1H); 6.9(m, 1H); 7.4(m, 1H); 8.1(m, 2H).

21. (Z)-2-Carbamoylmethoxyimino-2-(2-tritylaminothiazol-4-yl)acetic acid (486 mg.), 1-hydroxybenzotriazole (156 mg.), and dicyclohexylcarbodiimide (206 mg.) were placed in a dry flask under argon, and dissolved in dimethylacetamide (4 ml.). The mixture was stirred for 40 minutes to give the activated ester, which was then reacted under the standard conditions with 7-aminocephalosporin.

22. N.m.r. in solvent A:-3.19(d, 1H); 3.49(d, 1H); 3.82(s, 3H); 4.37(m, 4H); 4.99(d, 1H); 5.65(d, 1H); 6.8(s, 1H); 7.2(m, 2H); 8.0(m, 2H).

The cephalosporin starting material may be obtained as follows: 7-Amino-3-azidomethylceph-3-em-4-carboxylic acid (170 g.) was suspended by stirring in water (750 ml.) and sodium bicarbonate (60 g.) added carefully, followed by t-butanol (750 ml.). Bis(O-t-butyl)carbonic anhydride (170 ml.) dissolved in t-butanol (375 ml.) was added and the mixture left to stir at ambient temperature; further portions of reagent (20 ml.) in t-butanol (40 ml.) were added after 24 and 48 hours. After 72 hours, t-butanol was removed by evaporation and the aqueous residue, diluted with water to 21°, was cooled in ice. The pH was reduced to 3 with concentrated hydrochloric acid, and the precipitate filtered, and washed free of acid. After drying under vacuum, the crude product was extracted successively with 500 ml. and two 400 ml. portions of acetonitrile. The combined extracts were evaporated to a small volume and filtered to give 3-azidomethyl-7-t-butoxycarbonylaminoceph-3-em-4-carboxylic acid (84 g.), having the following n.m.r. in solvent A: 1.4(s, 9H); 3.5(d, 2H); 4.2(d, 2H); 5.0(d, 1H); 5.4(d, 1H).

The above cephalosporin (84 g.) was dissolved in acetic acid (750 ml.) and chilled to 15°; to this was added activated zinc (77 g.) in portions over 10 minutes, controlling the exotherm to less than 30°. After stirring for 30 minutes the mixture was diluted with water (700 ml.), filtered, and the filter cake washed with 3 portions of 1:1 v/v HOAc/water (150 ml.). The filtrate was stirred and hydrogen sulphide passed in for 1 hour then purged with a nitrogen stream prior to filtration through diatomaceous earth, finally washing the filter cake well. The filtrate was evaporated to a small volume and filtered to give 3-aminomethyl-7-t-butoxycarbonylaminoceph-3-em-4-carboxylic acid (55 g.) as its zwitterion, having the following n.m.r. in d$_6$DMSO: 1.38(s,9H); 3.17(d,1H); 3.44(d,2H); 3.55(d,1H); 4.85(d,1H); 5.31(d,1H); 7.76(d,1H).

3-Aminomethyl-7-t-butoxycarbonylaminoceph-3-em-4-carboxylic acid (16.3 g.) was stirred in DMF (350 ml.) in an ice-bath, while sodium bicarbonate (8.4 g.) in water (170 ml.) was added. A solution of 4-chloro-1-methylpyridinium iodide (25.4 g.) in DMF (200 ml.) was added and the mixture stirred for 5 hours, allowing the temperature to rise to ambient. After reducing the pH to 6 with HOAc, solvents were evaporated and the residue dissolved in water (500 ml.). The pH was adjusted to 7, and the solution applied to a column of Diaion HP20 resin (1l.) made up in water, which was eluted successively with water, 90:10 and 80:20 v.v water/acetone mixtures. Fractions containing product were combined, evaporated, and the residue triturated with acetonitrile to give 7-t-butoxycarbonylamino-3-(1-methylpyridinio)aminomethylceph-3-em-4-carboxylic acid (13.7 g) as its zwitterion, having the following n.m.r. in solvent A: 1.4(s,9H); 3.5(d,2H); 3.8(s,3H); 4.3(d,2H); 5.0(d,1H); 5.4(dd,1H); 6.9(m,2H); 7.7(d,1HO; 8.1(m,2H).

The above cephalosporin (13.7 g.) was added with stirring to TFA (50 ml.) cooled in a water bath. After 30 minutes the solvent was evaporated and the residue triturated with ether (4 changes of solvent). The solid was filtered, washed well with ether, and dried over potassium carbonate under high vacuum, to give 7-amino-3-(1-methylpyridinio)aminomethylceph-3-em-4-carboxylic acid (17.2 g.) as a partial salt with 1.76 moles of TFA, having the following n.m.r. in solvent A: 3.5(s,2H); 3.8(s,3H); 4.4(d,2H); 5.1(dd,2H); 6.9(d,2H); 8.1(dd,2H).

EXAMPLES 81–82

The appropriate 3-aminomethylcephalosporin derivative was reacted with 4-chloro-1-methylpyridinium iodide and the following compounds were thus obtained

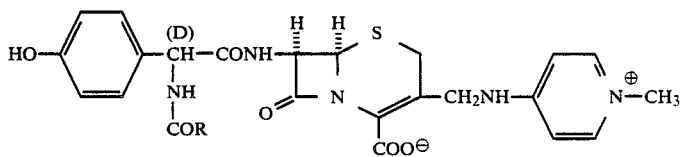

| Example | —R | Yield % | Footnotes |
|---|---|---|---|
| 81 | —N(CO)₂N—C₂H₅ (2,6-dioxopiperazinyl-ethyl) | 78 | 1,2,3 |
| 82 | 6-hydroxy-3-oxo-pyridazinyl | 6 | 4,5,6 |

Footnotes
1. Process carried out in DMF in presence of 3 equivalents of NaHCO$_3$ for 3.5 hours at ambient temperature. Reaction mixture worked up by addition of HOAc and product purified by chromatography on HP20 resin using MeOH/water 0:100 to 40:60 v/v as eluant.
2. n.m.r. in solvent B:1.08(t, 3H); 3.2–3.8(m, 6H); 3.9(s, 3H); 4.3(m, 2H); 5.05(d, 1H); 5.55(m, 1H); 5.75(m, 1H); 6.75(d, 2H); 7.25(d, 2H); 6.85–7.15(m, 2H): 8.0–8.4(m, 2H).
3. The starting material may be obtained as follows. To a solution of D-(-)-2-[(4-ethyl-2,3-dioxopiperazin-1-yl)carbonylamino]-2-(4-hydroxyphenyl)acetic acid (1.8 g.) in acetonitrile (1.6 ml.) and dimethylacetamide (8.0 ml.) under nitrogen was added dropwise a mixture of trichloromethyl chloroformate (342 µl) and acetonitrile (1 ml.) over 15 minutes at −20°. After 1 hour a solution of 7-amino-3-azidomethylceph-3-em-4-carboxylic acid hydrochloride (1.4 g.) in dimethylacetamide (6 ml.) and trichloromethylsilane (305 µl.) was added dropwise over 10 minutes at −20°. The resulting mixture was held at −20° for 90 minutes and then concentrated under reduced pressure below 30° To the residue was added a solution of NaHCO$_3$ (1.2 g.) in water (14 ml.). After 1 hour more water was added and the mixture was cooled in ice. The precipitated solid was collected and purified by chromatography on an HP20 resin column using MeOH/water 0:100 to 15:85 v/v as eluant to give the 7-acylamino-3-azidomethylcephalsporin derivative. n.m.r. in solvent A:-1.08(t, 3H); 3.2–4.02(m, 6H); 3.78(d, 1H); 4.44(d, 1H); 4.94(d, 1H); 5.48(d, 1H); 5.62(d, 1H); 6.75(d, 2H); 7.25(d, 2H); 9.7(d, 1H).

The above 3-azidomethyl derivative (150 mg.) in MeoH (15 ml.) and 2N aqueous HCl (175 µl.) was hydrogenated on 10% w/w palladium on carbon (50 mg.) at ambient temperature and 4 atmospheres pressure. After 5 hours more catalyst (50 mg.) was added. Stirring was continued for 2 hours, the mixture filtered through diatomaceous earth, and the filtrate evaporated. The residue was purified by chromatography on HP20 resin using MeOH/water 0:100 to 20:80 v/v as eluant to give the 7-acylamino-3-aminomethylcephalosporin derivative as the hydrochloride. n.m.r. in solvent F:-1.08(t, 3H); 3.1-4.08(m, 8H): 5.0(d, 1H); 5.54(m, 1H); 5.73(d, 1H); 6.75(d, 2H); 7.25(d, 2H).

4. Process carried out in water/DMF 1:3 v/v in presence of 4.5 equivalents of NaHCO3 for 75 minutes at ambient temperature. A further equivalent of NaHCO3 was added and the reaction worked up after 45 minutes by evaporation to dryness. The product was precipitated from MeOH solution with ether and further purified by HPLC on an octadecylsilane column eluted with MeOH/water/HOAC 15:84:1 v/v/v as eluant.

5. n.m.r. in solvent B:-3.45(m, 2H); 3.91(s, 3H); 4.32(m, 2H); 5.05(d, 1H) 5.73 (br s, 1H); 5.77(d, 1H); 6.74(d, 2H); 6.86-7.14(m, 2H); 7.29(d, 2H); 7.97-8.4(m, 2H).

6. The starting material may be obtained as follows. To a stirred solution of 3,5-dihydroxy-6-carboxy-1,2,4-triazine (475 mg.) in DMF (30 ml.) under nitrogen at −15° was added triethylamine (0.45 ml.) and isobutyl chloroformate (0.41 ml.). The temperature was maintained at −15° for 1 hour, then at ambient temperature for 1 hour. The solution was again cooled to −15° and a solution of 3-azidomethyl-7-[D-2-amino-2-(4-hydroxyphenyl)acetamido]ceph-3-em-4-carboxylic acid (1.22 g.) and triethylamine (0.42 ml.) in water (15 ml.) was added. After stirring 1 hour at −15° the mixture stirred at ambient temperature for 24 hours. The solution was evaporated and the residue was purified by chromatography on HP20 resin using MeOH/water 0:100 to 50:50 v/v as eluant, n.m.r. of bis-triethylamine salt in solvent B:-1.2(t, 6H); 3.12(q, 4H); 3.53(m, 2H); 3.89(d, 1H); 4.42(d, 1H); 5.08(d, 1H); 5.6-5.9(m, 2H); 6.74(d, 2H); 7.28(d, 2H); 9.46(m, 1H).

A solution of the above 3-azidomethyl derivative (373 mg.) in MeOH (10 ml.) and 6N aqueous HCl (0.25 ml.) was hydrogenatedover 10% w/w palladium on carbon (180 mg.) at ambient temperature and 4-atmospheres pressure. After 3 hours a second portion (90 mg.) of catalyst was added. After 2 hours the mixture was filtered through diatomaceous earth, the filtrate evaporated and the residue purified by chromatography on HP20 resin using water as eluant. n.m.r. in solvent B:-3.55(m, 2H); 3.72(m, 2H); 5.02(d, 1H); 5.71(m, 1H); 5.76(d, 1H); 6.74(d, 2H); 7.23(d, 2H).

EXAMPLES 83-90

The general process described in Examples 23-52 was repeated using the appropriate heterocyclic starting material. The reactions were carried out in DMF in the presence of triethylamine or DMF/water mixtures in the presence NaHCO3 at a temperature in the range ambient to 90° for 1-20 hours. The product was purified on an octadecylsilane column and the following compounds were thus prepared.

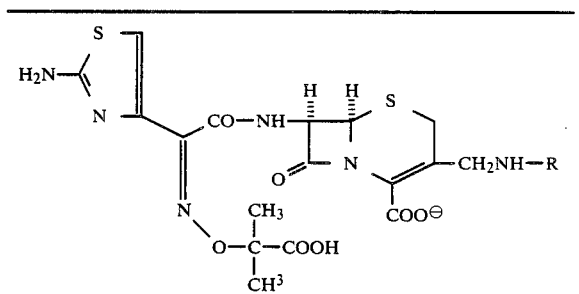

| Example | −R | Yield % | Footnotes |
|---|---|---|---|
| 83 | CH3–N, ⊕N–CH3 (thiazole) | 11 | 1,2,3 |
| 84 | N, ⊕N−CH3, CH3 (pyridinium) | 26 | 4,5,6 |
| 85 | CH3, ⊕N, S | 13 | 7,2,8 |
| 86 | CH3, ⊕N−O, CH3 | 32 | 9,10,11 |
| 87 | NH2, ⊕N, N, CH3 | 23 | 12,13,14 |
| 88 | CH2−C6H5, ⊕N, S | 20 | 15,16,17 |
| 89 | ⊕N−CH3, S | 12 | 18,19,20,21 |
| 90 | CH3, ⊕N, N | 47 | 22,5,23 |

Footnotes

1. Starting material 2-chloro-1,3-dimethylimidazolium iodide.

2. HPLC eluant MeOH/water/HOAc 20:79:1 v/v/v.

3. n.m.r. in solvent B:-1.49(br s, 6H); 3.6(br s, 8H); 4.1–4.2(m, 2H); 5.06(d, 1H); 5.73(d, 1H); 6.75(s, 1H); 7.19(s, 1H).

4. The starting material may be prepared as follows. Reaction of 4-chloro-6-methylpyrimidine with trimethyloxonium tetrafluoroborate in $CH_2Cl_2$ at ambient temperature for 18 hours followed by heating under reflux in MeOH for 24 hours gave a mixture of 4-chloro-1,6-dimethylpyrimidinium and 4-chloro-3,6-dimethylpyrimidinium tetrafluoroborates.

5. HPLC eluant MeOH/water/HOAc 15:84:1 v/v/v.

6. Single isomer product. n.m.r. in solvent B:-1.52(s, 3H); 1.55(s, 3H); 2.55(s, 3H); 3.45(m, 2H); 3.77(s, 3H); 4.35(d, 1H); 4.75(d, 1H); 5.16(d, 1H); 5.87(d, 1H); .68(s, 1H); 7.0(s, 1H); 8.8(s, 1H).

7. The starting material may be prepared by reaction of 2-bromothiazole and trimethyloxonium tetrafluoroborate in $CH_2Cl_2$ for 18 hours at ambient temperature to give 2-bromo-3-methylthiazolium tetrafluoroborate.

8. n.m.r. in solvent B:-1.54(s, 3H); 1.55(s, 3H); 3.6(m, 2H); 3.66(s, 3H); 4.48(brs, 2H); 5.18(d, 1H); 5.87(d, 1H); 7.0(s, 1H); 7.13(d, 1H); 7.53(s, 1H).

9. The starting material may be prepared by reaction of 3-methoxy-5-methylisoxazole with trimethyloxonium tetrafluorobroate in $CH_2Cl_2$ for 3.5 hours at reflux to give 2,5-dimethyl-3-methoxyisoxazolium tetrafluoroborate.

10. HPLC eluant MeOH/water/HOAc 23:76:1 v/v/v.

11. n.m.r. in solvent B:-1.53(s, 1H); 1.54(s, 1H); 2.42(s, 3H); 3.56(m, 2H); 3.85(s, 3H); 4.39(brs, 2H); 5.18(d, 1H); 5.88(d, 1H); 6.68(s, 1H); 7.01(s, 1H).

12. The starting material may be prepared as follows. Reaction of 4-chloro-6-methylpyrimidine and O-(2,4,6-trimethyl)benzenesulphonylhydroxylamine in $CH_2Cl_2$ for 4 hours at ambient temperature gave 3-amino-4-chloro-6-methylpyrimidinium 2,4,6-trimethylbenzenesulphonate.

Heating this compound in MeOH under reflux for 5 hours gave 3-amino-4-methoxy-6-methylpyrimidinium 2,4,6-trimethylbenzenesulphonate.

13. HPLC eluant MeOH/water/HOAc 18:81:1 v/v/v.

14. n.m.r. in solvent B:-1.54(s, 3H); 1.53(s, 3H); 2.18(s, 3H); 2.52(s, 6H); 3.56(m, 2H); 4.3(d, 2H); 4.75(d, 2H); 5.18(d, 1H); 5.9(d, 1H); 6.78(s, 3H); 7.06(s, 1H), 8.75(s, 1H).

15. The starting material was prepared by reaction of equimolar amounts of 2-bromothiazole and benzyl bromide at ambient temperature for 4 hours to give 2-bromo-3-benzylthiazolium bromide.

16. HPLC eluant MeOH/aqueous sodium bicarbonate (pH 6.0)30:70 v/v.

17. n.m.r. in solvent B:-1.54(s, 6H); 3.4(m, 2H); 4.5(m, 2H); 5.16(d, 1H); 5.36(s, 2H); 5.9(d, 1H); 7.0–7.6(m, 8H).

18. Starting material prepared by reaction of 5-chlorothiazole with trimethyloxonium tetrafluoroborate in $CH_2Cl_2$ at ambient temperature for 3 hours to give 5-chloro-3-methylthiazolium tetrafluoroborate.

19. The reaction product was first purified by chromatography on HP20 resin using water $CH_3CN$ 100:0 to 60:40 v/v as eluant.

20. HPLC eluant MeOH/aqueous sodium bicarbonate (pH 6.0)

21. n.m.r. in solvent B:-1.52(s, 3H); 1.55(s, 3H); 3.49(m, 2H); 3.91(s, 3H); 5.19(d, 1H); 5.27(d, 1H); 5.96(d, 1H); 5.59(d, 1H); 6.94(s, 1H); 8.06(s, 1H); 9.49(s, 1H).

22. Starting material prepared by reaction of 2-methoxypyrimidine with trimethyloxonium tetrafluoroborate in $CH_2Cl_2$ at ambient temperature for 4 hours to give 1-methyl-2-methoxypyrimidinium tetrafluoroborate.

23. n.m.r. in solvent B:-1.5(s, 6H); 3.45(d, 1H); 3.7(d, 1H); 3.82(s, 3H); 4.44(d, 1H); 4.95(d, B 1H); 5.15(d, 1H); 5.9(d, 1H); 7.05(s, 1H); 7.0–7.25(m, 1H); 8.6–8.95(m, 2H).

EXAMPLES 91–99

The general process described in Examples 68–80 was repeated using the appropriate protected activated acid as starting material, and the following compounds were thus obtained:

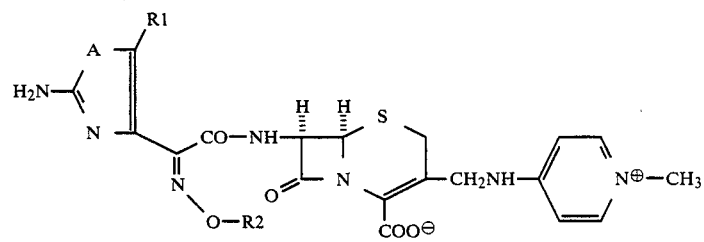

| Example | A | R1 | —R2 | Yield % | Footnotes |
|---------|---|----|----|---------|-----------|
| 91 | S | H | —CH$_2$CH$_2$Br | 4 | 1,2 |
| 92 | O | H | —CH$_3$ | 25 | 3,4,5,6 |
| 93 | S | H | 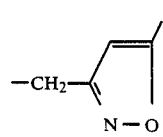 | 27 | 7,4,8 |

-continued

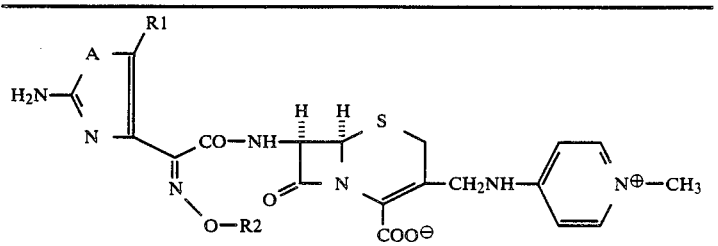

| Example | A | R1 | —R2 | Yield % | Footnotes |
|---|---|---|---|---|---|
| 94 | S | H | —CH₂-(tetrazole) | 10 | 9,4,10 |
| 95 | S | H | —CH₂-(phenyl) | 15 | 11,4,12 |
| 96 | S | H | —CH₂CN | 2 | 13,4,14 |
| 97 | S | Br | —CH₃ | 9 | 15,16,4,17 |
| 98 | S | H | —CH₂CH₂Cl | 8 | 18,4,19 |
| 99 | S | Cl | —CH₃ | 7 | 20,16,4,21 |

Footnotes

1. The starting material 2-(2-tritylaminothiazol-4-yl)-2-((Z)-2-bromoethoxyimino)acetic acid (UK Patent Application No. 2017702A) was activated with trichloromethylchloroformate and the cephalsporin was silylated with trimethylsilyl chloride.
2. n.m.r. in solvent A:-3.3–3.8(m, 4H); 3.9(s, 3H); 4.2–4.5(m, 4H); 5.05(d, 1H); 5.67(d, 1H); 6.83(s, 1H); 6.95(m, 1H); 7.42(m, 1H); 8.14(m, 2H).
3. The starting material was 2-(2-t-butoxycarbonylaminooxazol-4-yl)-2-((Z)-methoxyimino)acertic acid (UK Patent Application No. 2106519A).
4. The base used was N-methylmorpholine.
5. Deprotection was carred out with TFA/anisole.
6. n.m.r. in solvent A:-3.42(q, 2H); 3.88(s, 3H); 4.34(q, 2H); 5.02(d, 1H); 5.64(d, 1H); 6.96(m, 1H); 7.38(m, 1H) 7.5(s, 1H); 8.16(m, 2H).
7. The starting material was prepared by reaction of ethyl 2-(2-tritylaminothiazol-4-yl)-2-((Z)-hydroxyimino)acetate with 3-chloromethyl-5-methylisoxazole followed by hydrolysis of the resulting ester to give 2-(2-tritylaminothiazol-4-yl)-2-[(Z)-2-(5-methylisoxazol-3-yl)methoxyimono]acetic acid: n.m.r. in CDCl₃:-2.32(s, 3H); 5.21(s, 2H); 6.35(s, 1H); 6.61(s, 1H); 7.29(s, 15H).
8. n.m.r. in solvent A:-2.38(s, 3H); 3.48(q, 2H); 3.9(s, 3H); 4.35(s, 2H); 5.15(d, 1H); 5.2(s, 2H); 5.82(d, 1H); 6.34(s, 1H); 6.98(s, 1H); 7.0(m, 2H); 8.2(m, 2H).
9. The starting material was 2-(2-trietylaminothiozol-4-yl)-2-[(Z)-2-tetrazol-5-yl)methoxyimino]acetic acid (UK Patent Application No. 2017702A).
10. n.m.r. in solvent A:-3.37(q, 2H); 3.9(s, 3H); 4.36(q, 2H); 5.04(d, 1H); 5.42(s, 2H); 5.71(d, 1H); 6.87(s, 1H); 6.96(m, 1H); 7.36(m, 1H); 8.16(m, 2H).
11. The starting material was prepared by reaction of ethyl 2-(2-tritylaminothiazol-4-yl)-2-((Z)hydroxyimino))acetate with benzyl bromide followed by hydrolysis of the ester to give 2-(2-tritylaminothiazol-4-yl)-2-((Z)-benzyloxyimino)acetic acid; n.m.r. in solvent C:-5.44(s, 2H); 6.69(s, 1H); 7.2–7.7(m, 20H).
12. n.m.r. in solvent A:-3.54(q, 2H); 3.96(s, 3H); 4.4(q, 2H); 5.21(d, 1H); 5.32(s, 2H); 5.86(d, 1H); 7.06(s, 1H); 7.44(m, 5H); 6.9–8.5(m, 4H).
13. The starting material was 2-(2-tritylaminothiazol-4-yl)-2-((Z)-cyanomethoxyimino)acetic acid (UK Patent Application No. 2017702A).
14. n.m.r. in solvent A:-3.37(q, 2H); 3.9(s, 3H); 4.36(q, 2H); 4.98(s, 2H); 5.05(d, 1H); 5.65(d, 1H); 6.92(s, 1H); 6.8–8.4(m, 4H).
15. The starting material was prepared by consecutive formylation and bromination of ethyl 2-(2-aminothiazol-4-yl)-2-((Z)-methoxyimino)acetate followed by hydrolysis of the ester to give 2-(5-bromo-2-formylaminothiazol-4-yl)-2-((Z)-methoxyimino)acetic acid; n.m.r. in d₆DMSO:-3.97(s, 3H); 8.55(s, 1H).
16. Deprotection was carried out with concentrated aqueous HCL/MeOH.
17. n.m.r. in solvent A:-3.5(m, 2H); 3.9(s, 3H); 4.32(m, 2H); 5.14(d, 1H); 5.8(d, 1H); 6.89(m, 2H); 7.2(m, 2H).
18. The starting material was prepared by reaction of ethyl 2-(2-tritylaminothiazol-4-yl)-2-((Z)-hydroxyimino)acetate with 1-bromo-2-chloroethane followed by hydrolysis of the ester to give 2-(2-tritylaminothiazol-4-yl)-2-[(Z)-(2-chloroethoxy)imino]acetic acid; n.m.r. in solvent C:-3.75(t, 2H); 4.36(t, 2H); 6.64(s, 1H); 7.35(s, 15H).
19. n.m.r. in solvent A:-3.39(m, 2H); 3,89(s, 3H); 4.28(m, 2H); 5.04(d, 1H); 5.68(d, 1H); 6.84(s, 1H); 6.928m, 2H); 7.46(m, 2H).
20. The starting material was prepared by consecutive formylation and chlorination of ethyl 2-(2-aminothiazol-4-yl)-2-((Z)-methoxyimino)acetate followed by hydrolysis of the ester to give 2-(5-chloro-2-formylaminothiazol-4-yl)-2-((Z)-methoxyimino)acetic acid; n.m.r. in solvent C:-3.99(s, 3H), 8.5(s, 1H).
21. n.m.r. in solvent A:-3.5(q, 2H); 3.87(s, 6H); 4.32(s, 2H); 5.12(d, 1H); 5.79(d, 1H); 6.99(m, 2H); 8.16(m, 2H).

EXAMPLES 100–103

A solution of NaHCO₃ (0.54 mM) in water (1.5 ml.) was added to a solution of a 7-acyl-3-aminomethylcephalosporin derivative (0.135 mM) in DMF (4 ml.) at 0° followed after a few minutes by 1-(2-t-butoxycarbonylaminoethyl)-4-chloropyridinium toluene-p-sulphonate (0.16 mM). The temperature was allowed to rise to ambient over 5 hours and the solvent was evaporated.

The residue was dissolved in CH₂Cl₂/TFA 1:1 v/v. After 1 hour the mixture was evaporated to dryness and the residue purified by chromatography on Diaion HP20 resin.

Using the general process the following compounds were prepared.

quired. Product purified by precipitation from DMF with water.

5. n.m.r. in solvent A:-3.2–3.6(m, 4H); 3.91(s, 3H); 4.38(m, 4H); 5.21(d, 1H); 5.86(d, 1H); 6.9–8.4(m, 8H); 7.08(s, 1H).

6. n.m.r. in solvent A:-3.2–3.7(m, 4H); 3.92(t, 2H); 4.4(m, 6H); 5.2(d, 1H); 5.86(d, 1H); 6.9–7.3(m, 2H); 7.05(s, 1H); 8.0–8.4(m, 2H).

The starting materials for use in the above process may be obtained as follows:

Triethylamine (1.0 mM) and phosphorus pentachloride (1.0 mM) were added to a solution of 2-(2-tritylaminothiazol-4-yl)-2-((Z)-cyanomethoxyimino)acetic acid (UK Patent Application No. 2017702A) (1.0 mM) in CH₂Cl₂ (2.5 ml.) under argon at 0° and the

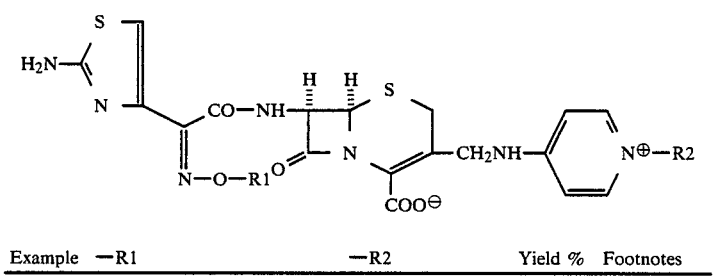

| Example | —R1 | —R2 | Yield % | Footnotes |
|---------|-----|-----|---------|-----------|
| 100 | —CH₂CN | —CH₂CH₂NH₂ | 27 | 1 |
| 101 | —CH₂CH₂OH | —CH₂CH₂NH₂ | 39 | 2,3 |
| 102 | —CH₂CH₂S-C₆H₄-COOH | —CH₃ | 64 | 4,5 |
| 103 | —CH₂CH₂Cl | —CH₂CH₂NH₂ | 47 | 2,6 |

Footnotes 1. n.m.r. in solvent A:-3.2–3.9(m, 6H); 4.36(m, 2H) 5.06(s, 2H); 5.18(d, 1H); 5.81(d, 1H); 7.04(s, 1H); 7.1(m, 2H); 8.2(m, 2H).

2. Product purified by HPLC on an octadecysilane column.

3. n.m.r. in solvent A:-3.3–3.8(m, 6H); 4.1–4.5(m, 6H); 5.19(d, 1H); 5.85(d, 1H); 7.0(s, 1H); 7.1(m, 2H); 8.4(m, 2H).

4. The starting material was 4-chloro-1-methylpyridinium iodide. No deprotection process was required.

mixture stirred for 1.5 hours. The solvent was evaporated and the residue dissolved in CH₂Cl₂. To this solution was added a solution of 7-amino-3-azidomethylceph-3-em-4-carboxylic acid (1.0 mM) in dichloromethane (2.5 ml.) under argon this solution having previously been treated at 0° with N,O-bistrimethylsilylacetamide (2.0 mM) and allowed to warm to ambient temperature over 2 hours. After 1.5 hours the mixture was diluted with CH₂Cl₂ and the organic layer washed with water, brine and dried (MgSO₄). Evaporation of the solvent gave the product. Using this general process the following compounds were prepared.

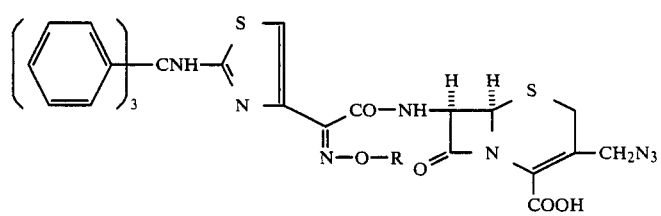

| —R | Footnotes |
|----|-----------|
| CH₂CN | 1 |
| —CH₂CH₂OH | 2,3 |

-continued

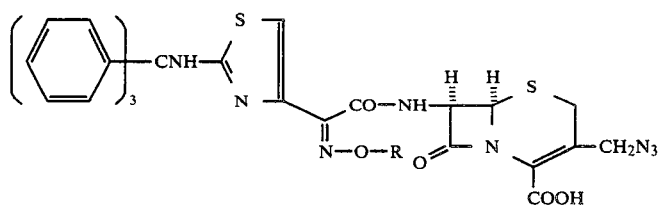

| —R | Footnotes |
|---|---|
| —CH₂CH₂S— 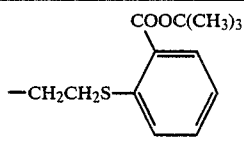 (COOC(CH₃)₃) | 4,5 |
| —CH₂CH₂Cl | 6 |

Footnotes 1. n.m.r. in solvent A:-3.4(s, 2H); 3.9(d, 1H); 4.4(d, 1H); 4.8(s, 2H); 4.9(d, 1H); 5.7(d, 1H); 6.8(s, 1H); 7.2(s, 15H).

2. The starting material may be prepared by reaction of ethyl 2-(2-tritylaminothiazol-4-yl)-2-((Z)-hydroxyimino)acetate with 1-bromo-2-(2-tetrahydropyran-2-yloxy)ethane and hydrolysis of the resulting ester to give 2-(2-tritylaminothiazol-4-yl)-2-[(Z)-2-(2-tetrahydropyran-2-yloxy)ethoxyimino]acetic acid. n.m.r. in solvent C:-1.6(m, 2H); 3.4–4.1(m, 6H); 4.4(t, 2H); 4.68(s, 1H); 6.68(s, 1H); 7.36(s, 15H).

3. n.m.r. in solvent C:-3.48(s, 2H); 3.95(m, 3H); 4.33(m, 3H); 5.05(d, 1H); 5.85(d, 1H); 6.76(s, 1H); 7.35(s, 15H).

4. The starting material may be prepared by reaction of ethyl 2-(2-tritylaminothiazol-4-yl)-2-((Z)-bromoethoxyimino)acetate (UK Patent Application No. 2017702) with t-butyl-2-mercaptobenzoate and hydrolysis of the resulting ester to give 2-(2-tritylaminothiazol-4-yl)-2-[(Z)-2-(2-t-butoxycarbonylphenylthio)ethoxyimino]acetic acid, n.m.r. in solvent C:-1.6(s, 9H); 3.3(t, 2H); 4.4(t, 2H); 6.67(s, 1H); 7.0–8.0(m, 4H); 7.34;L (s, 15H).

5. n.m.r. in solvent A:-1.52(s, 9H); 3.1–3.5(m, 4H); 3.9–4.6(m, 4H); 4.99(d, 1H); B 5.84(d, 1H); 6.76(s, 1H); 6.9–7.9(m, 4H); 7.27(s, 15H).

6. n.m.r. in solvent A:-3.5–4.6(m, 8H); 5.16(d, 2H); 5.66(d, 1H); 6.8(s, 1H); 7.36(s, 15H).

The crude 3-azidomethylcephalosporin derivative was dissolved in formic acid and treated with an excess of wet Raney nickel for 50 minutes. The mixture was filtered through diatomaceous earth and the pad rinsed with MeOH/water 1:1 v/v. The filtrate was evaporated and the residue dissolved in TFA/water 9:1 v/v (5 ml.) at ambient temperature. After 1.5 hours the solvent was evaporated and the product purified by chromatography on Diainon HP20 resin, eluting with increasing proportions of MeOH in water. There were thus obtained the following compounds.

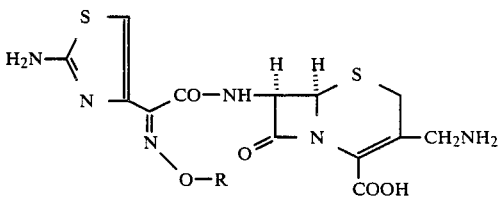

| —R | Footnotes |
|---|---|
| —CH₂CHCN | 1 |
| —CH₂CH₂OH | 2 |
| —CH₂CH₂S— (COOH phenyl) | 3 |
| —CH₂CH₂Cl | 4 |

Footnotes 1. n.m.r. in solvent A:-3.66(s, 2H); 3.78(q, 2H); 5.02(s, 2H); 5.15(d, 1H); 5.84(d, 1H); 6.98(s, 1H).

2. n.m.r. in solvent A:-3.73(m, 6H); 4.22(t, 2H); 5.2(d, 1H); 5.9(d, 1H); 7.0(s, 1H);

3. n.m.r. in solvent A:3.4(m, 2H); 3.5–4.0(m, 4H); 4.43(m, 2H); 5.23(d, 1H); 5.94(d, 1H); 7.1(s, 1H); 7.1–8.0(m, 4H).

4. n.m.r. in solvent A:-3.6–4.0(m, 6H); 4.39(t, 2H); 5.17(d, 1H); 5.87(d, 1H); 7.02(s, 1H).

EXAMPLES 104–115

The general process described in Examples 57–65 was repeated using the appropriate 3-aminomethylcephalosporin and 4-halopyridinio derivatives as starting materials, and the following compounds were obtained:

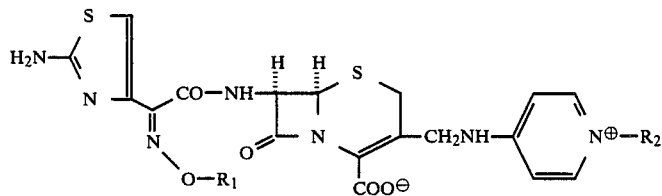
| Example | —R1 | —R2 | Yield % | Footnotes |
|---|---|---|---|---|
| 104 | —C(CH3)2COOH | -CH2-C6H4-CN (ortho) | 29 | 1, 2, 3, 4, 5 |
| 105 | —C(CH3)2COOH | -CH2-C6H4-OCH3 (meta) | 43 | 1, 6, 3, 4, 7 |
| 106 | —C(CH3)2COOH | -CH2-C6H4-CO2C2H5 (meta) | 31 | 1, 8, 3, 4, 9 |
| 107 | —C(CH3)2COOH | -CH2-C6H4-F (para) | 32 | 1, 10, 3, 4, 11, 12 |
| 108 | —C(CH3)2COOH | -CH2-C6H4-CH3 (para) | 37 | 1, 13, 3, 4, 14 |
| 109 | —C(CH3)2COOH | -CH2-C6H4-COOH (para) | 36 | 15, 3, 4, 16 |
| 110 | —C(CH3)2COOH | -CH2-C6H4-NO2 (para) | 23 | 1, 17, 18 |
| 111 | —CH3 | -CH2-C6H4-OCH3 (meta) | 32 | 19, 4, 20 |
| 112 | —CH3 | -CH2-C6H4-CO2C2H5 (meta) | 20 | 19, 4, 21 |
| 113 | —CH3 | -CH2-C6H4-F (para) | 52 | 22, 23, 24 |
| 114 | —C(CH3)2COOH | —CH2OCH2OCH3 | 22 | 25, 19, 26, 27 |

-continued

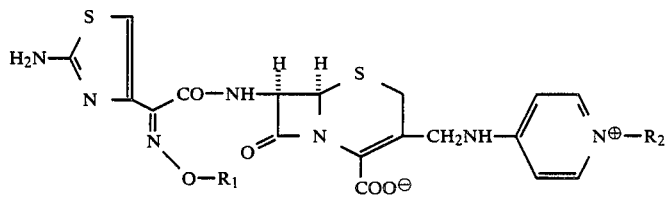

| Example | —R1 | —R2 | Yield % | Footnotes |
|---|---|---|---|---|
| 115 | —CH₃ | —CH₂OCH₂OCH₃ | 38 | 22, 28, 29 |

Footnotes

1. The starting material may be prepared by the following general process. The substituted benzyl halide (0.04M) and 4-pyridone (0.04M) were heated under reflux in dry acetone in the presence of anhydrous sodium carbonate (0.08M) for 3 hours. The mixture was filtered, the filtrate evaporated and the residue purified by chromatography. The purified product (0.01M) in dry toluene (15 ml.) was treated with toluene-p-sulphonyl chloride (0.01M) at 140°-150° for 10 minutes. After cooling the solvent was decanted from the residual oil. The oil was triturated with dry toluene and anhydrous ether, dried in vacuo and used without further purification.

2. Starting material was 4-chloro-1-(2-cyanobenzyl)-pyridinium toluene-p-sulphonate.

3. The reaction was carried out in acetonitrile/water 1:1 v/v for 18 hours.

4. Purification carried out by medium pressure chromatography on Merck Lichoprep RP18 using acetonitrile/water 7:3 v/v as eluant.

5. n.m.r. in solvent A:-1.4(s, 6H); 3.5(br d, 2H); 4.3(d, 2H); 5.1(d, 1H); 5.4(s, 2H); 5.8(d, 1H); 6.7(s, 1H); 6.8–8.2(m, 8H).

6. Starting material was 4-chloro-1-(3-methoxybenzyl)pyridinium toluene-p-sulphonate. n.m.r. in CDCl₃:-3.8(s, 3H); 4.9(s, 2H); 6.4(d, 2H); 6.8(m, 3H); 7.3(m, 3H).

7. n.m.r. in solvent A:-1.46(s, 6H); 3.54(q, 2H); 3.76(s, 3H); 4.34(q, 2H); 5.16(d, 1H); 5.32(d, 1H); 5.88(d, 1H); 6.76(s, 1H); 6.84–8.6(m, 8H).

8. Starting material was 4-chloro-1-(3-ethoxycarbonylbenzyl)pyridinium toluene-p-sulphonate: n.m.r. in CDCl₃:-1.35(t, 3H); 4.35(q, 2H); 4.95(s, 2H); 6.3(d, 2H); 7.4(m, 4H); 7.9(m, 2H).

9. n.m.r. in solvent A:-1.0–1.6(s, t, 9H); 3.5(q, 2H); 4.32(q, q, 4H); 5.12(d, 1H); 5.44(s, 2H); 5.92(d, 1H); 6.74(s, 1H); 6.88–7.4(brm, 2H); 7.5(d, 2H); 7.96(d, 2H); 8.16–8.6(brm, 2H).

10. The starting material was 4-chloro-1-(4-fluorobenzyl)pyridinium toluene-p-sulphonate, m.p. 140°-145°.

11. Further purification was carried out by chromatography on HP20 resin using water/acetonitrile 7:3 v/v as eluant.

12. n.m.r. in solvent A:-1.43(s, 6H); 3.41(d, 1H); 3.58(d, 1H); 4.22(d, 1H); 4.36(d, 1H); 5.13(d, 1H); 5.3(s, 2H); 5.83(d, 1H); 6.75(s, 1H); 6.8–8.4(m, 8H).

13. The starting material was 4-chloro-1-(4-methylbenzyl)pyridinium toluene-p-sulphonate, m.p. 124°-127°.

14. n.m.r. in solvent A:-1.4(s, 6H); 2.25(s, 3H); 3.45(q, 2H); 4.3(brq, 2H); 5.05(d, 1H); 5.15(s, 2H); 5.75(d, 1H); 6.7(s, 1H); 6.8–8.4(m, 8H).

15. The starting material was prepared by reaction of 4-chloropyridine with 4-carboxybenzyl bromide in acetone to give 4-chloro-1-(4-carboxybenzyl)pyridinium bromide. n.m.r. in d₆DMSO:-5.9(s, 2H); 7.55(d, 2H); 7.9(d, 2H); 8.35(d, 2H); 9.2(d, 2H).

16. n.m.r. in solvent A:-1.4(s, B 6H); 3.25(q, 2H); 4.3(q, 2H); 5.1(d, 1H); 5.4(s, 2H); 5.75(d, 1H); 6.7(s, 1H); 6.8–7.2(brm, 2H); 7.4(d, 2H); 7.9(d, 2H); 8.1–8.4(brm, 2H).

17. The starting material was 4-chloro-1-(4-nitrobenzyl)pyridinium chloride; n.m.r. in CDCl₃:-5.3(s, 2H); 6.3(d, 2H); 7.6(m, 4H); 8.25(d, 2H).

18. n.m.r. in solvent A:-1.5(s, 6H); 3.5(q, 2H); B 4.35(q, 2H); 5.1(d, 1H); 5.5(s, 2H); 5.75(d, 2H); 6.7(s, 1H); 6.8–7.2(m, 2H); 7.55(d, 2H); 8.2(d, 4H).

19. The reaction was carried out in water for 18 hours.

20. n.m.r. in solvent A:-3.45(q, 2H); 3.7(s, 3H); 3.8(s, 3H); 4.25(q, 2H); 5.05(d, 1H); 5.2(s, 2H); 5.7(d, 1H); 6.7(s, 1H); 6.8–8.4(m, 8H).

21. n.m.r. in solvent A:-1.3(t, 3H); 3.4(q, 2H); 3.8(s, 3H) 4.3(q, q 4H); 5.05(d, 1H); 5.4(s, 2H); 5.7(d, 1H); 6.7(s, 1H); 6.8–8.5(m, 8H).

22. Reaction time 18 hours.

23. Purification by chromatography on CHP200P resin using water/acetonitrile 7:3 v/v as eluant.

24. n.m.r. in solvent A:-3.45(q, 2H); 3.8(s, 3H); 4.3(q, 2H); 5.05–5.2(d, s, 3H); 3.7(d, 1H); 6.7(s, 1H); 6.8–8.4(m, 8H).

25. The starting material was prepared by reaction of 4-chloropyridine with 1-methoxy-2-chloromethoxyethane in ether to give 4-chloro-1-(2-methoxyethoxy)methylpyridinium bromide. n.m.r. in D₂O:-3.4(s, 3H); 3.7(m, 4H); 6.0(s, 2H); 8.25(d, 2H); 9.05(d, 2H).

26. Product purified by HPLC on an octadecylsilane column using MeOH/water/HOAc 35:64:1 v/v/v as eluant.

27. n.m.r. in solvent A:-1.44(brs, 6H); 3.2(s, 3H); 3.4–3.68(m, 6H); 4.36(q, 2H); 5.16(d, 1H); 5.47(s, 2H); 5.86(d, 1H); 6.95(s, 1H); 7.05(t, 1H); 8.28(q, 2H).

28. Product purified by HPLC on an octadecylsilane column using MeOH/water/HOAc 20:79:1 v/v/v as eluant.

29. n.m.r. in solvent C:-3.1(s, 3H); 3.4(m, 6H); 3.75(s, 3H); 4.22(brs, 2H); 5.0(d, 1H); 5.17(d, 2H); 5.6(d, 1H); 6.3(d, 2H); 6.66(s, 1H); 6.89(t, 1H); 7.8(d, 2H).

EXAMPLES 116-120

To a stirred suspension of 3-aminomethyl-7-[2-(2-aminothiazol-4-yl)-2-((Z)-methoxyimino acetamido]-ceph-3-em-4-carboxylic acid (0.5 mM) in water (3 ml.) and acetonitrile (1 ml.) was added sodium bicarbonate (1.5 mM). When a clear solution had formed 1-bromo-2-methylisoquinolinium tetrafluoroborate (0.5 mM) was added. After 30 minutes HOAc (1.5 mM) was added and the product was isolated on an HP20 column using acetonitrile/water gradient elution. Using this general procedure, and the appropriate haloisoquinolinium starting materials, the following compounds were prepared.

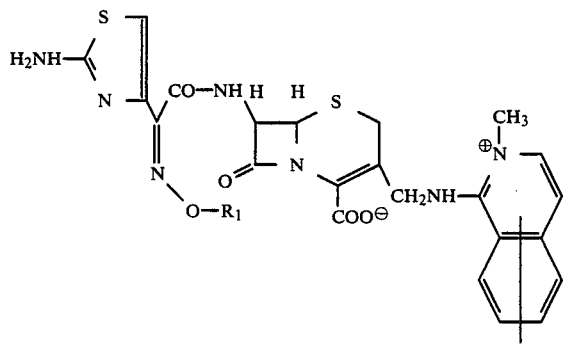

| Example | —R1 | R2 | Yield % | Footnotes |
|---|---|---|---|---|
| 116 | —C(CH3)2COOH | H | 15 | 1, 2, 3 |
| 117 | —CH3 | H | 58 | 4 |
| 118 | —C(CH3)2COOH | 4-Br | 28 | 5, 6 |
| 119 | —CH3 | 4-Br | 52 | 7 |
| 120 | —C(CH3)2COOH | 5-NO2 | 24 | 8, 9 |

Footnotes

1. Reaction carried out in water
2. The starting material was prepared by reaction of 1-bromoisoquinoline with trimethyloxonium tetrafluoroborate in CH2Cl2 to give 1-bromo-2-methylisoquinolinium tetrafluoroborate, m.p. 162°.
3. n.m.r. in solvent A:-1.45(s, 6H); 3.7(s, 2H); 4.0(s, 3H); 4.8(d, 2H); 5.15(d, 1H); 5.8(d, 1H); 6.7(s, 1H); 7.3(d, 1H); 7.4–8.0(m, 4H); 8.35(d, 1H).
4. n.m.r. in solvent A:-3.7(s, 2H); 3.85(s, 3H); 4.0(s, 3H); 4.85(d, 2H); 5.1(d, 2H); 5.8(d, 1H); 6.7(s, 1H); 7.4(d, 1H); 7.6–8.0(m, 4H); 8.4(d, 1H).
5. The starting material was prepared by reaction of 1-bromoisoquinoline with HBr to give 1,4-dibromoisoquinoline, m.p. 95°–96°, followed by reaction of this compound with trimethyloxonium tetrafluoroborate in CH2Cl2 to give 1,4-dibromo-2-methylisoquinolinium tetrafluoroborate; n.m.r. in solvent A:-3.5(s, 3H); 7.2–8.4(m, 5H).
6. n.m.r. in solvent A:-1.45(s, 6H); 3.7(s, 2H); 4.0(s, 3H); 4.8(d, 2H); 5.15(d, 1H); 5.8(d, 1H); 6.75(s, 1H); 7.7–8.5(m, 5H).
7. n.m.r. in solvent A:-3.7(s, 1H); 3.85(s, 3H); 4.0(s, 3H); 4.85(d, 2H); 5.15(d, 1H); 5.8(d, 1H); 6.75(s, 1H); 7.7–8.5(m, 5H).
8. The starting material was prepared by reactio of 1-bromoisoquinoline in concentrated H2SO4 at 0° with KNO3. The reaction mixture was worked up with water, NaHCO3 and EtOAc to give 1-bromo-5-nitro isoquinoline, m.p. 187°–8°. Reaction of this compound with trimethyloxonium tetrafluoroborate in CH2Cl2 gave impure 1-bromo-2-methyl-5-nitroisoquinolinium tetrafluoroborate which was used as such. n.m.r. in solvent A:-3.5(s, 3H); 7.7–8.7(m, 5H).
9. n.m.r. in solvent A:-1.45(m, 6H); 3.7(s, 2H); 3.95(s, 3H); 4.83(q, 2H); 5.15(d, 1H); 5.82(d, 1H); 6.73(s, 1H); 7.7–8.7(m, 5H).

EXAMPLES 121–125

To a stirred suspension of 3-aminomethyl-7-[2-(2-aminothiazol-4-yl)-2-((Z)-1-carboxy-1-methylethoxylmino)acetamido]ceph-3-em-4-carboxylic acid (240 mg, 0.5 mmole) and triethylamine (200 µl, 1.4 mmole) in EtOH (10 ml.) at 25° was added 1-methyl-4-methylthioquinazolinium iodide (160 mg. 0.5 mmole). After 1.5 hours the solution was evaporated to dryness under reduced pressure, the residue dissolved in water (10 ml.), the solution acidified with excess 5% v/v aqueous HOAc and the insoluble material filtered off. The filtrate was applied to a Diaion HP20 column and the product purified by gradient elution with MeOH. Using this general process and the appropriate quaternary heterocycle, the following compounds were obtained:

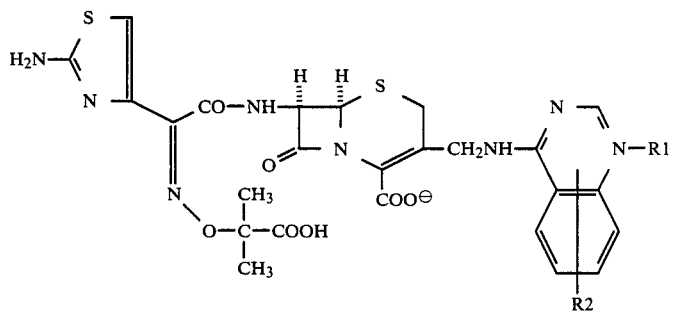

| Example | —R1 | R2 | Yield % | Footnotes |
|---|---|---|---|---|
| 121 | —CH3 | H | 30 | 1 |
| 122 | —CH2CH=CH2 | H | 35 | 2,3,4 |
| 123 | —CH3 | 2-CH2CH2CH3 | 60 | 5,6 |
| 124 | —CH3 | 7-Cl | 35 | 7,8 |
| 125 | —CH2—C6H5 | H | 32 | 9,10 |

Footnotes 1. n.m.r. in solvent A:-1.42(s, 3H); 1.45(s, 3H); 3.55(q, 2H); 4.0(s, 3H); 4.8(q, 2H); 5.1(d, 1H); 5.82(d, 1H);

6.72(s, 1H); 7.85(t, 1H); 8.0(d, 1H); 8.12(t, 1H); 8.55(d, 1H); 8.95(s, 1H).

2. The precipitate was redissolved in a minimum amount of dilute HOAc (5% v/v in water) and the product isolated by chromatography on Diaion CHP 20 resin eluting with increasing amounts of MeOH in water. Appropriate fractions were combined, MeOH removed by evaporation and the residue freeze-dried.

3. The quinazolinium salt may be prepared as follows. A solution of 4-methylthioquinazoline (1.76 g., 10 mmole) and allyl bromide (5.0 μl, 60 mmole) in acetonitrile (10 ml.) was heated under reflux for 4 hours. On cooling crystals of the quaternary salt deposited, which were filtered off and washed with ether. n.m.r. ind$_6$DMSO:-2.9(s, 3H); 5.3–5.6(complex, 4H); 5.95–6.4(m, 1H), 7.9–8.5(complex, 4H), 9,9(s, 1H).

4. n.m.r. in solvent A:-1.41(s, 3H); 1.43(s, 3H); 3.5(d, 1H); 3.65(d, 1H); 4.64(d, 1H); 4.99(d, 1H); 5.1(d, 1H); 5.15(m, 2H); 5.31(m, 2H); 5.84(d, 1H); 6.06(m, 1H); 6.75(s, 1H); 7.82(m, 1H); 7.95(m, 1H); 8.06(m, 1H); 8.55(m, 1H); 8.97(s, 1H).

5. The starting material may be prepared as follows. A mixture of 2-propylquinazol-4-oneand 2,4-bis(4-methoxyphenyl)-2,4-dithioxo-P$^5$, P$^5$-1,3,2,4-dithiaphosphetane (Lawesson's Reagent) (5.7 g.) in dimethoxyethane (100 ml.) was stirred and heated under reflux for 4 hours. The precipitate was separated from the cooled mixture and recrystallised from EtOH to give 2-propyl-4-mercaptoquinazoline; n.m.r. ind$_6$DMSO:-1.15(t, 3H); 1.9(m, 2H); 2.8(t, 3H); 7.4–8.75(complex, 4H).

A mixture of 2-propyl-4-mercaptoquinazoline (3.3 g.) and sodium hydroxide (0.68 g.) in water (7 ml.) was stirred for 10 minutes at 25°. Methyl iodide (1.1 ml.) was added and stirring was continued for 1 hour. The precipitate was recrystallised from hexane to give 4-methylthio-2-propylquinazoline; n.m.r. in CDCl$_3$:-1.1(t, 3H); 1.95(m, 2H); 2.7(s, 3H); 3.0(t, 2H); 7.2–8.1(complex, 4H).

A solution of 2-propyl-4-methylthioquinazoline (1.08 g.) in methyl iodide (5 ml.) was heated under reflux for 18 hours. The solid was separated from the cooled mixture and washed with ether to give 1-methyl-4-methylthio-2-propylquinazolinium iodide; n.m.r. in d$_6$DMSO:-1.15(t, 3H); 2.0(m, 2H); 2.9(s, 3H); 3.35(t, 2H); 4.3(s, 3H); 7.9–8.6(complex, 4H).

6. n.m.r. in solvent A:-1.0(t, 3H); 1.4(s, 3H); 1.43(s, 3H); 1.8(m, 2H); 3.03(t, 2H); 3.53(q, 2H); 3.96(s, 3H); 4.56(d, 1H); 5.04(d, 1H); 5.06(d, 1H); 5.82(d, 1H); 6.72(s, 1H); 7.6–8.5(complex, 4H).

7. The starting material may be prepared by repeating the first, second and third parts of Footnote 5, using 7-chloroquinazol-4-one to give 7-chloro-4-mercaptoquinazoline, 7-chloro-4-methylthioquinazoline, 7-chloro-4-methylthioquinazoline [n.m.r. in CDCl$_3$:-2.7(s, 3H); 7.4–8.1(complex, 3H); 8.95(s, 1H)] and 7-chloro-1-methyl-4methylthioquinazolinium iodide [n.m.r. in d$_6$DMSO:-2.9(s, 3H); 4.3(s, 3H); 8.0–8.6(complx, 3H); 9.7(s, 1H).]

8. n.m.r. in solvent A:-1.4(s, 3H); 1.43(s, 3H); 3.53(q, 2H); 3.97(s, 3H); 4.62(d, 1H); 4.96(d, 1H); 5.09(d, 1H); 5.84(d, 1H); 6.72(s, 1H); 7.9–8.9(complex, 4H).

9. The starting material may be prepared by repeating the third part of Footnote 5, using 4-methylthioquinazoline, to give 1-benzyl-4-methylthioquinolinium chloride, n.m.r. in d$_6$DMOS:-2.9(s, 3H); 6.2(s, 2H); 7.2(-8.5-(complex, 9H); 10.15(s, 1H).

10. n.m.r. in solvent A:-1.4(s, 3A); 1.43(s, 3H); 3.6(q, 2H); 4.66(d, 1H); 5.02(d, 1H); 5.1(d, 1H); 5.75(s, 2H); 5.84(d, 1H); 7.32(m, 5H); 7.75–8.55(complex, 4H); 9.18(s, 1H).

EXAMPLES 126–130

The process described in Examples 57–65 was repeated, using the appropriate starting materials, to give the following compounds.

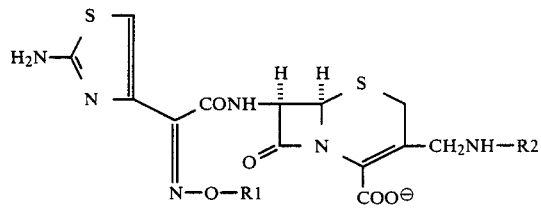

| Example | —R1 | —R2 | Yield % | Footnotes |
|---|---|---|---|---|
| 126 | —CH$_3$ | ⊕N—CH$_2$CH=CH$_2$ (pyridinium) | 38 | 1 |
| 127 | —CH$_3$ | ⊕N—cyclopropyl (pyridinium) | 40 | 2 |
| 128 | —C(CH$_3$)$_2$COOH | CH$_3$, ⊕N—CH$_2$CH$_3$ (isoquinolinium) | 32 | 3,4 |

-continued

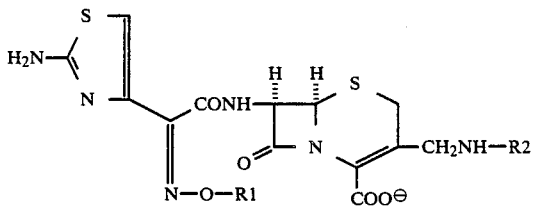

| Example | —R1 | —R2 | Yield % | Footnotes |
|---|---|---|---|---|
| 129 | —C(CH3)2COOH | (2-methyl-1-allyl-quinolinium) | 16 | 5,6 |
| 130 | —C(CH3)2COOH | (2-methyl-1-methyl-6-fluoroquinolinium) | 17 | 7,8 |

Footnotes 1. n.m.r. in solvent A:-8.2(d, 1H); 8.02(d, 1H); 7.05(d, 1H); 6.92(d, 1H); 6.72(s, 1H); 5.7–6.2(m, 1H); 5.72(d, 1H); 5.2–5.4(m, 2H); 5.08(d, 1H); 4.73(d, 2H); 4.4(d, 1H); 4.16(d, 1H); 3.81(s, 3H); 3.6(d, 1H); 3.34(d, 1H).

2. n.m.r. in solvent A:-8.3(d, 1H); 8.15(d, 1H); 7.01(d, 1H); 6.92(d, 1H); 6.75(s, 1H); 5.75(d, 1H); 5.1(d, 1H); 4.44(d, 1H); 4.2(d, 1H); 3.6–4.0(m, 1H); 3.84(s, 3H); 3.6(d, 1H); 3.32(d, 1H); 0.95–1.3(m, 4H).

3. The starting material was prepared by reaction of 1-ethyl-2-methyl-4-quinolone with toluene-p-sulphonyl chloride to give 4-chloro-1-ethyl-2-methylquinolinium toluene-p-sulphonate.

4. n.m.r. in solvent A:-7.3–8.65(m, 5H); 6.76(s, 1H); 5.72(d, 1H); 5.05(d, 1H); 4.56(br, 2H); 4.32(q, 2H); 3.6(d, 1H); 3.35(d, 1H); 2.78(s, 3H); 1.42(s, 6H); 1.38(t, 3H).

5. The starting material was prepared as follows. A solution of 4-amino-2-methylquinoline (5.0 g.) and allyl bromide (3.32 ml.) in nitrobenzene (13.7 ml.) was stirred at 100° for 1 hour. The reaction mixture was cooled to below 5° and the resulting precipitate filtered off, washed with ether and dried. A suspension of this material in N aqueous NaOH (75 ml.) was stirred at 100° for 3.5 hours. The cooled mixture was extracted with EtOAc (2×75 ml.) and the combined extracts washed, dried and evaporated to give 1-allyl-2-methyl-4-quinolone. Reaction of this compound with toluene-p-sulphonyl chloride gave 1-allyl-4-chloro-2-methylquinolinium toluene-p-sulphonate.

6. n.m.r. in solvent A:-8.46(d, 1H); 7.8–7.95(m, 2H); 7.65(t, 1H); 7.22(s, 1H); 6.73(s, 1H); 6.05(m, 1H); 5.72(d, 1H); 5.04(d, 1H); 5.2(d, 1H); 5.1(br, 1H); 4.8(d, 1H); 4.75(d, 1H); 4.56(d, 1H); 4.52(d, 1H); 3.55(d, B 1H); 3.4(d, 1H); 2.63(s, 3H); 1.4(s, 6H).

7. The starting material was prepared by reaction of 1,2-dimethyl-6-fluoro-4-quinoline with toluene-p-sulphonyl chloride to give 4-chloro-1,2-dimethyl-6-fluoroquinolinium toluene-p-sulphonate.

8. n.m.r. in solvent A:-7.7–8.6(m, 3H); 7.04(s, 1H); 6.72(s, 1H); 5.82(d, 1H); 5.13(d, 1H); 4.54(br, 2H); 4.0(s, 3H); 3.56(br, 2H); 2.72(s, 3H); 1.4(s, 6H).

EXAMPLE 131

The process described in Example 67a was repeated using 1-((Z)-2-t-butoxycarbonylaminoethyl)-4-chloropyridinium toluene-p-sulphonate as starting material The residue from the reaction mixture was treated with TFA for 10 minutes, evaporated, the residue diluted with water and the product purified by chromatography to give the following compound in 38% yield:

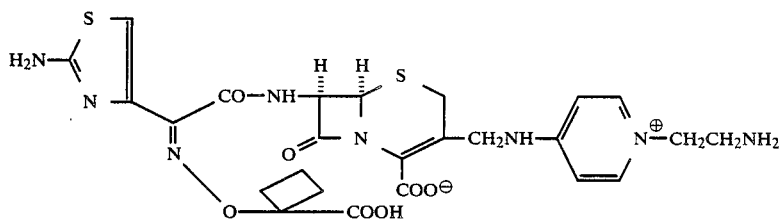

n.m.r. in solvent B: 1.9(m,2H); 2.4(m,4H); 3.3(m,2H); 3.4(d,1H); 3.6(d,1H); 4.2(d,1H); 4.3(d,m,3H); 5.15(d,1H); 5.85(d,1H); 6.95(d,1H); 7.05(d,m,2H); 8.0(d,1H); 8.2(d,1H).

EXAMPLES 132-135

The general process described in Examples 16-22 or 23-52 was repeated, using the appropriate chloroheterocycle as starting material unless otherwise stated, and the following compounds were prepared.

n.m.r. in solvent B:-2.71(s, 3H); 5.6(s, 2H); 7.98(d, 2H); 8.84(d, 2H). Oxidation of this compound with meta-chlorperbenzoic acid in $CH_2Cl_2$ at 0° to ambient temperature for 5 hours gave 1-amidinomethyl-4-methylsulphinylpyridinium chloride. n.m.r. in solvent B:-2.99(s, 3H); 8.6(d, 2H); 9.38(d, 2H).

6. Reaction carried out using 1-[2-(t-butoxy carbonylamino)ethyl]-4-chloropyridinium toluene-p-sulphonate. Yield 40%.

7. HPLC eluant water/MeOH/HOAc 599:40:1 v/v/v.

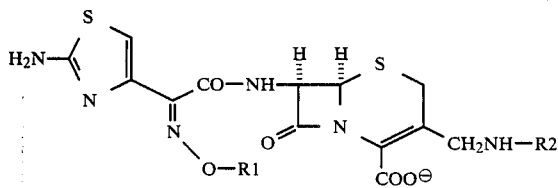

| Example | —R1 | —R2 | Yield % | Footnotes |
|---|---|---|---|---|
| 132 | —C(CH₃)₂COOH | pyridinium-NO₂ (N—H) | 4 | 1,2 |
| 133 | —C(CH₃)₂COOH | pyridinium-CH₂C(=NH)NH₂ | 36 | 3,4,5 |
| 134 | —CH₃ | pyridinium-CH₂CH₂NH₂ | 100 | 6,7,8,9 |
| 135 | —C(CH₃)₂COOH | pyridinium (N—CH₃) O—CH₂—C₆H₄—NO₂ | 33 | 10,11,12 |

Footnotes

1. HPLC eluant water/MeOH/HOAc 74:25:1 v/v/v.
2. n.m.r. in solvent B:-3.4–3.7(m, 2H); 4.5–4.8(m, 2H); 5.2(d, 1H); 5.9(d, 1H); 7.0(s, 1H); 7.55(d, 1H); 8.5(d, 1H); 9.4(s, 1H).
3. HPLC eluant water/MeOH/HOAc 89:10:1 v/v/v.
4. n.m.r. in solvent B:-1.56(s, 6H); 3.4(d, 1H); 3.66(d, 1H); 4.38(s, 2H); 5.16(s, 2H); 5.14(d, 1H); 5.82(d, 1H); 7.0(s, 1H); 6.9–7.2(m, 2H); 8.0–8.4(m, 2H).
5. The starting material was obtained by reaction of 4-methylthiopyridine with 2-chloracetamidine hydrochloride in EtOH under reflux for 18 hours to give 1-amidinomethyl-4-methylthiopyridinium chloride.

8. Purified product treated with $CH_2Cl_2$/TFA 1:2 v/v for 30 minutes. Reaction mixture poured into ether.
9. n.m.r. in solvent B:-3.2–3.6(m, 4H); 3.96(s, 3H); 4.1–4.6(m, 4H); 5.15(d, 1H); 5.77(d, 1H); 7.07(s, 1H); 6.9–7.3(m, 2H); 8.0–8.4(m, 2H).
10. HPLC eluant water/MeOH/HOAc 54:45:1 v/v/v.
11. n.m.r. in solvent B:-1.55(s, 6H); 3.4–3.6(m, 2H); 3.95(s, 3H); 4.4–4.6(m, 2H); 5.2(d, 1H); 5.9(d, 1H); 5.4(s, 2H); 7.1(s, 1H); 7.0-7.2, 8.2-8.4(m, m, 3H); 7.8-8.3(m, 4H).

12. The starting material was prepared by reaction of 4-nitro-3-hydroxy pyridine-N-oxide with acetyl chloride under reflux for 1 hour. The crude product was purified by rapid chromatography on silica gel using $CH_2Cl_2$/MeOH 7:3 v/v as eluant to give 4-chloro-3-hydroxypyridine-N-oxide. Reduction of this compound with Raney nickel and hydrogen at ambient temperature for 2 hours in MeOH gave 4-chloro-3-hydroxypyridine. This compound was reacted with NaH in DMSO at 50°, the reaction mixture cooled and treated with 4-nitrobenzyl bromide for 1 hour. The reaction mixture was worked up with water and ether and the product treated with HCl/ether to give 4-chloro-3-(4-nitrobenzyloxy)pyridine hydrochloride. Reaction of the free base with excess methyl iodide at ambient temperature for 24 hours gave 4-chloro-1-methyl-3-(4-nitrobenzyloxy)pyridinium iodide. n.m.r. in $d_6$DMSO-4.3(s, 3H); 5.6(s, 2H); 7.7(d, 2H); 8.3(d, 2H); 8.4(d, 1H); 8.7(d, 1H); 9.15(s, 1H).

EXAMPLE 136

The general process described in Examples 57-65 was repeated and the following compound was obtained in 77% yield.

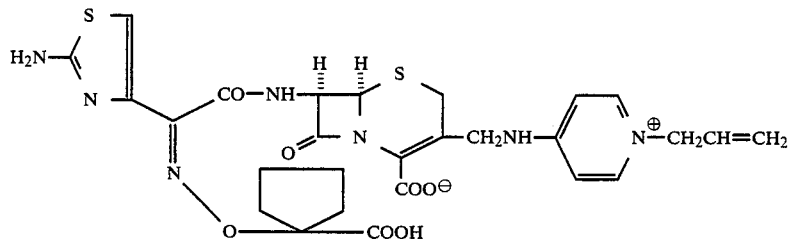

N.m.r. in solvent A: 1.67(br,4H); 2.05(br,4H); 3.23(d,1H); 3.53(d,1H); 4.2(d,1H); 4.45(d,1H); 4,74(d,1H); 5.02(d,1H); 5.1-5.3(m,2H); 5.65(d1H); 5.8-6.1(m,1H); 6.73(s,1H); 6.97(br,1H); 7.28(br,1H); 8.07(br,2H).

The starting material was prepared by the condensation of 2-[((Z)-1-t-butoxycarbonyl)cyclopent-1-yl)]oxyimino-2-(2-tritylaminothiazol-4-yl)acetic acid and 7-amino-3-azidomethylceph-3-em-4-carboxylic acid using the method of Footnote 3 of Example 66 to give 3-azidomethyl-7-(2-[((Z)-1-t-butoxycarbonyl)cyclopent-1-yloximino]-2-(2-tritylaminothiazol-4-yl)acetamido)-ceph-3-em-4-carboxylic acid having the following n.m.r. in $CDCl_3$: 1.38(s,9H); 1.72(br,4H); 2.06(br,4H); 3.3(d,1H); 3.54(d,1H); 3.87(d,1H); 4.34(d,1H); 5.03(d,1H); 5.82(q,1H); 6.69(s,1H); 7.27(s,15H); 8.18(d,1H).

The azidomethyl compound was reduced by the continuation of the above procedure to the 3-aminomethyl compound, which was purified by chromatography on XAD-2 resin, and used without full characterisation.

FORMULAE

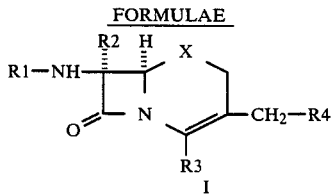

I

-continued
FORMULAE

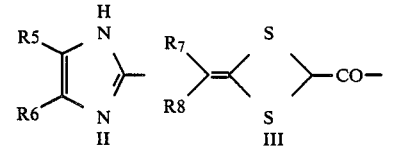

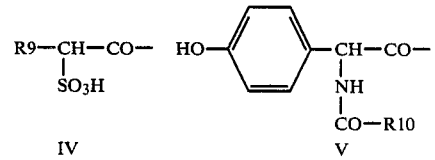

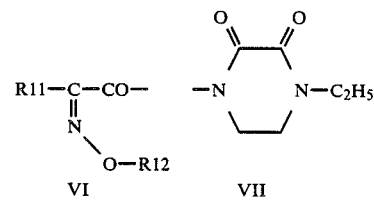

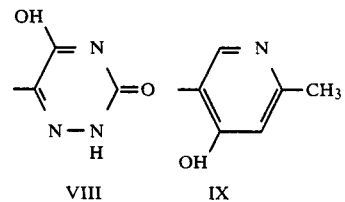

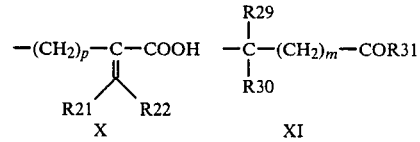

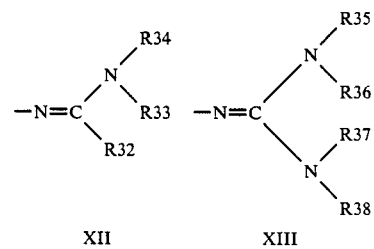

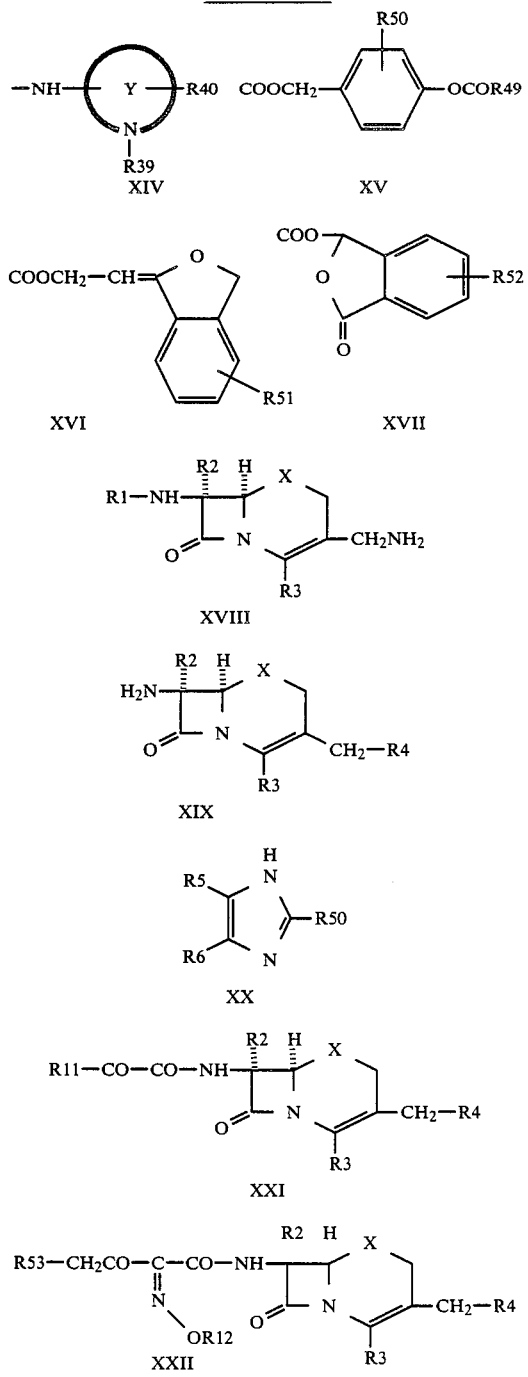

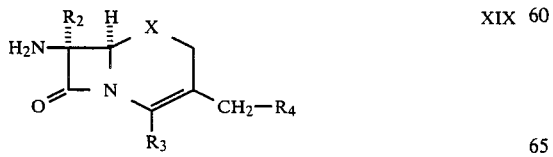

What we claim is:
1. A cephalosporin derivative of the formula XIX:

in which
X is sulphur or sulphinyl (R or S configuration);

R2 is hydrogen or methoxy;
R3 is carboxy or a biodegradable ester thereof, or where R4 carries a positive charge, a carboxylate anion;
R4 is of the formula XII, XIII or XIV:

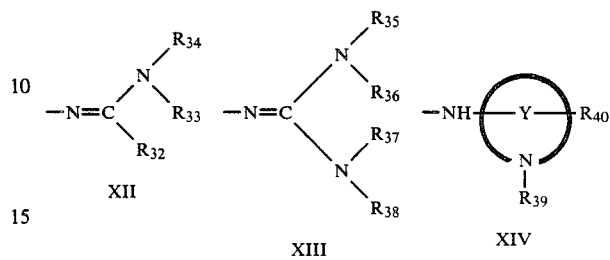

or a tautomeric form thereof, in which the radical of the formula XIV may carry a positive charge, and the acid-addition salts thereof, in which R32 is hydrogen, (1-6C)alkyl, phenyl, naphthyl or —(CH$_2$)$_q$—COOR41 in which q is 1 to 6 and R41 is hydrogen or (1-6C)alkyl;

R33 and R34 are selected from hydrogen, (1-6C)alkyl, hydroxy, cyano, phenyl, naphthyl, phenyl(-1-6C)alkyl, heteroaryl and —(CH$_2$)$_q$—COOR41 in which q and R41 have the meanings given above, or R33 and R34 are joined to form, together with the nitrogen to which they are attached, a pyrrolidine, piperidine, morpholine or hexahydroazepine ring, said ring being unfused or fused to a benzene ring, or R32 and R33 are joined by a carbon chain to form, together with the carbon and nitrogen to which they are attached, a 5- or 6-membered saturated ring which is unfused or which is fused to a benzene ring;

R35 and R37 are selected from hydrogen, (1-6C)alkyl, phenyl(1-6C)alkyl and —(CH$_2$)$_q$COOR41 in which q is 1 to 6 and r41 is hydrogen (1-6C)alkyl;

R36 and r38 are selected from hydrogen, (1-6C)alkyl, phenyl, naphthyl and phenyl(1-6C)alkyl;

or R36 and R37 are joined as a carbon chain to form, together with the nitrogen-carbon-nitrogen chain to which they are attached, a saturated or partially unsaturated 5- or 6-membered ring which is unfused or which is fused to a benzene ring;

ring Y is pyridine, pyrimidine, oxazole, thiazole, isoxazole, isothiazole or imidazole each of which is unfused or fused to a benzene, cyclopentane or cyclohexane ring;

R39 is hydrogen, amino, (1-6C)alkyl, (3-6C)cycloalkyl, (3-6C)alkenyl, (2-8C)alkoxyalkyl, —(CH$_2$)q—COOR41, —(CH$_2$)$_q$—CONH$_2$, —(CH$_2$)q— S(O)$_s$—R42 or —(CH$_2$)q—NHCO—R42 in which q is 1 to 6, R41 is hydrogen or (1-6C)alkyl, s is 0, 1 or 2 and R42 is (1-6C)alkyl or (1-6C) alkoxy, or R39 is (3-8C)alkanoylmethyl, benzoylmethyl, (1-6C)primaryhydroxyalkyl, (1-6C)-primaryaminoalkyl, (1-4C)alkyamino(1-6C)alkyl, di(1-4C)alkylamino(1-6C)alkyl, (1-6C)alkoxy, (1-6C)alkylamino, phenyl(1-6C)alkyl, phenyl(1-6C)alkoxy, (1-4C)alkoxy(1-4C)alkyl, (1-6C)alkoxy(2-4C)alkoxy(1-4C)alkyl, or of the formula (CH$_2$)$_n$—N=CR43NR44R45 or (CH$_2$)$_n$C(NR43)NR44R45 (or a tautomer thereof) in which n is 1 to 4 and R43, R44 and R45, same or different, are hydrogen or (1-4C)-alkyl;

R40 is hydrogen or one or two substituents selected from halogen, amino, nitro, (1-6C)alkyl, carboxy, (2-6C)alkoxycarbonyl, (1-6C)alkoxy, cyano, carbamoyl, (1-6C)haloalkyl, (1-6C)azidoalkyl, (1-6C)aminoalkyl, (2-4C)aminoalkylthio(1-4C)alkyl, (2-6C)alkanoylamino, (2-6C)alkanoylamino(1-4C)alkyl, (2-6C)alkanoyloxy(1-4C)alkyl, benzyl, benzyloxy and heteroarylthio;

wherein when R33, R34, R35, R36, R37, R38, R39 or R40 individually is or contains phenyl or naphthyl, the phenyl or naphthyl is unsubstituted or substituted by one or two radicals selected from halogen, nitro, cyano, carboxy, hydroxy, carbamoyl, (1-6C) alkyl, (1-6C) alkoxy and (2-6C) alkoxycarbamoyl, and wherein when R33 or R34 is heteroaryl, or R40 is heteroarylthio, the heteroaryl ring is a 5- or 6-membered ring containing 1, 2 or 3 hetero atoms selected from oxygen, nitrogen and sulphur, provided that not more than one heteroatom shall be selected from the group consisting of oxygen and sulphur.

2. The cephalosporin derivative according to claim 1 wherein X is sulphur.

3. The cephalosporin derivative according to claim 1 wherein R3 is carboxy or a biodegradable ester thereof or, where R4 carries a positive charge, a carboxylate anion; and R4 is of the formula XII, XIII or XIV

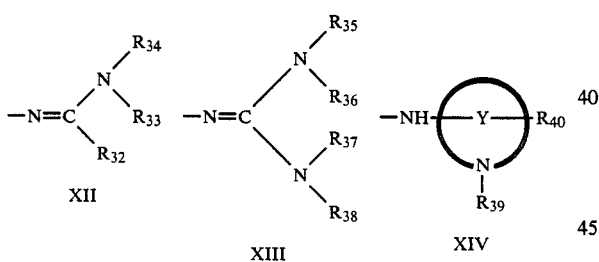

XII  XIII  XIV or a tautomeric form thereof, in which the radical of the formula XIV may carry a positive charge, and in which R32 is hydrogen, methyl, phenyl, naphthyl or —(CH$_2$)$_q$—COOR41 in which q is 1 to 6 and R41 is hydrogen or methyl;

R33 and R34 are selected from hydrogen, methyl, hydroxy, cyano, phenyl, naphthyl, benzyl, furyl, pyrrolyl, thienyl, thiazolyl, isothiazolyl, oxazolyl, isoxazolyl, imidazolyl, pyrazolyl, 1,2,3-thiadiazolyl, 1,2,4-thiadiazolyl, 1,2,3-oxadiazolyl, 1,2,4-oxadiazolyl, 1,2,3-triazolyl, 1,2,4-triazolyl, tetrazolyl, pyrimidinyl, pyridyl, pyrazinyl or (CH$_2$)$_q$—COOR41 in whch q and R41 have the meanings given above, or R33 and R34 are joined to form, together with the nitrogen to which they are attached, a pyrrolidine, piperidine, morpholine or hexahydroazepine ring, said ring being unfused or fused to a benzene ring, or R32 and R33 are joined by a carbon chain to form, together with the carbon and nitrogen to which they are attached, a 5- or 6-membered saturated ring which is unfused or which is fused to a benzene ring;

R35 and R37 are selected from hydrogen, methyl, benzyl or —(CH$_2$)$_q$COOR41 in which q is 1-6 and R41 is hydrogen or methyl;

R36 and R38 are selected from hydrogen, methyl, phenyl, naphthyl or benzyl; or

R36 and R37 are joined as a carbon chain to form, together with the nitrogen-carbon-nitrogen chain to which they are attached, a saturated or partially unsaturated 5- or 6-membered ring which is unfused or which is fused to a benzene ring;

ring Y is pyridine, pyrimidine, oxazole, thiazole, isoxaziole, isothiazole or imidazole each of which is unfused or fused to a benzene, cyclopentane or cyclohexane ring;

R39 is hydrogen, amino, methyl, ethyl, n-propyl, i-propyl, t-butyl, cyclopropyl, cyclobutyl, cyclopentyl, cyclohexyl, allyl, but-3-enyl, but-4-enyl, methoxymethyl, 2-methoxyethyl, ethoxymethyl, —(CH$_2$)$_q$—COOR41, —(CH$_2$)$_q$—CONH$_2$, —(CH$_2$)$_q$—S(O)$_s$—R42 or —(CH$_2$)$_q$—NH-CO—R42 in which q is 1 to 6, R41 is hydrogen or methyl, s is 0, 1 or 2 and R42 is methyl, ethyl, methoxy, ethoxy or t-butoxy, or R39 is acetylmethyl benzoylmethyl, 2-hydroxyethyl, 2-aminoethyl, 2-methylaminoethyl, 2-dimethylaminoethyl, methoxy, ethoxy, n-propoxy, i-propoxy, methylamino, ethylamino, benzyl, 4-nitrobenzyl, 2-phenethyl, benzyloxy, 2-phenoxyethyl, (2-methoxyethyl)methyl, or of the formula (CH$_2$)$_n$N=CR43NR44R45

(CH$_2$)$_n$C(NR43)NR44R45 (or a tautomer thereof) in which n is 1 to 4 and R43, R44 and R45, same or different are hydrogen or methyl;

R40 is hydrogen or one or two substituents selected from fluorine, chlorine, bromine, amino, nitro, methyl, ethyl, n-propyl, i-propyl, t-butyl, carboxy, methoxycarbonyl, ethoxycarbonyl, methoxy, ethoxy, cyano, carbamoyl, chloromethyl, bromomethyl, trifluoromethyl, 2-chloroethyl, azidomethyl, aminomethyl, 2-aminoethyl, (2-aminoethylthio)methyl, acetylamino, acetylaminomethyl, 2-acetylaminoethyl, acetoxymethyl, 2-acetoxyethyl, benzyl, benzyloxy, furylthio, pyrrolylthio, thienylthio, thiazolylthio, isothiazolylthio, oxazolylthio, isoxazolylthio, imidazolylthio, pyrazolylthio, 1,2,3-thiadiazolylthio, 1,2,4-thiadiazolylthio, 1,2,3-oxadiazolylthio, 1,2,4-oxadiazolylthio, 1,2,3-triazolylthio, 1,2,4-triazolylthio, tetrazolylthio, pyrimidinylthio, pyridylthio or pyrazinylthio; and wherein when R33, R34, R35 R36, R37, R38, R39 or R40 individually is or contains phenyl or naphthyl, the phenyl naphthyl is unsubstituted or substituted by one or two radicals selected from fluorine, chlorine, bromine, nitro, cyano, carboxy, hydroxy, carbamoyl, methyl, methoxy or ethoxycarbonyl.

4. The cephalosporin derivative according to claim 1 wherein R3 is carboxy and R4 is of the formula XIV

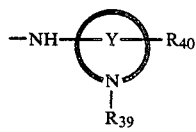  XIV and R39, R40 and Y are as defined in claim 1.

5. The cephalosporin derivative according to claim 1 wherein R4 is of the formula XIV

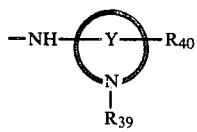  XIV in whch ring Y is pyridine which is unfused or fused to a benzene or cyclopentane ring, pyrimidine which is unfused or fused to a benzene ring, thiazole or isoazole and R39 and R40 are as defined in claim 1.

6. The cephalosporin derivative according to claim 5 wherein R39 is methyl, ethyl, n-propyl, i-propyl, allyl, carbamoylmethyl, (2-acetylamino)ethyl, methylthiomethyl, 2-hydroxyethyl, 2-aminoethyl, 4-nitrobenzyl, $CH_2CH_2N=C(H_3)NH_2$ or $CH_2C(NH)NH_2$ and R40 is hydrogen, fluorine, amino, methyl, methoxy or carbamoyl.

7. The cephalosporin derivative according to claim 1 wherein R4 to selected from the group consisting of

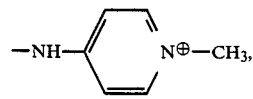

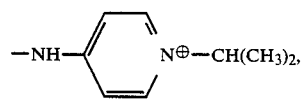

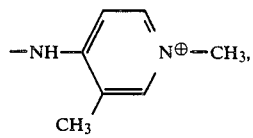

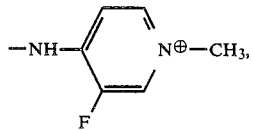

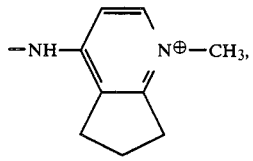

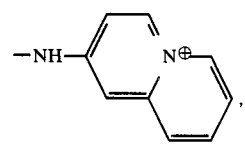

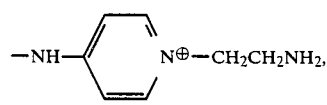

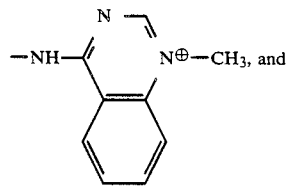 and

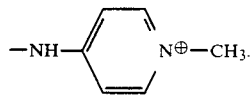

* * * * *